United States Patent
Chirgwin et al.

(10) Patent No.: US 11,883,468 B2
(45) Date of Patent: Jan. 30, 2024

(54) COMPOSITIONS AND METHODS TO SUPPRESS TUMOR GROWTH IN BONE, PREVENT CACHECTIC MUSCLE LOSS, AND PRESERVE SKELETAL INTEGRITY

(71) Applicant: United States Government As Represented By The Department of Veterans Affairs, Washington, DC (US)

(72) Inventors: John Chirgwin, Indianapolis, IN (US); Attaya Suvannasankha, Indianapolis, IN (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 103 days.

(21) Appl. No.: 17/077,716

(22) Filed: Oct. 22, 2020

(65) Prior Publication Data
US 2021/0113667 A1    Apr. 22, 2021

Related U.S. Application Data

(60) Provisional application No. 62/924,416, filed on Oct. 22, 2019.

(51) Int. Cl.
*A61K 38/29* (2006.01)
*A61P 35/04* (2006.01)
*A61K 45/06* (2006.01)

(52) U.S. Cl.
CPC .............. *A61K 38/29* (2013.01); *A61K 45/06* (2013.01); *A61P 35/04* (2018.01)

(58) Field of Classification Search
CPC .......... A61K 38/29; A61K 45/06; A61P 35/04
See application file for complete search history.

(56) References Cited

PUBLICATIONS

Evans et al [Clinical Nutrition, 2008, 27, 793-799] (Year: 2008).*
Morley et al [Am.J.Clin.Nutr., 2006, 83, 735-743] (Year: 2006).*
Aoyagi et al [World J Gastrointest Oncl, Apr. 15, 2015, 7(4), 17-29] (Year: 2015).*
Sadeghi et al [Critical Reviews in Oncology/Hematology, 2018, 127, 91-104] (Year: 2018).*
Argiles et al [Nature Reviews Cancer, 2014, 14, 754-762] (Year: 2014).*
Megase_2010, Fact sheet on Megase from FDA, 2010 (Year: 2010).*
Fact sheet on Edromizu, 2020 (Year: 2020).*
Appleton KM, Lee M-H, Alele C, et al. Biasing the Parathyroid Hormone Receptor. Methods in Enzymology: Elsevier; 2013. p. 229-62.
Birch MA, Carron JA, Scott M, et al. Parathyroid hormone/PTH-related protein receptor expression and mitogenic responses in human breast cancer cell lines. British Journal of Cancer. 1995;72(1):90-5.
Bohinc BN, Gesty-Palmer D. Arrestins in Bone. Progress in Molecular Biology and Translational Science: Elsevier; 2013. p. 335-58.
Boudot C, Hénaut L, Thiem U, et al. Overexpression of a functional calcium-sensing receptor dramatically increases osteolytic potential of MDA-MB-231 cells in a mouse model of bone metastasis through epiregulin-mediated osteoprotegerin downregulation. Oncotarget. 2017;8(34).
Bravo-Sagua R, Mattar P, Díaz X, et al. Calcium Sensing Receptor as a Novel Mediator of Adipose Tissue Dysfunction: Mechanisms and Potential Clinical Implications. Frontiers in Physiology. 2016;7.
Brooks SL, Neville AM, Rothwell NJ, et al. Sympathetic activation of brown-adipose-tissue thermogenesis in cachexia. Bioscience Reports. 1981;1(6):509-17.
Cafforio P, Savonarola A, Stucci S, et al. PTHrP produced by myeloma plasma cells regulates their survival and pro-osteoclast activity for bone disease progression. JBMR. 2013;29(1):55-66.
Carron JA, Fraser WD, Gallagher JA. PTHrP and the PTH/PTHrP receptor are co-expressed in human breast and colon tumours. British Journal of Cancer. 1997;76(8):1095-8.
Casey AE, Ross GL, Langston RR. Selective XYZ Factor in C57 Black Mammary Carcinoma Eo771. Experimental Biology and Medicine. 1949;72(1):83-9.
Chirgwin JM, Guise TA. Molecular Mechanisms of Tumor-Bone Interactions in Osteolytic Metastases. Critical Reviews in Eukaryotic Gene Expression. 2000;10(2):20.
Chorev M, Goldman ME, et al. Modifications of position 12 in a parathyroid hormone and parathyroid hormone-related protein: toward the design of highly potent antagonists. Biochemistry. 1990;29(6):1580-6.
Chung E, Yamashita H, Au P, et al. Secreted Gaussia Luciferase as a Biomarker for Monitoring Tumor Progression and Treatment Response of Systemic Metastases. PLoS One. 2009;4(12):e8316.
Clines GA. Mechanisms and treatment of hypercalcemia of malignancy. Current Opinion in Endocrinology & Diabetes and Obesity. 2011;18(6):339-46.
Collin-Osdoby P, Yu X, et al. RANKL-Mediated Osteoclast Formation from Murine RAW 264.7 Cells. Bone Research Protocols: Humana Press., 2003 p. 153-166.
de la Mata J, Uy HL, Guise TA, et al. Interleukin-6 enhances hypercalcemia and bone resorption mediated by parathyroid hormone-related protein in vivo. Journal of Clinical Investigation. 1995;95(6):2846-52.

(Continued)

*Primary Examiner* — Sudhakar Katakam
(74) *Attorney, Agent, or Firm* — Ballard Spahr LLP

(57) ABSTRACT

Disclosed are methods of decreasing cachexia in a subject comprising administering to the subject a therapeutically effective amount of bPTH7-34DD or variant thereof. Disclosed are methods of decreasing bone destruction in a subject comprising administering to the subject a therapeutically effective amount of bPTH7-34DD or variant thereof. Disclosed are methods of ameliorating one or more symptoms or side effects of breast or prostate cancer in a breast or prostate cancer patient comprising administering to the subject a therapeutically effective amount of bPTH7-34DD or variant thereof. Disclosed are methods of treating osteoporosis in a subject comprising administering to the subject a therapeutically effective amount of bPTH7-34DD or variant thereof.

7 Claims, 22 Drawing Sheets

(56) References Cited

PUBLICATIONS de Paula FJA, Rosen CJ. Structure and Function of Bone Marrow Adipocytes. Comprehensive Physiology: John Wiley & Sons, Inc.; 2017. p. 315-49.
Delgado-Calle J. Osteoclasts Control Lipid Secretion to Regulate Breast Cancer Bone Metastasis. Endocrinology. 2017;158(3):458-60.
Delgado-Calle J, Anderson J, et al. Genetic deletion of Sost or pharmacological inhibition of sclerostin prevent multiple myeloma-induced bone disease without affecting tumor growth. Leukemia. 2017;31(12):2686-94.
Delgado-Calle J, Tu X, Pacheco-Costa R, et al. Control of Bone Anabolism in Response to Mechanical Loading and PTH by Distinct Mechanisms Downstream of the PTH Receptor. JBMR. 2016;32(3):522-35.
Dempster DW, Compston JE, Drezner MK, et al. Standardized nomenclature, symbols, and units for bone histomorphometry. JBMR. 2013;28(1):2-17.
Dempster DW, Hughes-Begos CE, Plavetic-Chee K, et al. Normal human osteoclasts formed from peripheral blood monocytes express PTH type 1 receptors and are stimulated by PTH in the absence of osteoblasts. Journal of Cellular Biochemistry. 2005;95(1):139-48.
Diel IJ, Body J-J, Stopeck AT, et al. The role of denosumab in the prevention of hypercalcaemia of malignancy in cancer patients with metastatic bone disease. European Journal of Cancer. 2015;51(11):1467¬75.
Downey SE, Hoyland J, Freemont AJ, et al. Expression of the receptor for parathyroid hormone-related protein in normal and malignant breast tissue. The Journal of pathology. 1997;183(2):212-7.
Drew AF, Blick TJ, Lafleur MA, et al. Correlation of tumor- and stromal-derived MT1-MMP expression with progression of human ovarian tumors in SCID mice. Gynecologic Oncology. 2004;95(3):437-48.
Elefteriou F. Role of sympathetic nerves in the establishment of metastatic breast cancer cells in bone. Journal of Bone Oncology. 2016;5(3):132-4.
Fairfield H, Falank C, Harris E, et al. The skeletal cell-derived molecule sclerostin drives bone marrow adipogenesis. Journal of Cellular Physiology. 2018;233(2):1156-67.
Falank C, Fairfield H, Reagan MR. Reflections on Cancer in the Bone Marrow: Adverse Roles of Adipocytes. Current Molecular Biology Reports. 2017;3(4):254-62.
Fallah-Rad N, Morton AR. Managing hypercalcaemia and hypocalcaemia in cancer patients. Current Opinion in Supportive and Palliative Care. 2013;1.
Falzon M., et al., Enhanced Growth of MCF-7 Breast Cancer Cells Overexpressing Parathyroid Hormone-Related Peptide. Endocrinology. 2000;141(5):1882-92.
Fan Y, Hanai J-i, Le PT, et al. Parathyroid Hormone Directs Bone Marrow Mesenchymal Cell Fate. Cell Metabolism. 2017;25(3):661-72.
Faucheux C, Horton MA, Price JS. Nuclear Localization of Type I PTH/Parathyroid Hormone-Related Protein Receptors in Deer Antler Osteoclasts: Evidence for Parathyroid Hormone-Related Protein and Receptor Activator of NF-κB-Dependent Effects on Osteoclast Formation in Rege. JBMR. 2002;17(3):455-64.
Ferguson JE, Seaner RM, et al. Expression and specific immunolocalization of the human PTH/PTHrP receptor in the uteroplacental unit. American Journal of Obstetrics and Gynecology. 1998;179(2):321-9.
Fountas A, Andrikoula M, Giotaki Z et al. The emerging role of denosumab in the long-term management of parathyroid carcinoma-related refractory hypercalcemia. Endocrine Practice. 2015;21(5):468-73.
Fournier PGJ, Chirgwin JM, Guise TA. New insights into the role of T cells in the vicious cycle of bone metastases. Current Opinion in Rheumatology. 2006;18(4):396-404.

Fukayama S, Kong G, Benovic JL, et al. β-Adrenergic Receptor Kinase-1 Acutely Regulates PTH/PTHrP Receptor Signalling in Human Osteoblastlike Cells. Cellular Signalling. 1997;9(6):469-74.
Gardella TJ. Inverse agonism of amino-terminally truncated PTH and PTH-related peptide (PTHrP) analogs revealed with constitutively active mutant PTH/PTHrP receptors. Endocrinology. 1996;137(9):3936-41.
Gesta S, Tseng Y-H, Kahn CR. Developmental Origin of Fat: Tracking Obesity to Its Source. Cell. 2007;131(2):242-56.
Gesty-Palmer D, Flannery P, Yuan L, et al. Arrestin-Biased Agonist of the Parathyroid Hormone Receptor Promotes Bone Formation Independent of G Protein Activation. Science Translational Medicine. 2009;1(1).
Gesty-Palmer D, Luttrell LM. 'Biasing' the parathyroid hormone receptor: A novel anabolic approach to increasing bone mass? British Journal of Pharmacology. 2011;164(1):59-67.
Gesty-Palmer D, Yuan L, Martin B, et al. β-Arrestin-Selective G Protein-Coupled Receptor Agonists Engender Unique Biological Efficacyin Vivo. Molecular Endocrinology. 2013;27(2):296-314.
Goldman ME, McKee RL, Caulfield MP, et al. a new highly potent parathyroid hormone antagonist: [D-TRPI2, TYR34]bPTH-(7-34)NH2. Endocrinology. 1988; 123(5):2597-9.
González Á, García de Durango C, Alonso V, et al. Distinct Osteomimetic Response of Androgen-Dependent and Independent Human Prostate Cancer Cells to Mechanical Action of Fluid Flow: Prometastatic Implications. The Prostate. 2016;77(3):321-33.
Grundmann M, Merten N, Malfacini D, et al. Lack of beta-arrestin signaling in the absence of active G proteins. Nature communications. 2018;9(1).
Guise TA, Kozlow WM, Heras-Herzig A, et al. Molecular Mechanisms of Breast Cancer Metastases to Bone. Clinical Breast Cancer. 2005;5:S46-S53.
Guise TA, Yin JJ, Taylor SD, Kumagai Y, et al. Evidence for a causal role of PTHrP in the pathogenesis of human breast cancer-mediated osteolysis. Journal of Clinical Investigation. 1996;98(7):1544-9.
Harms M, Seale P. Brown and beige fat: development, function and therapeutic potential. Nature Medicine. 2013;19(10):1252-63.
Hattersley G, Dean T, Corbin BA, et al. Binding Selectivity of Abaloparatide for PTH-Type-1-Receptor Conformations and Effects on Downstream Signaling. Endocrinology. 2016; 157(1):141-9.
Hock JM, Gera I. Effects of continuous and intermittent administration and inhibition of resorption on the anabolic response of bone to parathyroid hormone. JBMR. 2009;7(1):65-72.
Hu MI, Glezerman IG, Leboulleux S, et al. Denosumab for Treatment of Hypercalcemia of Malignancy. The Journal of Clinical Endocrinology & Metabolism. 2014;99(9):3144-52.
Ikeda K, Mangin M, Dreyer BE, et al. Identification of transcripts encoding a parathyroid hormone-like peptide in messenger RNAs from a variety of human and animal tumors associated with humoral hypercalcemia of malignancy. Journal of Clinical Investigation. 1988;81(6):2010-4.
Iwamura M, Wu G, Abrahamsson P-A, et al. Parathyroid hormone-related protein: A potential autocrine growth regulator in human prostate cancer cell lines. Urology. 1994;43(5):675-9.
Johnson RW, Suva LJ. Hallmarks of Bone Metastasis. Calcified Tissue International. 2017;102(2):141-51.
Juárez P, Fournier PGJ, Mohammad KS, et al. Halofuginone inhibits TGF/BMP signaling and in combination with zoledronic acid enhances inhibition of breast cancer bone metastasis. Oncotarget. 2017;8(49).
Juarez P, Mohammad KS, Yin JJ, et al. Halofuginone Inhibits the Establishment and Progression of Melanoma Bone Metastases. Cancer Res. 2012;72(23):6247-56.
Kajimura S, Spiegelman BM, Seale P. Brown and Beige Fat: Physiological Roles beyond Heat Generation. Cell Metabolism. 2015;22(4):546-59.
Käkönen S-M, Selander KS, Chirgwin JM, et al. Transforming Growth Factor-β Stimulates Parathyroid Hormone-related Protein and Osteolytic Metastases via Smad and Mitogen-activated Protein Kinase Signaling Pathways. Journal of Biological Chemistry. 2002;277(27):24571-8.
Kim BH, Pereverzev A, Zhu S, et al. Extracellular nucleotides enhance agonist potency at the parathyroid hormone 1 receptor. Cellular Signalling. 2018.

(56) References Cited

PUBLICATIONS

Kim SP, Frey JL, Li Z, et al. Sclerostin influences body composition by regulating catabolic and anabolic metabolism in adipocytes. Proceedings of the National Academy of Sciences. 2017;114(52):E11238-E47.

Kim W, Takyar FM, Swan K, et al. Calcium-Sensing Receptor Promotes Breast Cancer by Stimulating Intracrine Actions of Parathyroid Hormone-Related Protein. Cancer Res. 2016;76(18):5348-6.

Kir S, Komaba H, Garcia Ana P, et al. PTH/PTHrP Receptor Mediates Cachexia in Models of Kidney Failure and Cancer. Cell Metabolism. 2016;23(2):315-23.

Kir S, White JP, Kleiner S, Kazak L, et al. Tumour-derived PTH-related protein triggers adipose tissue browning and cancer cachexia. Nature. 2014;513(7516):100-4.

Kukreja SC, D'Anza JJ, Wimbiscus SA, et al. Inactivation by plasma may be responsible for lack of efficacy of parathyroid hormone antagonists in hypercalcemia of malignancy. Endocrinology. 1994;134(5):2184-8.

Langub MC, Malluche HH. Parathyroid Hormone Type 1 Receptor and Human Osteoclasts. JBMR. 2002;17(10):1916.

Lecka-Czernik B, Stechschulte LA, Czernik PJ, et al. Marrow Adipose Tissue: Skeletal Location, Sexual Dimorphism, and Response to Sex Steroid Deficiency. Frontiers in Endocrinology. 2017;8.

Leder BZ, O'Dea LSL, Zanchetta JR, et al. Effects of Abaloparatide, a Human Parathyroid Hormone-Related Peptide Analog, on Bone Mineral Density in Postmenopausal Women with Osteoporosis. The Journal of Clinical Endocrinology & Metabolism. 2015;100(2):697-706.

Li J, Karaplis AC, Huang DC, et al. PTHrP drives breast tumor initiation, progression, and metastasis in mice and is a potential therapy target. Journal of Clinical Investigation. 2011;121(12):4655-69.

Liao J, Li X, Koh AJ, Berry JE, et al. Tumor expressed PTHrP facilitates prostate cancer-induced osteoblastic lesions. International Journal of Cancer. 2008;123(10):2267-78.

Lupp A, Klenk C, Rocken C, et al. Immunohistochemical identification of the PTHR1 parathyroid hormone receptor in normal and neoplastic human tissues. European Journal of Endocrinology. 2010;162(5):979-86.

Luttrell LM, Maudsley S, Bohn LM. Fulfilling the Promise of "Biased" G Protein-Coupled Receptor Agonism. Molecular Pharmacology. 2015;88(3):579-88.

Luttrell LM, Maudsley S, Gesty-Palmer D. Translating in vitro ligand bias into in vivo efficacy. Cellular Signalling. 2018;41:46-55.

Massfelder T, Parekh N, et al. Effect of intrarenally infused parathyroid hormone-related protein on renal blood flow and glomerular filtration rate in the anaesthetized rat. BJ of Pharmacology. 1996;118(8):1995-2000.

Maudsley S, Martin B, Janssens J, et al. Informatic deconvolution of biased GPCR signaling mechanisms from in vivo pharmacological experimentation. Methods. 2016;92:51-63.

Mickle AD, Shepherd AJ, Loo L, et al. Induction of thermal and mechanical hypersensitivity by parathyroid hormone-related peptide through upregulation of TRPV1 function and trafficking. PAIN. 2015;156(9):1620-36.

Milgrom DP, Lad NL, Koniaris LG, et al. Bone Pain and Muscle Weakness in Cancer Patients. Current Osteoporosis Reports. 2017;15(2):76-87.

Mohammad KS, Chirgwin JM, Guise TA. Assessing New Bone Formation in Neonatal Calvarial Organ Cultures. Osteoporosis: Humana Press; 2008. p. 37-50.

Moseley JM, Kubota M, Diefenbach-Jagger H, et al. Parathyroid hormone-related protein purified from a human lung cancer cell line. Proceedings of the National Academy of Sciences. 1987;84(14):5048-52.

Bohinc B, Gesty-Palmer D. Biased Agonism at the Parathyroid Hormone Receptor: A Demonstration of Functional Selectivity in Bone Metabolism. Mini-Reviews in Medicinal Chemistry. 2012;12(9):856-65.

Onuma E. Increased Renal Calcium Reabsorption by Parathyroid Hormone-Related Protein Is a Causative Factor in the Development of Humoral Hypercalcemia of Malignancy Refractory to Osteoclastic Bone Resorption Inhibitors. Clinical Cancer Research. 2005;11(11):4198-203.

Parkes A, Clifton K, Al-Awadhi A, et al. Characterization of bone only metastasis patients with respect to tumor subtypes. npj Breast Cancer. 2018;4(2).

Pennisi A, Ling W, Li X, et al. Consequences of Daily Administered Parathyroid Hormone on Myeloma Growth, Bone Disease, and Molecular Profiling of Whole Myelomatous Bone. PLoS One. 2010;5(12):e15233.

Peters EMJ, Foitzik K, Paus R, et al. A New Strategy for Modulating Chemotherapy-Induced Alopecia, Using PTH/PTHrP Receptor Agonist and Antagonist. Journal of Investigative Dermatology. 2001;117(2):173-8.

Bovenberg MS, Degeling MH, Tannous BA. An Enhanced Gaussia luciferase blood assay for monitoring of in vivo biological processes. Anal Chem. Jan. 17, 2012;84(2):1189-92. doi: 10.1021/ac202833r. Epub Dec. 27, 2011. PMID: 22148161.

Johnson RW, Sun Y, Ho PWM, Chan ASM, Johnson JA, Pavlos NJ, Sims NA, Martin TJ. Parathyroid Hormone-Related Protein Negatively Regulates Tumor Cell Dormancy Genes in a PTHR1/Cyclic AMP-Independent Manner. Front Endocrinol (Lausanne). May 16, 2018;9:241. doi: 10.3389/fendo.2018.00241. eCollection 2018. PMID: 29867773.

Maudsley S, Martin B, Gesty-Palmer D, Cheung H, Johnson C, Patel S, Becker KG, Wood WH 3rd, Zhang Y, Lehrmann E, Luttrell LM. Delineation of a conserved arrestin-biased signaling repertoire in vivo. Mol Pharmacol. Apr. 2015;87(4):706-17. doi: 10.1124/mol.114.095224. Epub Jan. 30, 2015. PMID: 25637603.

Siclari VA, Mohammad KS, Tompkins DR, Davis H, Mckenna CR, Peng X, Wessner LL, Niewolna M, Guise TA, Suvannasankha A, Chirgwin JM. Tumor-expressed adrenomedullin accelerates breast cancer bone metastasis. Breast Cancer Res. Dec. 2, 2014;16(6):458. doi: 10.1186/s13058-014-0458-y. PMID: 25439669.

Wright LE, Ottewell PD, Rucci N, Peyruchaud O, Pagnotti GM, Chiechi A, Buijs JT, Sterling JA. Murine models of breast cancer bone metastasis. Bonekey Rep. May 11, 2016;5:804. eCollection 2016. PMID: 27867497.

Peterson YK, Luttrell LM. The Diverse Roles of Arrestin Scaffolds in G Protein-Coupled Receptor Signaling. Pharmacological Reviews. 2017;69(3):256-97.

Pierroz DD, Rufo A, Bianchi EN, et al. β-Arrestin2 Regulates RANKL and Ephrins Gene Expression in Response to Bone Remodeling in Mice. JBMR. 2009;24(5):775-84.

Pizurki L, Rizzoli R, Bonjour JP. Inhibition by (D-Trp12,Tyr34)bPTH(7-34)amide of PTH and PTHrP effects on Pi transport in renal cells. American Journal of Physiology-Renal Physiology. 1990;259(2):F389-F92.

Qiu T, Wu X, Zhang F, et al. TGF-13 type II receptor phosphorylates PTH receptor to integrate bone remodelling signalling. Nature Cell Biology. 2010.

Rahman S, Lu Y, Czernik PJ, et al. Inducible Brown Adipose Tissue, or Beige Fat, Is Anabolic for the Skeleton. Endocrinology. 2013;154(8):2687-701.

Rickard DJ, Wang F-L, Rodriguez-Rojas A-M, et al. Intermittent treatment with PTH as well as a non-peptide small molecule agonist of the PTH1 receptor inhibits adipocyte differentiation in human bone marrow stromal cells. Bone. 2006;39(6):1361-72.

Rosen ED, Spiegelman BM. Adipocytes as regulators of energy balance and glucose homeostasis. Nature. 2006;444(7121):847-53.

Rosen ED, Spiegelman BM. What We Talk About When We Talk About Fat. Cell. 2014; 156(1-2):20-44.

Santos-Zas I, Lodeiro M, Gurriaran-Rodríguez U, et al. 13-Arrestin signal complex plays a critical role in adipose differentiation. The International Journal of Biochemistry & Cell Biology. 2013;45(7):1281-92.

Sato K. Treatment of malignancy-associated hypercalcemia and cachexia with humanized anti-parathyroid hormone-related protein antibody. Seminars in Oncology. 2003;30:167-73.

(56) References Cited

PUBLICATIONS

Shepherd AJ, Mickle AD, Kadunganattil S, et al. Parathyroid Hormone-Related Peptide Elicits Peripheral TRPV1-dependent Mechanical Hypersensitivity. Frontiers in cellular neuroscience. 2018;12.

Siclari VA, Mohammad KS, Tompkins DR, et al. Tumor-expressed adrenomedullin accelerates breast cancer bone metastasis. Breast Cancer Research. 2014;16:458.

Skrok A, Bednarczuk T, Skwarek A, et al. The Effect of PTHs on Hair Follicle Physiology: Implications for Treatment of Chemotherapy-Induced Alopecia. Skin Pharmacology and Physiology. 2015;28(4):213-25.

Strewler GJ, Stern PH, Jacobs JW, et al. Parathyroid hormonelike protein from human renal carcinoma cells. Structural and functional homology with parathyroid hormone. J Clinical Investigation. 1987;80(6):1803-7.

Suva L, Winslow G, Wettenhall R, et al. A parathyroid hormone-related protein implicated in malignant hypercalcemia: cloning and expression. Science. 1987;237(4817):893-6.

Suvannasankha A, Chirgwin JM. Role of bone-anabolic agents in the treatment of breast cancer bone metastases. Breast Cancer Research. 2014;16(6).

Swami S, Johnson J, Bettinson LA, et al. Prevention of breast cancer skeletal metastases with parathyroid hormone. JCI Insight. 2017;2(17).

Tannous BA, Teng J. Secreted blood reporters: Biotechnology Advances. 2011;29(6):997-1003.

Tsuzuki S, Park SH, Eber MR, et al. Skeletal complications in cancer patients with bone metastases. International Journal of Urology. 2016;23(10):825-32.

Weng T, Mao F, Wang Y, et al. Osteoblastic molecular scaffold Gab1 is required for maintaining bone homeostasis. Journal of Cell Science. 2010;123(5):682-9.

Wright LE, Ottewell PD, et al. Murine models of breast cancer bone metastasis. BoneKEy reports. 2016;5.

Wu G, Iwamura M, Di Sant'agnese PA, et al. Characterization of the cell-specific expression of parathyroid hormone-related protein in normal and neoplastic prostate tissue. Urology. 1998;51(5):110-20.

Wysolmerski JJ, Stewart AF. The physiology of parathyroid hormone-related protein: An Emerging Role as a Developmental Factor. Annual Review of Physiology. 1998;60(1):431-60.

Xiao N, Li H, Mei W, et al. SUMOylation Attenuates Human 13-Arrestin 2 Inhibition of IL-1R/TRAF6 Signaling. Journal of Biological Chemistry. 2014;290(4):1927-35.

Yaccoby S. Osteoblastogenesis and tumor growth in myeloma. Leukem & Lymphoma. 2010;51:213-20.

Yin JJ, Selander K, Chirgwin JM, et al. TGF-13 signaling blockade inhibits PTHrP secretion by breast cancer cells and bone metastases development. Journal of Clinical Investigation. 1999;103(2):197-206.

Yoneda T, Hiasa M, Nagata Y, et al. Acidic microenvironment and bone pain in cancer-colonized bone. BoneKEy reports. 2015;4.

Zangari M, Berno T, Yang Y, et al. Parathyroid hormone receptor mediates the anti-myeloma effect of proteasome inhibitors. Bone. 2014; 61:39-43.

Zhang X, Cheng Q, Wang Y, et al. Hedgehog signaling in bone regulates whole-body energy metabolism through a bone-adipose endocrine relay mediated by PTHrP and adiponectin. Cell Death & Differentiation. 2016;24(2):225-37.

Zhou JZ, Riquelme MA, Gao X, et al. Differential impact of adenosine nucleotides released by osteocytes on breast cancer growth and bone metastasis. Oncogene. 2014;34(14):1831-42.

* cited by examiner

FIG. 18A,
FIG. 18B,
FIG. 18C,
FIG. 18D,

No tumor

MDA231, PBS

MDA-231 BDDP 40 ug/kg/day

COMPOSITIONS AND METHODS TO SUPPRESS TUMOR GROWTH IN BONE, PREVENT CACHECTIC MUSCLE LOSS, AND PRESERVE SKELETAL INTEGRITY

CROSS-REFERENCE TO RELATED APPLICATIONS

This application claims the benefit of U.S. Provisional Patent Application No. 62/924,416, filed on Oct. 22, 2019, which is incorporated by reference herein in its entirety.

BACKGROUND

Most patients with advanced cancers including but not limit to breast, prostate and lung cancers suffer from incurable bone metastases. Multiple myeloma, an incurable blood cancer, originates in the bone marrow causing similar bone complications as solid tumors that metastasize to the bones. Osteoclast activation and osteoblast suppression lead to bone loss, pathologic fractures, bone pain, hypercalcemia and skeletal muscle loss (cachexia). Therapies targeting osteoclasts have limited effects on tumor growth, while not restoring lost bone or muscle.

PTHrP, parathyroid hormone-related protein, is made by most cancer cell types and is central to the pathology of cancer bone metastasis. PTHrP increases RANKL to activate osteoclastic bone resorption and release other bone-imbedded nutrients and TGFβ. These factors further drive tumor growth and tumor-secreted PTHrP to drive a vicious cycle. PTHrP causes hypercalcemia of malignancy by altering calcium resorption at the kidneys. PTHrP can directly promote growth of cancers that express its receptor (PTH1R). PTHrP sensitizes nociceptive sensory neurons to increase bone pain, and causes adipocytes to secrete cachectic factors. PTHrP is thus a central cause of bone metastases and cachexia. PTHrP-neutralizing antibody fails to control tumor growth or repair bone loss while PTH/PTHrP analogs used for osteoporosis can inhibit mouse bone metastases, but they carry a black box osteosarcoma warning and have dose-limiting toxicity.

bPTH7-34DD is a biased agonist of PTH1R. Normal PTH (1-84), PTHrP (1-141), and the PTH analogs approved for osteoporosis, Teriparatide, abaloparatide, all bind the same receptor (in bone, kidney and elsewhere) PTH1R. Major response is increased cAMP.

BRIEF SUMMARY bPTH7-34DD has unique activities compared to PTH or PTHrP. It binds to PTH1R but activates the beta-arrestin pathway, which is only a secondary response of the PTH analogs, while not affecting cAMP. bPTH7-34DD activates osteoblast proliferation and differentiation without compensatory osteoclast activation, seen with other PTH analogs. By not activating cAMP and downstream protein kinases, bPTH7-34DD is expected not to have osteosarcoma side effects. Disclosed herein are uses of bPTH7-34DD or a variant thereof for suppressing tumor growth in bones, stimulating bone formation and decreasing cancer cachexia.

Disclosed are methods of decreasing cancer growth in the bones in cancer patients with cancer bone metastasis or preventing bone metastasis in patients with local cancers comprising administering to the subject a therapeutically effective amount of bPTH7-34DD or a variant thereof.

Disclosed are methods of decreasing bone destruction in a subject comprising administering to the subject a therapeutically effective amount of bPTH7-34DD or a variant thereof.

Disclosed are methods of decreasing cachexia in a subject comprising administering to the subject a therapeutically effective amount of bPTH7-34DD or a variant thereof.

Disclosed are methods of treating osteoporosis in a subject comprising administering to the subject a therapeutically effective amount of bPTH7-34DD or a variant thereof.

Disclosed are methods of ameliorating one or more symptoms or side effects of cancer bone metastasis comprising administering to the subject a therapeutically effective amount of bPTH7-34DD or a variant thereof.

Disclosed are methods of treating bone loss in a subject comprising administering to the subject a therapeutically effective amount of bPTH7-34DD or a variant thereof.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 18A-18E show the X-ray representatives of mice transplanted with MDA-MB-231 cells to the left tibia. Lytic lesions were seen on the left tibiae (A, B and high magnification C, D, see arrows), compared to treated mice with no lytic lesions (E)

DETAILED DESCRIPTION

Figure 1:
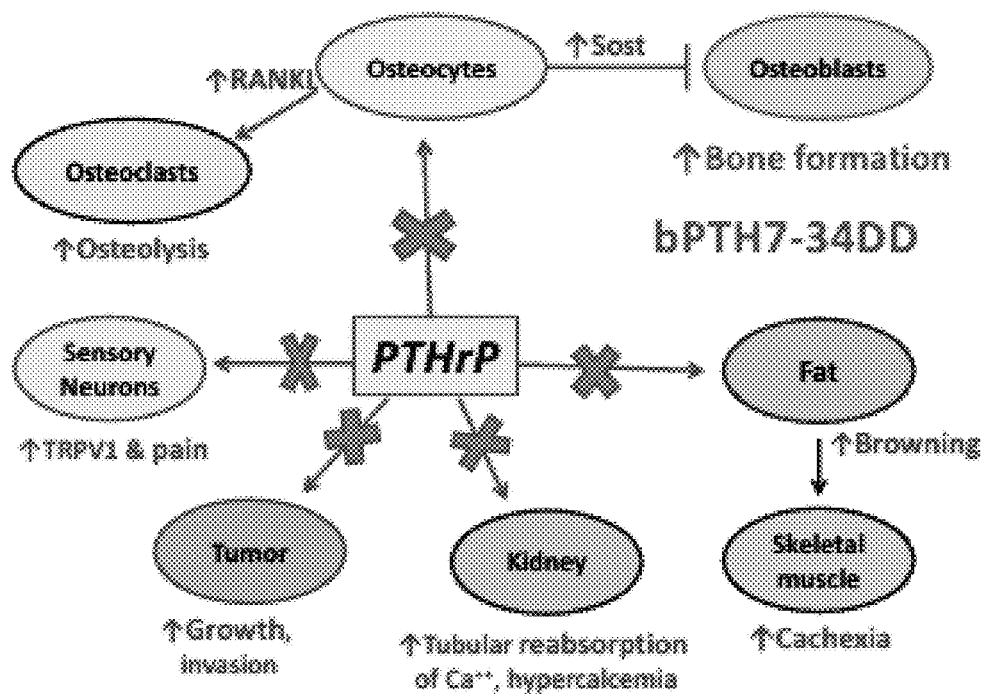
FIG. 1 is a cartoon of the systemic responses to continuous PTHrP (lines) blocked by bPTH7-34DD (X).

The disclosed method and compositions may be understood more readily by reference to the following detailed description of particular embodiments and the Examples included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the amino acids are discussed, each and every combination and permutation of the peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

The word "or" as used herein means any one member of a particular list and also includes any combination of members of that list.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered. Subject can be used interchangeably with "individual" or "patient".

As used herein, the term "patient" refers to a subject afflicted with a disease or disorder. The term "patient" includes human and veterinary subjects. In some aspects of the disclosed methods, the "patient" has been diagnosed with a need for treatment, such as, for example, prior to the administering step.

As used herein, the term "comprising" can include the aspects "consisting of" and "consisting essentially of".

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; and Y, tyrosine.

As used herein the terms "amino acid" and "amino acid identity" refers to one of the 20 naturally occurring amino acids or any non-natural analogues that may be in any of the antibodies, variants, or fragments disclosed. "Amino acid" as used herein means both naturally occurring and synthetic amino acids. For example, homophenylalanine, citrulline and norleucine are considered amino acids for the purposes of the invention. "Amino acid" also includes imino acid residues such as proline and hydroxyproline. The side chain may be in either the (R) or the (S) configuration. In an aspect, the amino acids are in the (S) or L-configuration. If non-naturally occurring side chains are used, non-amino acid substituents may be used, for example to prevent or retard in vivo degradation.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

The term "fragment" can refer to a portion (e.g., at least 4, 5, 6, 7, 8, 9, 10, 11, 12, 13, 14, 15, 16, 17, etc. amino acids) of a peptide that is substantially identical to a reference peptide and retains the biological activity of the reference. In some aspects, the fragment or portion retains at least 50%, 75%, 80%, 85%, 90%, 95% or 99% of the biological activity of the reference peptide described herein. Further, a fragment of a referenced peptide can be a continuous or contiguous portion of the referenced polypeptide (e.g., a fragment of a peptide that is ten amino acids long can be any 2-9 contiguous residues within that peptide).

A "variant" or "variant thereof" can mean a difference in some way from the reference sequence other than just a simple deletion of an N- and/or C-terminal amino acid residue or residues. Where the variant includes a substitution of an amino acid residue, the substitution can be considered conservative or non-conservative. Conservative substitutions are those within the following groups: Ser, Thr, and Cys; Leu, ILe, and Val; Glu and Asp; Lys and Arg; Phe, Tyr, and Trp; and Gln, Asn, Glu, Asp, and His. Variants can include at least one substitution and/or at least one addition, there may also be at least one deletion. Variants can also include one or more non-naturally occurring residues. For example, they may include selenocysteine (e.g., seleno-L-cysteine) at any position, including in the place of cysteine. Many other "unnatural" amino acid substitutes are known in the art and are available from commercial sources. Examples of non-naturally occurring amino acids include D-amino acids, amino acid residues having an acetylaminomethyl group attached to a sulfur atom of a cysteine, a pegylated amino acid, and omega amino acids of the formula $NH_2(CH_2)_nCOOH$ wherein n is 2-6 neutral, nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties of proline.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Methods

Disclosed are methods of decreasing cancer growth in the bones in a subject having cancer bone metastasis or preventing bone metastasis in a subject with a local cancer comprising administering to the subject a therapeutically effective amount of bPTH7-34DD or a variant thereof.

Disclosed are methods of decreasing bone destruction in a subject comprising administering to the subject a therapeutically effective amount of bPTH7-34DD or a variant thereof. In some aspects, the bone destruction is caused by cancer cells that colonize the bone.

Disclosed are methods of decreasing cachexia in a subject comprising administering to the subject a therapeutically effective amount of bPTH7-34DD or a variant thereof.

Disclosed are methods of treating osteoporosis in a subject comprising administering to the subject a therapeutically effective amount of bPTH7-34DD or a variant thereof.

Disclosed are methods of ameliorating one or more symptoms or side effects cancer bone metastasis comprising administering to the subject a therapeutically effective amount of bPTH7-34DD or a variant thereof. In some aspects, the one or more symptoms or side effects cancer bone metastasis can be an increase in tumor growth, a loss of skeletal muscle, or bone destruction. Other symptoms or side effects cancer bone metastasis can include, but are not limited to, cancer bone pain, hypercalcemia of malignancy, excessive weight loss due to excessive fat loss in addition to muscle loss. In some aspects, the cancer bone metastasis can be, but is not limited to, metastasis of breast or prostate cancer.

Disclosed are methods of treating bone loss in a subject comprising administering to the subject a therapeutically effective amount of bPTH7-34DD or a variant thereof.

In some aspects of the disclosed methods, the bPTH7-34DD, also referred to as "[D-Trp12, Tyr34]-bovine PTH (7-34)" is a bovine biased agonist of PTH1R. bPTH7-34DD contains the bovine PTH sequence from amino acids 7-34 and has been altered to contain two unnatural D-amino acids. bPTH7-34DD differs from human PTH not only in the presence of the two D-amino acids but also in that bPTH7-34DD contains a Phe at position 7 of PTH (or position 1 of bPTH7-34DD) and a Ser at position 16 of PTH (or position 10 of bPTH7-34DD). The human sequence contains a Leu at position 7 of PTH (or position 1 of hPTH7-34) and an Asn at position 16 of PTH (or position 10 of hPTH7-34). The amino acid sequence for bPTH7-34DD is Phe-Met-His-Asn-Leu-(D)Trp-Lys-His-Leu-Ser-Ser-Met-Glu-Arg-Val-Glu-Trp-Leu-Arg-Lys-Lys-Leu-Gln-Asp-Val-His-Asn-(D)Tyr-NH2 (SEQ ID NO:1). In some aspects, a variant of bPTH7-34DD can be administered to the subject. In some aspects the variant of bPTH7-34DD comprises at least one mutation in the amino acid sequence of SEQ ID NO:1. The at least one mutation can be a conservative mutation, wherein the function of the peptide remains the same as the peptide of SEQ ID NO:1. In some aspects, all of the amino acids of bPTH7-34DD or a variant thereof are naturally occurring L enantiomers except for D-tryptophan at position 6 and D-tyrosine at position 28 of SEQ ID NO:1 (corresponding to positions 12 and 34 of naturally occurring mature PTH or PTHrP). In some aspects, the variant of bPTH7-34DD comprises at least on mutation when compared to SEQ ID NO: 1, wherein the at least one mutation can be D-Phe instead of D-Tyr at position 28 of SEQ ID NO:1 (which is position 34 of bPTH). In some aspects, the variant of bPTH7-34DD comprises at least on mutation when compared to SEQ ID NO: 1, wherein the at least one mutation is not a lysine for the phenylalanine at position 1 of SEQ ID NO:1 (which is position 7 of bPTH). In some aspects, the variant of bPTH7-34DD comprises at least on mutation when compared to SEQ ID NO: 1, wherein the at least one mutation is not an asparagine for the phenylalanine at position 1 of SEQ ID NO:1 (which is position 7 of bPTH.

In some aspects, the bPTH7-34DD can be modified wherein the (D)Trp is present but the (D)Tyr has been modified to produce a variant of bPTH7-34DD. The modified (D)Tyr can be a natural amino acid, however, the (D)Trp must be present. In some aspects, any of the amino acids besides (D)Trp can be substituted with a conservative amino acid substitution.

In some aspects, mature, secreted PTH and PTHrP share sequence identity of 70% across their first 13 amino acids and share the same PTH1R receptor. Productive binding to the receptor involves approximately the first 34 amino acids of either PTH or PTHrP. Peptides covering amino acids 7-34 lack about half of the PTH/PTHrP identity region but maintain some receptor binding affinity. In some aspects, PTH and PTHrP can form intramolecular hairpin structures in which N- and C-terminal regions interact, placing differing sequence constraints on PTH vs PTHrP. In some aspects, the 28 amino acid peptide bPTH7-34DD contains four classes of amino acid residues: 1) Invariant residues $K^{12}$, $R^{20}$, $L^{24}$, and $H^{32}$, which are identical in bovine and human PTH and PTHrP (whose sequence is identical between bovine and human); 2) Unique: three residues required for the biased ligand activity to increase β-arrestin signaling without activating cAMP: $F^7$, $D-W^{12}$, and $S^{16}$; 3) Protective against proteolysis: the C-terminal $D-Y^{34}$, which replaces $F^{34}$, and could be substitutable with other residues, particularly other D-amino acids, to resist degradative inactivation in the bloodstream by peptidases; and 4) Conserved in PTH: the remaining 20 residues are identical between human and bovine PTHs. In some aspects these could be replaced by similar or dissimilar amino acids.

In some aspects of the disclosed methods, the subject has cancer. In some aspects, the cancer can be bone cancer. The bone cancer can have metastasized from, but is not limited to, lung cancer, prostate cancer, kidney cancer, breast cancer, multiple myeloma, renal cancers, endometrial cancers, pancreatic cancers, gastric cancers, thyroid cancers, squamous cell carcinomas (such as those of the liver and head & neck cancers), B-cell lymphomas, T-cell leukemias and lymphomas, cholangiocarcinomas, pheochromocytomas, neuroendocrine tumors (such as those of the pancreas), Leydig tumors, and thymic adenocarcinomas, blood cancer that originates in the bone marrow. In some aspects, the subject can have cancer that metastasized to the bones or is at high risk to metastasize to the bones. blood cancer that originates in the bone marrow In some aspects of the disclosed methods, the therapeutically effective amount of bPTH7-34DD or variant thereof can be 40-1000 µg/kg/d. In some aspects, the therapeutically effective amount of bPTH7-34DD or variant thereof can be between 20-100 µg/kg/d. At the bone metastasis site, a higher level of bPTH7-34DD can be administered to overcome the high PTHrP level. In some aspects, a dose as high as 1000 µg/kg/d can be delivered via subcutaneous infusion pump.

In some aspects of the disclosed methods, the therapeutically effective amount of bPTH7-34DD or variant thereof is administered subcutaneously, intramuscularly, intravenously, or as an oil based depot injection. In some aspects, bPTH7-34DD or variant thereof is administered in a continuous administration. In some aspects, continuous administration can continue until the tumor is non-detectable or thereafter to prevent tumor recurrence and increase new bone formation. In some aspects, a continuous-release formulation of bPTH7-34DD or variant thereof can be administered. Thus, in some aspects, although the administration can be subcutaneous or intramuscular, the release of the bPTH7-34DD or variant thereof can be continuous. The administration can comprise a depot injection, implantation, or intermittent intravenous administration.

In some aspects of the disclosed methods, the bPTH7-34DD or variant thereof blocks parathyroid hormone-related protein (PTHrP). Thus, in some aspects, a bPTH7-34DD or variant thereof with at least one mutation in SEQ ID NO:1 retains the ability to block parathyroid hormone-related protein (PTHrP).

In some aspects of the disclosed methods, wherein the bPTH7-34DD or variant thereof inhibits white to brown adipocyte conversion.

In some aspects of the disclosed methods, the administration of a therapeutically effective amount of bPTH7-34DD or variant thereof decreases tumor growth in the subject. A decrease in tumor growth can be a regression of tumor size, a halt to further tumor growth, or a slower rate of tumor growth than was achieved prior to administration of bPTH7-34DD or variant thereof.

In some aspects of the disclosed methods, the administration of a therapeutically effective amount of bPTH7-34DD or variant thereof deceases bone destruction in the subject compared to the level of bone destruction in the absence of the administration to the subject. In some aspects, bone destruction can be measured by changes in clinical serum markers of bone destruction (such as CTX), changes in bone mineral density by DEXA, or X-ray or micro QCT detection of metastatic osteolytic lesions, or changes in osteoclast activation by TRAP immunohistothermical staining of the tibiae.

In some aspects of the disclosed methods, the administration of a therapeutically effective amount of bPTH7-34DD or variant thereof improves bone formation in the subject. In some aspects, improved bone formation can be determined by measuring blood level of bone formation markers (e.g. alkaline phosphatase and P1NP (total procollagen type 1 N-terminal propeptide)).

In some aspects of the disclosed methods, the administration of a therapeutically effective amount of bPTH7-34DD or variant thereof does not cause hypercalecemia and can treat hypercalcemia that is refractory to conventional treatment.

1. Combination Treatment

Disclosed herein are combination therapies. In some aspects of the disclosed methods, the methods further comprise administering a second therapeutic to the subject. In these instances, the first therapeutic is the bPTH7-34DD or variant thereof.

In some aspects, the second therapeutic can be a bone anabolic treatment. In some aspects, the second therapeutic can be a known anti-cancer treatment. Other examples of a second therapeutic include, but are not limited to, pain relievers, immunomodulatory agents (including but not limited to thalidomide, lenalidomide and pomalidomide), proteasome inhibitors (including but not limited to bortezomib, carfilzomib and ixazomib), corticosteroid, alkylators (including but not limited to melphalan, doxorubicin, cyclophosphamide and bendamustine), antimicrotuluar agent (taxanes and vincaalkaloids), hormonal therapy radiation, and bisphosphonates.

2. Administration of bPTH7-34DD as a Pharmaceutical Composition

Disclosed are methods comprising the administration of compositions comprising any of the disclosed peptides.

In some instances, the disclosed methods comprise the administration of compositions furthering comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

The disclosed peptides can be formulated and/or administered in or with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug (e.g. peptide) in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Thus, the compositions disclosed herein can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subject's lung cells. Regarding liposomes, see, e.g., Brigham et al. Am. J. Resp. Cell. Mol. Biol. 1:95 100 (1989); Felgner et al. Proc. Natl. Acad. Sci USA 84:7413 7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In some instances, disclosed are pharmaceutical compositions comprising any of the disclosed peptides described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides described herein and can also include a carrier such as a pharmaceutically acceptable carrier. For example, disclosed are pharmaceutical compositions, comprising the peptides disclosed herein, and a pharmaceutically acceptable carrier. In one aspect, disclosed are pharmaceutical compositions comprising the disclosed peptides. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for nasal, oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In practice, the peptides described herein, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

By "pharmaceutically acceptable" is meant a material or carrier that would be selected to minimize any degradation of the active ingredient and to minimize any adverse side effects in the subject, as would be well known to one of skill in the art. The peptides described herein, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A.R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also, co-solvents such as alcohols can be used and may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Because of the ease in administration, oral administration can be used, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a disclosed peptide (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. Typically, the final injectable form should be sterile and should be effectively fluid for easy syringability. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Formulations for optical administration may include ointments, lotions, creams, gels, drops, suppositories, sprays, liquids and powders. Conventional pharmaceutical carriers, aqueous, powder or oily bases, thickeners and the like may be desirable.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a disclosed peptide, and/or pharmaceutically acceptable salts thereof, can also be prepared in powder or liquid concentrate form.

The exact dosage and frequency of administration depends on the particular disclosed peptide, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

EXAMPLES

A. Example 1

1. Background

Most tumors that grow in bone cause osteolytic bone destruction and high bone turnover due to tumor secretion of parathyroid hormone-related protein (PTHrP) which stimulates bone cell production of RANK ligand that in turn increases osteoclast formation, activity and survival. A similar mechanism may occur in the bone destruction caused by multiple myeloma, MM [Cafforio et al, 2014]. PTHrP was first discovered as the causal factor of humoral hypercalcemia of malignancy (HHM)—by increasing osteoclastic resorption and tubular reabsorption of calcium [Suva et al, 1987; Clines, 2011]. HHM can be decreased by inhibitors of osteoclastic bone destruction, such as bisphosphonates, but they are not always effective and do not restore lost bone [Hu et al, 2014; Diehl et al, 2015], which occurs in many cancer patients, due to tumor and anti-tumor treatments, such as sex-steroid inhibitors in breast and prostate cancer. PTHrP plays a multifunctional role in bone metastases [Soki et al, 2012]. Guise et al [1996] first showed that it drove osteoclastic bone metastases, due to local actions of PTHrP in bone in the absence of sufficient systemic protein to cause HHM. TGFβ, released from bone matrix during resorption, stimulated breast cancer production of PTHrP [Yin et al, 1999], fueling a vicious cycle of bone metastases of which PTHrP is the central driver [Chirgwin & Guise, 2000; Kakonen et al, 2002], by its activation of RANKL expression.

Bone-anabolic treatment not only improves bone health and quality of life but can also reduce skeletal-related events, including bone pain, hypercalcemia and cachexia in cancer patients. Stimulation of bone formation can also have direct anti-tumor actions, as has been found in MM [Penisi et al, 2010; Yaccoby, 2010] and breast cancer [Swami et al, 2017]—as previously suggested [Suvannasankha & Chirgwin, 2014]. FDA-approved anabolic treatments for bone loss include teriparatide (Forteo, hPTH1-34) and abaloparatide (Tymlos, a synthetic PTHrP analog with multiple amino acid changes). Both carry a black box warning against use in cancer patients. PTH & PTHrP act through the same receptor, PTH1R, a 7-transmembrane domain, G protein-coupled receptor (GPCR). It has been a puzzle how activation of the same receptor in bone can cause both bone formation and bone destruction [Hock & Gera, 1992]. Pulsatile activation (once-daily injection of PTH) is anabolic, particularly for trabecular bone, while continuous infusion (or PTHrP secretion by tumor) is catabolic. PTH1R couples to a variety of signaling pathways including several G proteins and β-arrestin, enabling the development of PTH and PTHrP analogs with biased actions that favor anabolic vs catabolic responses [Lutrell et al, 2015]. Anabolic PTH treatment decreases bone metastases in mouse breast cancer xenograft models [Swami et al, 2017], a response previously seen with MM [Pennisi et al, 2010].

PTHrP contributes to cancer cachexia, a systemic wasting of skeletal muscle [Sato et al, 2003]. PTH1R stimulation stimulates reprogramming of white adipocytes into thermogenic beige and brown fat cells, which systemically activates skeletal muscle catabolism [Kir et al, 2014; 2016] by secretion of pro-cachectic factors that may include adiponectin [Zhang et al, 2017]. Additionally, pulsatile and continuous activation of the receptor have opposite effects on bone marrow stromal adipogenesis, with the former inhibiting it, while the latter stimulates it [Rickard et al, 2009]. The PTH1R plays a central role in the differentiation of adipocytes and osteoblasts in bone marrow [Fan et al, 2017]. PTHrP also potentiates cancer bone pain by upregulated the TRPV1 calcium channel in sensory neurons [Mickle et al, 2015; Shepherd et al, 2018]. It also affects, along with TGFβ and bisphosphonates, T cell responses to tumor in bone [Fournier et al, 2006].

i. PTH1R

The receptor is widely expressed in bone where it is seen by IHC abundantly on osteoblasts and osteocytes but not osteoclasts [Lupp et al, 2010]. Functional experiments report PTH1R activity in isolated osteoclasts, which respond to PTH [Langub & Malluche, 2002; Dempster et al, 2005], although the receptor may be nuclear [Faucheux et al, 2002]. Cancers and cell lines that cause bone metastases, including MDA-MB-231 & MCF7 breast and PC-3 & LNCaP prostate lines, express PTH1R [Birch et al, 1995; Canon et al, 1997; Downey et al, 1997; Iezzoni et al, 1998; Gonzalez et al, 2017]. PTHrP is an autocrine growth enhancer of MCF7 BC cells [Birch et al, 1995; Falzon & Du, 2000]. PTHrP plays an important role in breast development and lactation [Wysolmerski & Stewart, 1998]. Tumor PTHrP contributes to BC tumor initiation, progression, and metastases not limited to bone [Li et al, 2006]. It also contributes to prostate cancer bone metastases, where osteoclastic resorption is elevated despite net osteosclerotic bone responses [Liao et al, 2008].

Figure 2:
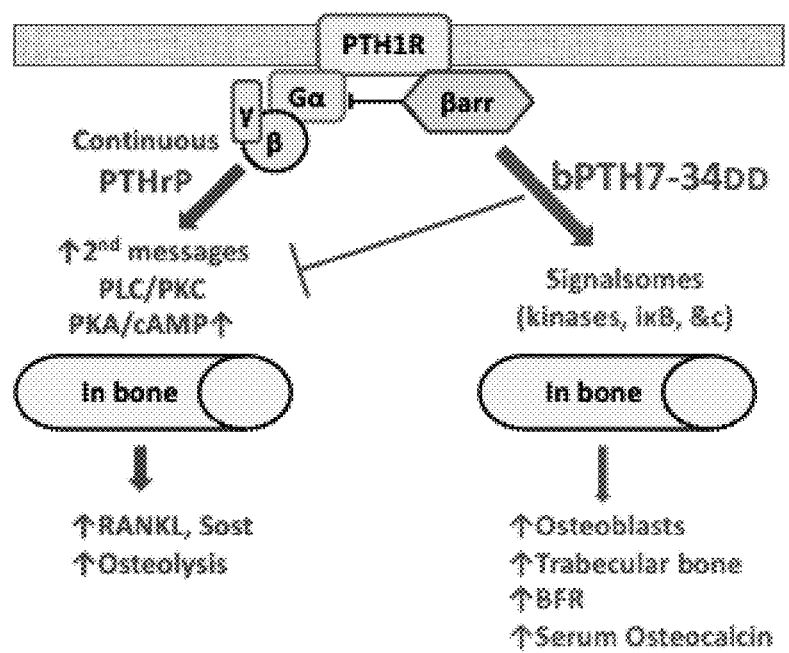
FIG. 2 is a cartoon showing the PTH1R responses to PTHrP (left hand side) vs bPTH7-34DD ligand binding (right hand side).

The 7-TMD PTH1R is a class 2 G-protein coupled receptor (GPCR) that interacts with Gs, Gq/11 and β-arrestins 2/3. GPCRs are not adequately described by a two-state on/off model but exist in a wide variety of conformational states, through which ligands can act as agonists or antagonists for each of the signaling pathways to which the receptor is coupled. By these criteria, bPTH7-34DD inhibits G-coupled signaling while activating β-arrestin signaling with Kd=25 nM [Appleton et al, 2013]. Arrestins cause desensitization of G protein-mediated signaling and receptor internalization in response to ligand. They recruit a range of signaling components to ligand-bound PTH1R: Src, ERK1/2, MAPK, E3 ubiquitin ligases, IKB, and several phosphatases and phosphodiesterases, giving rise to multiple responses in bone and other tissues [Bohinc & Gesty-Palmer, 2013; Peterson & Luttrell, 2017]. FIG. 2 schematizes the biased actions of bPTH7-34DD on PT1R to block the effects of continuous PTHrP. The unique actions of bPTH7-34DD on bone led Gesty-Palmer & Luttrell [2011] to propose the peptide as a novel anabolic agent that increases bone mass by uncoupling the anabolic effects of PTH1R activation from the catabolic and calcitropic responses caused by PTH & PTHrP. Specifically, bPTH7-34DD expands the osteoblast pool through β-arrestin 2-dependent cell cycle regulation and anti-apoptotic actions, while uncoupling the PTH1 receptor from Gs-cAMP-dependent activation.

ii. PTHrP/PTH1R, Cancer & Bone Metastases

Mouse & human PTHrPs are almost identical, with similar 36aa prepro regions, while the mature peptides differ only at aa 49 (A/S) and 99 (R/K) and then diverge beyond aa 114. The amino terminal region 1-34 contains the known determinants for binding to the PTH1R. Similarly, PTH1-34 carries the determinants for receptor binding. PTH and PTHrP share modest homology across this short region, limited to the identity of 8 of the first 13 residues, full-length PTH & PTHrP proteins are 84 and 139-173 aa, respectively, and otherwise entirely divergent. Small molecule ligands for the PTH1R that are effective inhibitors compared to existing peptides have not been found. PTHrP is widely expressed by breast and prostate cancers, but also by other tumor types that metastasize to bone. Among breast cancers human MDA-MB-231 and MCF7 both show autocrine responses to PTHrP [Zheng et al, 2013; Falzon & Du, 2000]. PTHrP protein secretion was found by MDA-MB-231, -361, -435s, and -436, BT549 and HS578T, while ZR-75-1, T47D and an osteoblastic variant of MCF7 were negative. Three of three tested prostate cancer lines were positive: DU145, LNCaP (low), and PC-3 (high). Most of the lines secreted amounts similar to MDA-MB-231 cells, the best characterized bone metastatic model [Yin et al, 1999, Table 2]. The expression by prostate cancer cell lines confirmed a previous report [Wu et al, 1998]. A variety of lung cancer cell lines express PTHrP and cause bone metastases: SBC-5, HARA, NCI-H292, and A549, and renal carcinomas, melanoma and squamous cell head & neck cancers do as well. A number express sufficient PTHrP to cause HEM when not in bone, including HARA & RWGT2. Among mouse breast cancer lines, 4T1 BALB/c and Eo771 C57BL6 cells make PTHrP and cause osteolytic lesions. Cachexia has been reported in a number of these animal models.

Actions of PTHrP on adipocytes and cachexia: Studies by the Ogata laboratory on tumor cachexia failed to find a direct action of PTHrP on skeletal muscle [Sato et al, 2003], suggesting an indirect effect, which was clarified when Spiegelman's laboratory showed that PTHrP stimulated switching of adipocytes from white to beige/brown. The latter cells express uncoupling protein 1 (UCP1) and secrete unknown factors into the circulation that cause wasting of skeletal muscle [Kir et al, 2014, 2016]. Additional factors in the metastatic tumor microenvironment also increase adipocyte browning and cachexia, in particular adrenergic ligands [Brooks et al, 1981], which are known to increase breast cancer bone metastases [Elefteriou, 2016]. Both the (3-adrenergic receptor and PTH1R stimulate cAMP and couple to β-arrestins. It is unknown if their co-regulation seen in osteoblasts [Fukuyama et al, 1997] occurs in adipocytes. Cancer bone pain could release sufficient local adrenaline/noradrenaline significantly adipocyte browning and cachexia. If these mechanisms were important, PTHrP would be central to a vicious cycle worthy of Ezekiel, with PTHrP stimulating pain to increase (nor)adrenaline, then both PTH1R and adrenergic signaling increasing browning or BMAT and cachexia. These steps should be blocked by bPTH7-34DD, although additional effects via β-arrestin are unpredictable. The βarr-coupled calcium sensing receptor CaSR could further contribute to bone metastases and BMAT changes [Kim et al, 2016; Boudot et al, 2017; Bravo-Sagua et al, 2017].

bPTH7-34DD-[D-Trp12,Tyr34]-bovine-PTH(7-34)— was first described as a simple PTH antagonist in which the D-amino acid substitutions were expected to increase binding to the receptor and stability in vivo [Goldman et al, 1988; Chorev et al, 1990]. The peptide was included in a patent issued to Merck [Chorev & Rosenblatt, 1990] and now expired. Four years later Kukrej a et al [1994] tested bPTH7-34DD in a mouse model of HEIM in which nude mice bearing a human squamous cell xenograft developed hypercalcemia (serum Ca++=17 mg/dl). These animals were treated by i.v. infusion of peptides, with a 100 μg bolus followed by 25 μg/hr for 6 hrs and monitoring of serum Ca++. These experiments were undertaken prior to the understanding of the PTH1R mechanisms of action and were too short-term to detect responses to a dose of peptide 1000× higher than that administered over 24 hrs to mice [Gesty-Palmer et al, 2009], which responded to a one month treatment with significant new bone formation The massive acute dose of bPTH7-34DD failed to reduce Ca++ serum below 12 mg/dl, with detected reductions largely due to rehydration from the infusion. Gardella et al. [1996] subsequently showed that the peptide was an inverse agonist of G-coupled cAMP formation, with an IC50 of 50 nM. Gesty-Palmer et al [2006] found that it caused G protein-independent/β-arrestin-dependent ERK1/2 activation, identifying bPTH7-34DD as a biased agonist [Gesty-Palmer & Luttrell, 2011; Bohinc & Gesty-Palmer, 2012]. It inhibits rather than activates the GPCR signaling pathways (which increase cAMP), while continuing to activate the β-arrestin pathway controlled by PTH1R. The analog has now been tested in mice by chronic infusion via Alzet minipump, resulting in increased bone formation and bone mineral density without hypercalcemia or increased markers of osteolysis [Maudsley et al, 2015]. bPTH7-34DD thus stimulates bone anabolic responses, without hypercalcemia, while competitively inhibiting PTHrP binding to its receptor. The anabolic response profile of osteoblasts treated with bPTH7-34DD is fundamentally different and non-overlapping with that of Obls treated with hPTH1-34, giving the peptide an entirely different set of responses compared to teriparatide [Luttrell et al, 2018].

The role of β-arrestins in adipocytes remains largely uninvestigated, although k/d of β-Arr 1 or 2 enhanced insulin-dependent differentiation of 3T3-L1 cells, with increased expression of C/EBPα, C/EBPβ, C/EBPδ, and PPARγ, while decreasing differentiation in response to ghrelin and its target genes downstream of AKT [Santos-Zas et al, 2013]. It is possible that treatment of marrow adipocytes with bPTH7-34DD could stimulate anti-tumor secretory activity of fat cells or alter adipogenic vs osteogenic differentiation of marrow precursors [Falank et al, 2017; Fan et al, 2017]. The role of β-arrestins in osteoclasts is also largely uninvestigated. Studies with βArr2−/− bones and cells suggest that β-Arr2 activity suppresses osteoclasts. Some of this suppression is due to decreased RANKL expression from cells of the osteoblastic lineage, but there may be effects within osteoclasts via ephrin signaling [Pierroz et al, 2009], and βArr2 regulates trafficking of TRAF6 [Xiao et al, 2015]. β-arrestins in osteoblasts are better understood. When Gesty-Palmer et al [2013] studied calvarial osteoblasts from mice treated with hPTH1-34 or bPTH7-34DD from wt or βArr2−/− bones, they observed that anabolic markers of Obl activity (RUNX2, Alk Phos, Col1A1) were strongly increased by hPTH1-34 but not bPTH7-34DD, which significantly increased only Alk Phos & Col1A1 ~2×. The induction of RANKL was similarly decreased with bPTH7-34DD. Instead, the primary effects of bPTH7-34DD in vivo were on cell cycle, survival/apoptosis and migration, although the histomorphometric parameters for bone-anabolic responses were similar between mice treated with hPTH1-34 vs bPTH7-34DD. The latter peptide specifically down-regulated ~2× the mRNA for cyclin-dependent kinase inhibitor 1A (CDKN1A), which should increase Obl proliferation.

When mice were treated for 4 or 8 weeks with hPTH1-34 or bPTH7-34DD [Gesty-Palmer et al, 2009, 2013; Luttrell et al, 2018], tibial trabecular bone parameters were increased by both (BV/TV, trabecular number), while cortical bone parameters (periosteal circumference and cortical thickness) were increased only by hPTH1-34. Mineral apposition (MAR, BFR) was equivalently increased by both peptide treatments. By quantitative histomorphometry, osteoblast number and osteoid surface were increased by both, while osteoclast numbers were increased only by hPTH1-34. Serum osteocalcin was equivalently raised by both treatments, while urinary DPD & Ca were unaffected by bPTH7-34DD. Responses to bPTH7-34DD but not hPTH1-34 were lost in β-Arr2−/− mice. These experiments compared once-daily injection of the two peptides. Similar experiments using Alzet minipumps to deliver the peptide continuously showed similar bone-anabolic responses [Maudsley et al, 2015]. Unlike hPTH1-34, continuous infusion of bPTH7-34DD, with both peptides administered at 40 μg/kg/d, increased trabecular bone mass without stimulating bone resorption or increasing urinary calcium excretion (which was elevated 5× by continuous hPTH1-34). Six tissues from these mice were analyzed for gene expression, with each tissue showing a different pattern of responsive genes, indicating a cell-type specific response to β-Arr2-mediated responses to PTH1R ligand binding. In bone, both peptides doubled mRNA of Gab 1, a scaffold protein whose k/o in Obls decreases trabecular bone mass, BFR and bone resorption [Weng et al, 2010]. hPTH1-34 increased, while bPTH7-34DD decreased, mRNA for Dars, aspartyl-tRNA synthetase, for which a role in bone is unknown.

Nothing is known about the function of β-arrestins in osteocytes, although the responses downstream of PTH1R: β-Arr2 to ligand binding may be similar to those seen in osteoblasts. Some of the responses found in bPTH7-34DD-treated bone cells by Gesty-Palmer et al [2013] were in Ot genes such as DMP-1 & Sost. Osteocytes secrete adenosine nucleotides that stimulate breast cancer bone metastases [Zhao et al, 2014] and extracellular nucleotides bind to the P2X7 receptor and enhance PTH1R signaling through both cAMP and βarr pathways [Kim et al, 2018]. Coupling between PTH1R and β-Arr2 is regulated by phosphorylation of the receptor, a process catalyzed by the type II TG93 receptor [Qui et al, 2010]. TG93 is increased in the bone-metastatic microenvironment due to the actions of tumor PTHrP, which increases RANKL and osteoclastic resorption. Thus, complex interactions in the microenvironment may regulate osteocyte PTH1R signaling.

Clinical Relevance: Bone metastases occur with many solid tumors, particularly those of breast & prostate, but also lung & kidney, melanoma, and the hematological malignancy multiple myeloma (MM), which colonizes the bone marrow [Casimiro et al, 2009; Marino & Roodman, 2017; Parkes et al, 2018]. The majority of patients dying from breast or prostate cancer or from MM have tumor in bone, where it is resistant to treatment and causes paraneoplastic syndromes. This clinical burden is substantial in the VA and general US patient populations. Available treatments are largely palliative, aimed at relieving the serious paraneoplastic syndromes that accompany cancer colonization of the skeleton: bone loss, fracture, spinal cord compression, systemic cachexia and severe cancer bone pain [Johnson & Suva, 2017]. These complications accompany most solid tumor types and MM. They seriously decrease quality of life for cancer patients [Milgrom et al, 2017; Tsuzuki et al, 2016; Marino & Roodman, 2017].

The preclinical data indicates that bPTH7-34DD is safe and effective against cancer effects caused via the PTH1R. Daily subcutaneous injection is the current method of delivery for the bone-anabolic peptides, teriparatide (hPTH1-34) and abaloparatide, a synthetic PTHrP1-34 analogue with 8 amino acid changes that activates the PTH1R similarly to PTH [Hattersley et al, 2016]. A transdermal abaloparatide formulation is in Phase II trials, and the delivery system could be applied to other PTH/PTHrP peptide analogs [Shirley, 2017]. bPTH7-34DD could be rapidly brought into clinical use, particularly if delivered transdermally or by slow-release depot injection.

Figures 3A, 3B:
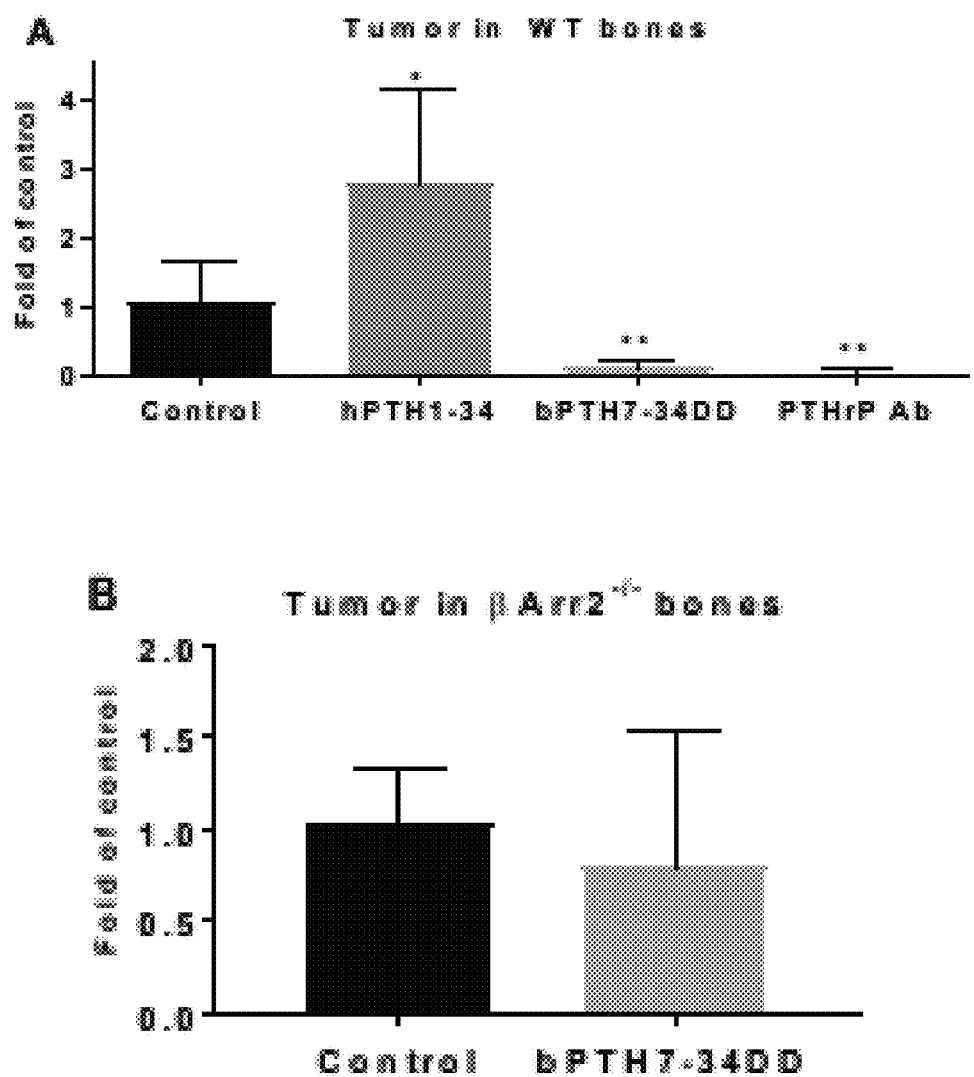
FIGS. 3A and 3B show bPTH7-34DD suppresses MDA-MB-231 growth in bone of WT type mice but not B-Arr$^{-/-}$ bone. 7D EVOCA. Tumor burden by SSQ-PCR for hRPL32.
Figure 4A:
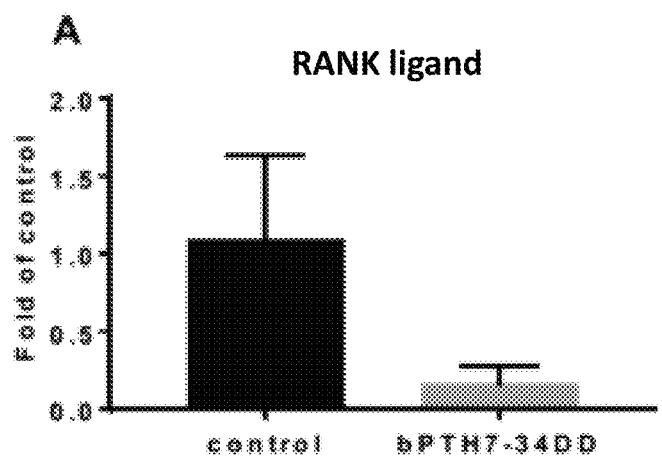
FIGS. 4A, 4B, and 4C show bPTH7-34DD decrease markers of osteolysis. 7d EVOCA MDA-MB-231+wt bones and SSQ-PCR.
Figure 4B:
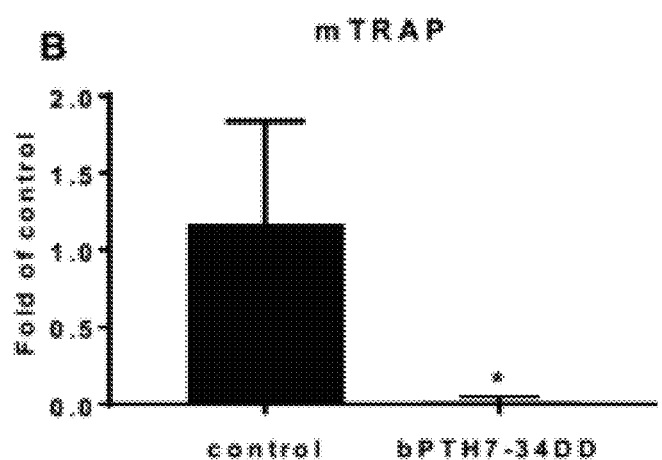
Figure 4C:
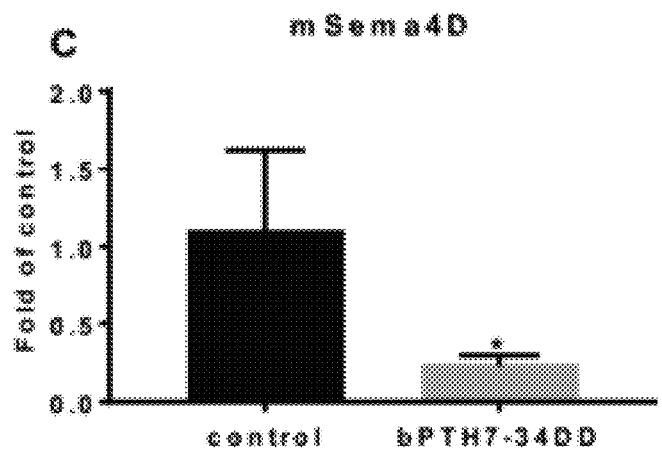
Figures 5A, 5B:
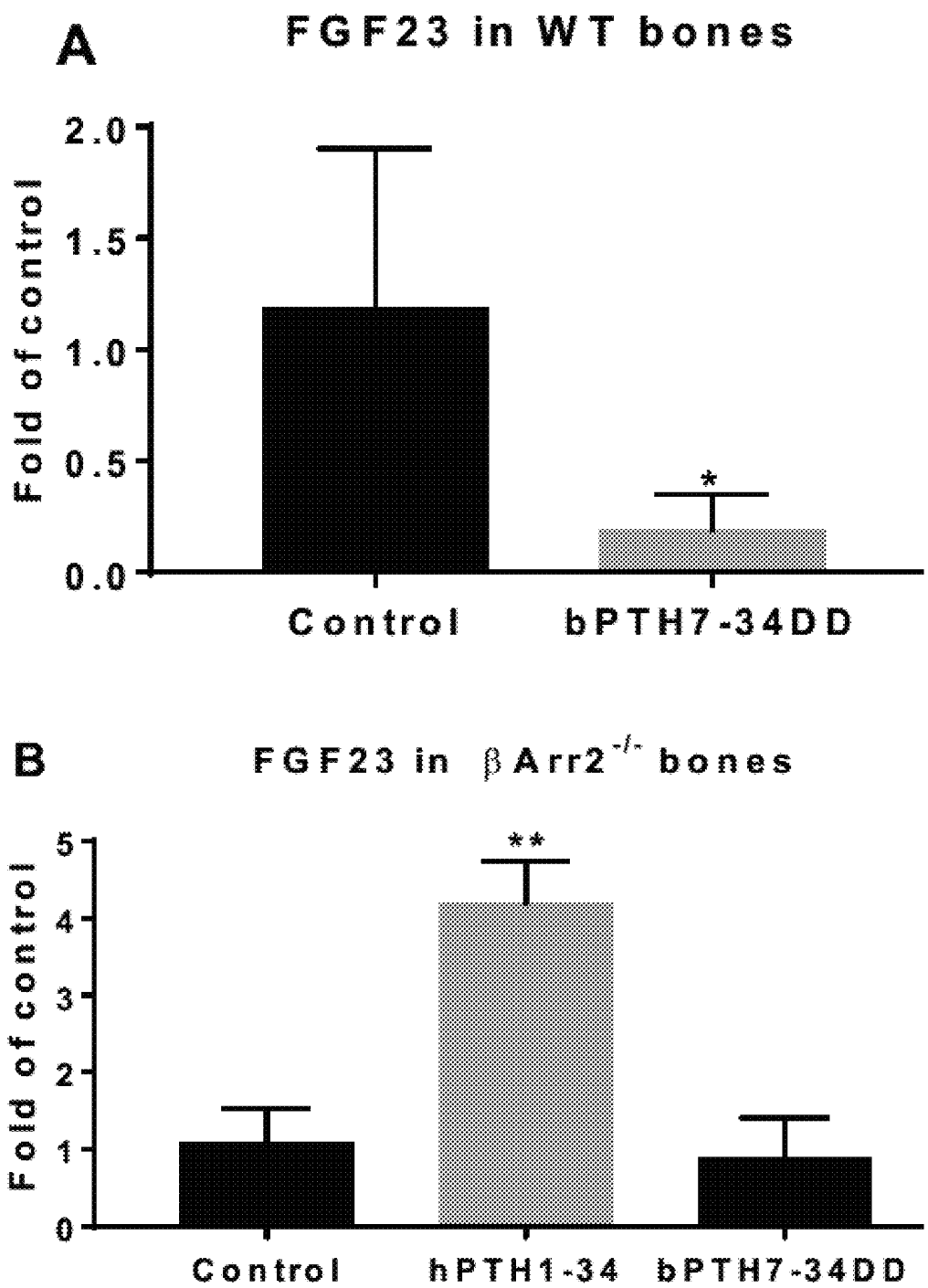
FIGS. 5A and 5B show bPTH7-34DD decreases osteocyte FGF23. 7d EVOCA with MDA-MB-231s, analyzed by SSQ-PCR.
Figures 6A, 6B:
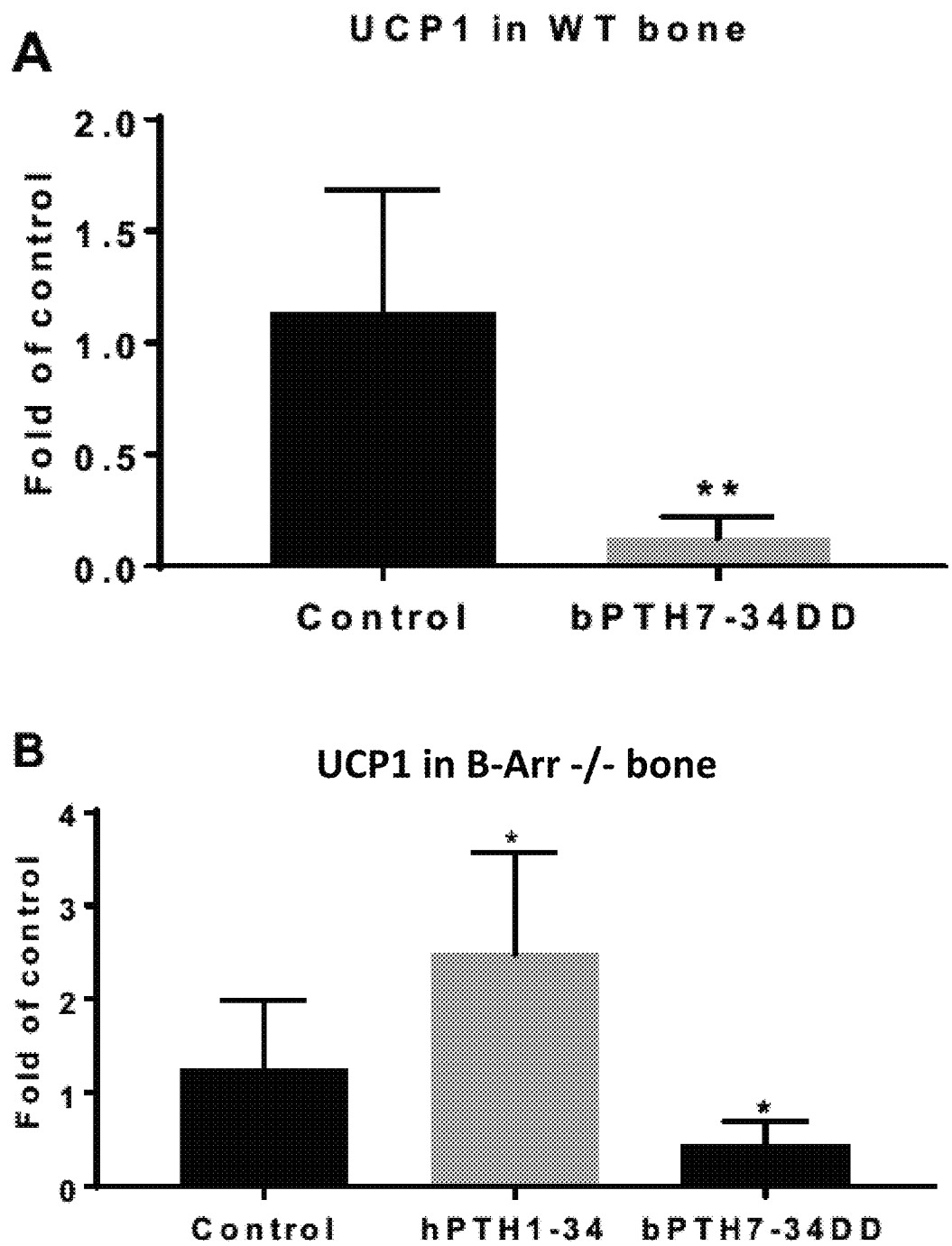
FIGS. 6A and 6B show bPTH7-34DD decrease bone adipocyte UCP1. 7d EVOCA with MDA-MB-231s as in FIGS. 5A and 5B.
Figure 7A:
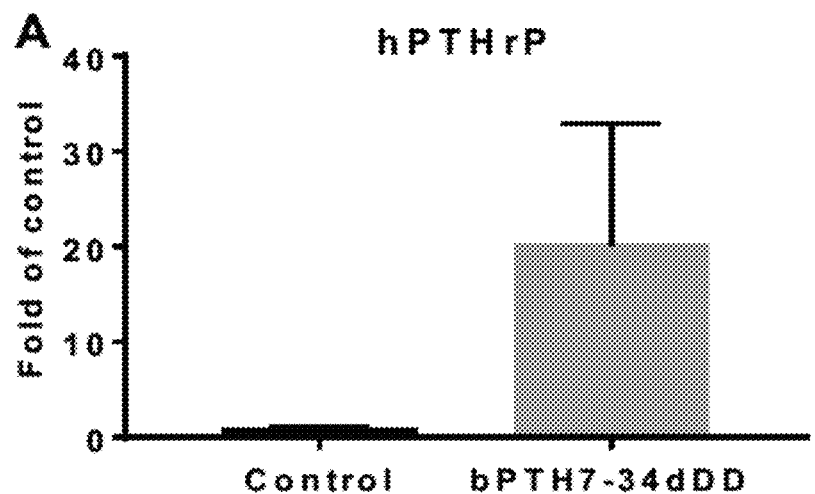
FIGS. 7A, 7B, and 7C show the effects of bPTH7-34DD on MDA-MB-231; 7d EVOCA, PCR as done in FIG. 5.
Figure 7B:
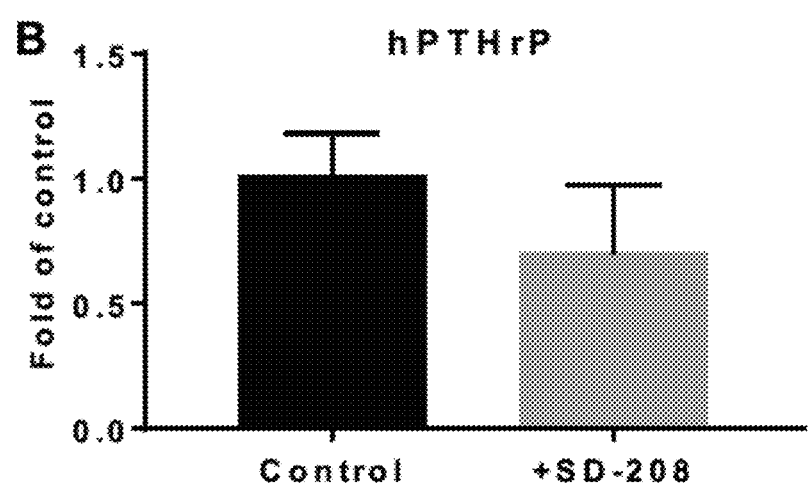
Figure 7C:
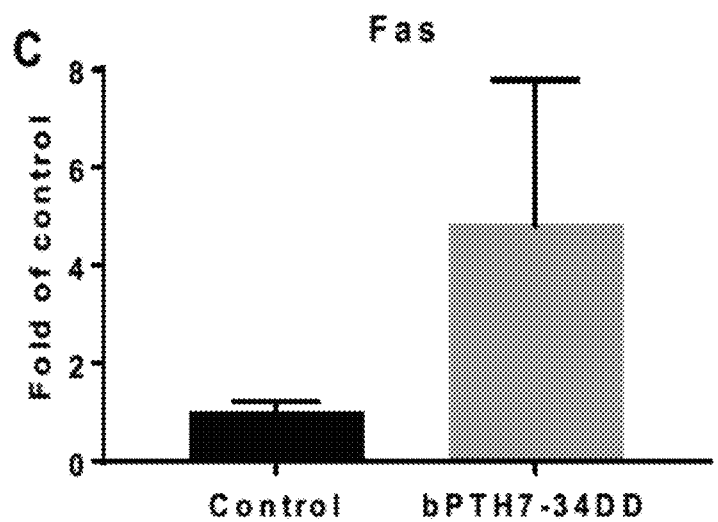
Figure 8:
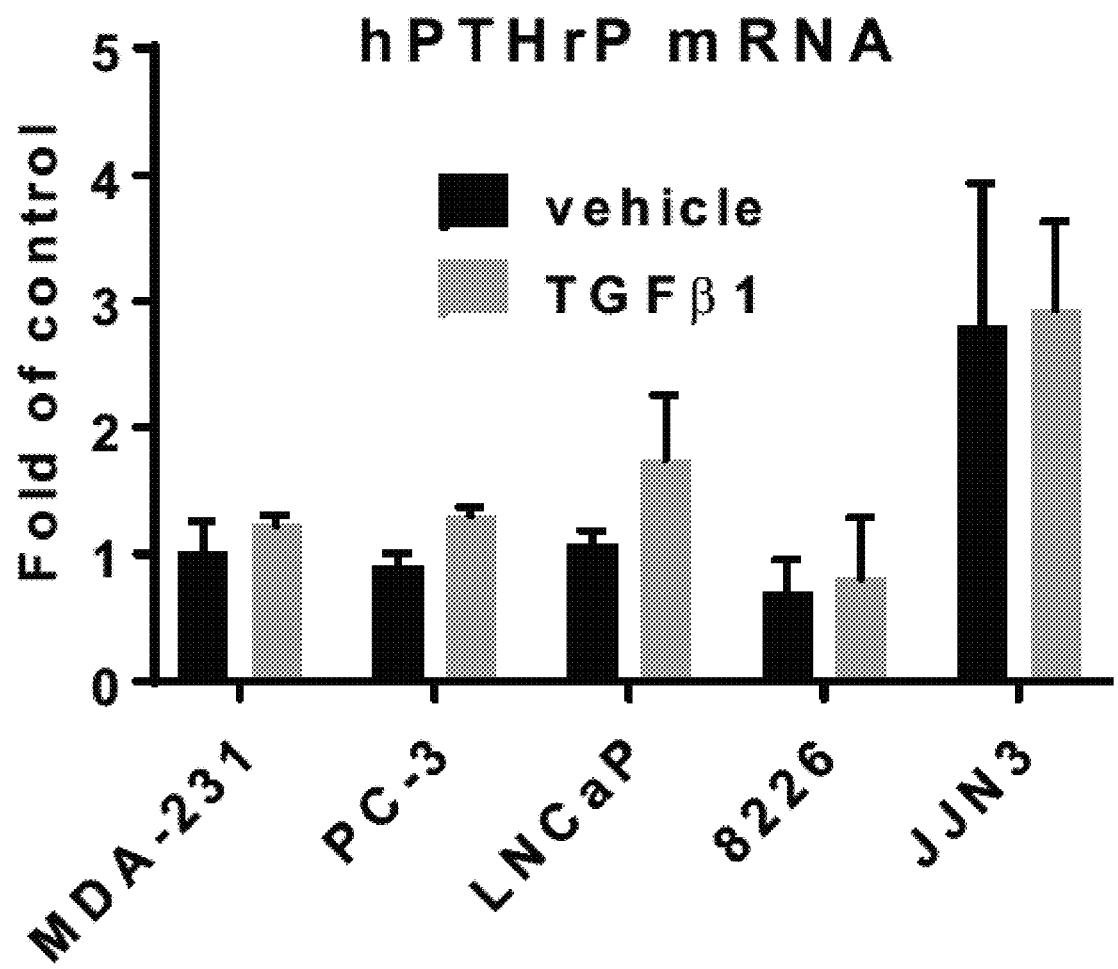
FIG. 8 shows PTHrP mRNA in MDA-231, 2 PC and 2 MM cell lines ±10 ng/ml TGFβ1 for 24 h.
Figures 9A, 9B:
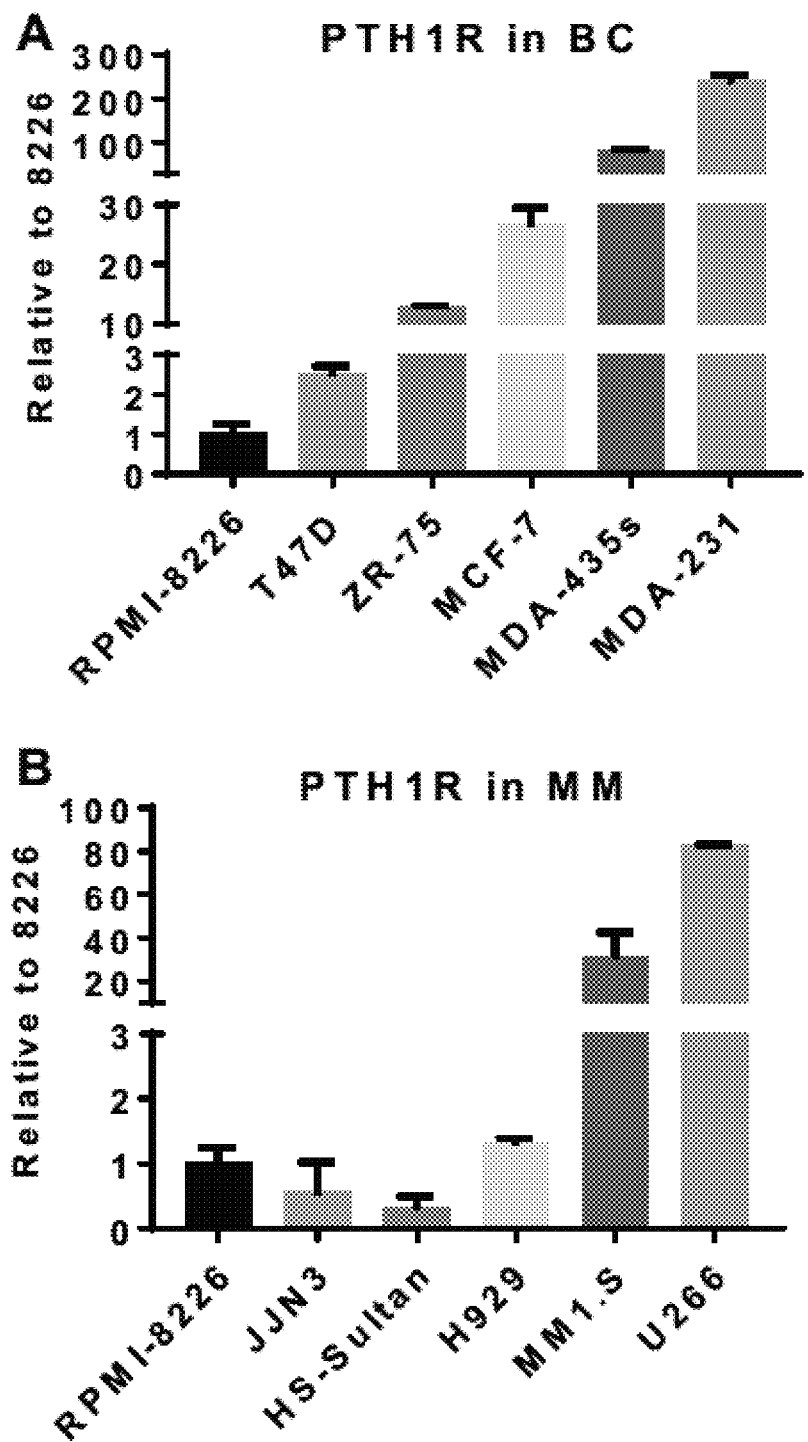
FIGS. 9A, 9B, and 9C show hPTH1R mRNA in various tumor types, normalized to 8226 myeloma (MM)=1. BC=breast cancer; PC=prostate cancer. PCR with n=3 from routine tissue culture. Primary human Obls are positive control.
Figure 9C:
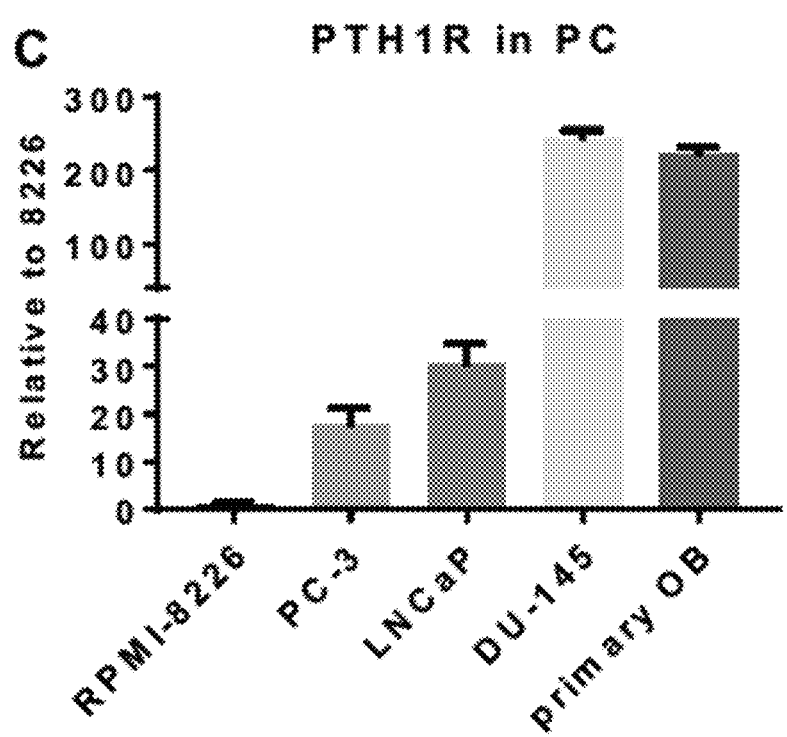

2. Results i. Data bPTH7-34DD was found to: 1) Decrease growth in bone of MDA-MB-231 breast cancer cells; 2) Decrease markers of osteolysis (RANKL, TRAP5a); 3) Increase markers of osteoblast activity (Alk Phos, Col1a1); 4) Suppress osteocyte production of RANKL & sclerostin; 5) Block conversion in bone of white to brown fat; 6) Responses were lost in bones from βarr2−/− mice using EVOCA (ex vivo organ co-culture assay of tumor+bone, a novel assay developed in the previous Merit) with BC cells. FIG. 3 shows that hPTH1-34 increased tumor growth in bone in a 7d EVOCA experiment, while growth was blocked by either bPTH7-34DD or PTHrP-neutralizing Ab. The inhibitory effect of bPTH7-34DD was lost in EVOCA with β-Arr2−/− bones (FIG. 3b). When bone genes regulated by PTHrP were analyzed by mouse-specific PCR, EVOCAs with MDA-MB-231 cells, showed significant decreases in RANK ligand, osteoclast TRAP and semaphorin 4D, which is expressed by Ocls & Ots (FIG. 4). FIG. 5 shows the effects of bPTH7-34DD on expression of the osteocyte secretory protein FGF23, which acts on tumor cells to increase production of prometastatic heparanase (unpublished data). In 7d EVOCAs with MDA-MB-231 cells, the peptide decreased FGF23 (which is increased by addition of tumor cells to bone, not shown) in wt bone (5A), while the effect was lost in β-Arr2−/− bones, while exogenous hPTH1-34 (5B, center column) was able to increase FGF23 mRNA. A parallel PCR analysis of these sample EVOCA samples was done in FIG. 6 for the adipocyte target of hPTH1R signaling, UCP1, the marker of thermogenic fat shown by Kir et al, to be a major response of WAT to BAT conversion that underlies fat secretion of unidentified factors that cause systemic muscle cachexia. Again, bPTH7-34DD blocked the UCP1 response to PTHrP+tumor and the response to the peptide, but not hPTH1-34 was blunted in EVOCAs of MDA-MB-231 cells with β-Arr 2−/− bones. FIG. 7 shows that human MDA-MB-231 BC cells in EVOCA show responses to bPTH7-34DD. The peptide increased hPTHrP (7A), perhaps by interfering with autocrine regulation of PTHrP expression, an effect not seen with the TGFβ inhibitor SD208 (7B), while the peptide increased tumor mRNA for Fas, which encodes a TNFRSF death receptor (7C). To determine the general utility of targeting PTHrP in tumor cells, a panel of human cancer cells was tested for expression of PTHrP and PTH1R. The data suggest that PTHrP is expressed by many cell types (FIG. 8). mRNA levels treatment ±10 ng/ml TGFβ treatment were determined, which had little effect, although secreted PTHrP protein needs to be analyzed. A much wider range of tumor cell messenger RNA was found for PTH1R than for PTHrP, with MM lines lower than BC or PC lines, but with high expression in all types (FIG. 9).

Thus, bPTH7-3DD can: 1) Inhibit the vicious cycle of osteolytic bone metastases by suppressing tumor growth & osteolysis; 2) Decrease cancer cachexia by blocking white-to-brown adipocyte conversion in bone; 3) Preserve bone health by stimulating new bone formation; 4) Effectively treat osteolytic tumors due breast cancer (BC), other solid tumor types, and multiple myeloma (MM).

ii. Materials

Tumor cell lines are from the ATCC wherever possible and stored as low passage primary stocks to preserve authentication; these in turn are transduced with a bicistronic lentiviral vector encoding Gaussia luciferase and GFP, plus a puromycin cassette. GFP+ cells are stored as low passage primary stocks and used for no more than 3 months. Cell lines are checked routinely for mycoplasma contamination. Breast cancer and other tumor cell lines are grown as described [Yin et al, 2003]. Standard Obl, Ocl, Ot and preadipocyte lines are available in the laboratory. hPTH7-34, bPTH7-34DD, PTHrP ELISA (S-1227) and anti-PTHrP (1-34) blocking antibody (T-4512) are from Bachem, with bPTH7-34DD purchased much less expensively at purity >98% from Lifetein (S. Plainfield, NJ). hPTHrP is from Sigma. Small molecule inhibitors are from Selleckchem. Serum Ca++ is analyzed with 96 well format kits from Quantichrom. Minipumps are from Alzet. Primary Abs against PPARγ, UCP1, CGRP & TRPV1 for IHC are from Santa Cruz.

iii. Methods

Choice of cancer cell lines: human osteolytic, triple negative breast cancer line MDA-MB-231 can be used for most of the experiments, with a small set of experiments using the aggressive mouse breast cancer cell line 4T1 in syngeneic BALB/c mice to test contributions of the immune system to PTHrP responses. MDAs are the most widely studied model of bone metastases (>400 citations). 4T1s aggressively metastasize from the mammary fat pad (MFP) to multiple organs, including lung, liver and bone and are commonly used in the intratibial injection model. The two models have been used extensively for testing anti-metastatic agents, including PTHrP-neutralizing mAb against MDA-MB-231s [Guise et al, 1996]. The breast cancer lines provide the most widely accepted preclinical models for testing bPTH7-34DD. Specific Aim 1 d will screen bPTH7-34DD for its ability to decrease tumor colonization of bone using the EVOCA assay as an efficient surrogate for animal testing, permitting future application of the peptide to other cancers in bone, including MM and prostate. Peptide treatments: General design is for four groups ex vivo, with n=4/group: a) no addition; b) 10 nM hPTHrP1-34 (PKA agonist); c) 100 nM bPTH7-34DD; 1 μM hPTH7-34 (competitive inhibitor without agonist activity). Cell proliferation can be determined with Vybrant MTT assay kits (ThermoFisher) according to the manufacturer's instructions.

EVOCA (ex vivo organ co-culture assay) of breast cancer cells and bone: Segments of neonatal mouse bone are prepared by a modification of Mohammad et al [2008]. Calvariae from euthanized 14 day old Swiss Webster pups are cut into 5 mm disks with a biopsy punch, yielding two disks (hemi-calvariae) per pup, and placed into wells of uncoated 24-well plates. Calvariae from βArr2−/− and +/+ littermates, as available, can be shipped in sterile tubes in standard tissue culture medium by overnight FedEx from the Luttrell laboratory at Medical University of South Carolina. Bones shipped overnight in media survive the shipping and give reproducible results, compared to freshly harvested bones. Cancer cells ($2-10 \times 10^3$, depending on cell types and ability to adhere to bones; e.g., 2,000 for MDA-MB-231) are added in 0.5 ml BGJb medium (Life Technologies) +10% fetal calf serum and incubated at 37° C. in 5% CO2. After 24 hours, bone disks with adhered tumor cells are transferred into 96 well plates for subsequent culture in BGJb medium changed every 2-3 days. Culture is for 7d except as indicated. At the end of the incubation, bone are either fixed and decalcified for routine histology or homogenized for RNA isolation with a bead beater, using QIAGEN RNeasy mini kits, converted to cDNA (Biorad iScript,), and analyzed by quantitative PCR using Biorad SYBR green PCR kits and a Biorad iCycler single-color real-time detection system. Ribosomal protein L32 is the normalization control. EVOCA cultures can be analyzed by histology and IHC staining. In order to visualize tumor cells, up to $5 \times 10^5$ are added.

Species-specific PCR (SSQ-PCR) primers are designed with online Primer 3 tool (http://bioinfo.ut.ee/primer3/) and tested for species-specificity with the NCBI primer design tool (http://.ncbi.nlm.nih.gov/tools/primer-blast/) by Blast searching against the targeted sequence and versus both *Mus musculus* and *Homo sapiens* sequence databases to eliminate cross-species and erroneous amplifications, and allowing amplification of transcript variants. The templates used for primer design were Genbank RefSeq files for the designated genes. Details of complete EVOCA experiments with MDA-MB-23 land primer design are in Siclari et al [2014]. Secretion of luciferase as an indicator of tumor burden [Chung et al, 2009; Tannous & Teng, 2011] is by assay of conditioned media and serum from mice, with a BioLux® Gaussia luciferase (gluc) flex assay kit from NE BioLabs and a Turner TD 20/20 luminometer. Results are expressed as relative luminescence units (RLUs).

3. Studies bPTH7-34DD

Experiments were designed to define cellular actions of bPTH7-34DD in vitro: a) Determine effects of peptide on tumor cells; b) Determine mechanism of action of bPTH7-34DD on i) Bone cells including osteoblasts (Obls), osteoclasts (Ocls), & osteocytes (Ots), and ii) Adipocytes; c) Test if responses to peptide require β-arrestin, using βarr2−/− mice; d) Test if bPTH7-34DD is effective against multiple tumor types.

i. Effects of bPTH7-34DD on Tumor Cells

Rationale: Tumor cells that cause bone metastases or osteolytic bone destruction often express the PTH1R receptor for PTHrP (FIG. 9), and many of these tumors secrete PTHrP [Yin et al, 2003; Guise et al, 2005]. There are a few reports of direct effects of PTHrP on tumor growth and invasion for breast cancer and myeloma. bPTH7-34DD can have direct effects on tumor, either via β-arrestin or by competitive inhibition of PTHrP autocrine signaling.

Experimental approach: Tumor cell lines can be grown in vitro in standard media+the four treatment conditions described in General Methods. Cells can be tested for growth effects at 2, 4 & 6 days by MTT assay. Effects on invasion can also be tested on MDA-MB-231 and 4T1 cells using standard 8 µm pore transwell Matrigel invasion assays (Corning), according to manufacturer's instructions.

Expected results & interpretation: No effects on tumor growth or invasiveness with MDA-MB-231 or 4T1 cells are expected. The papers showing autocrine growth effects of PTHrP in breast cancer used stable overexpression or k/d in tumor cells [Zheng et al, 2013; Falzon & Du, 2000], which is likely to alter intracrine signaling by PTHrP, a subject beyond the scope of this application [Kim et al, 2016]. However, Zangari et al [2014], in a confusing paper, showed growth effects of exogenous PTHrP on myeloma cells. PTHrP may be a growth factor for osteolytic prostate cancer cell lines [Iwamura et al, 1994]. If significant effects of bPTH7-34DD on additional tumor cell lines are seen in Aim 1 d, those cell lines can be tested for growth and invasion responses as described.

ii. Mechanism of Action of bPTH7-34DD on Bone Cells (Obs, Ocs, Ots & Adipocytes)

Rationale: Both systemic PTH and local PTHrP play significant roles in skeletal development and homeostasis through actions via PTH1R, expressed by all major cell types in bone. The paradoxical effects of intermittent vs continuous PTH/PTHrP (generally anabolic vs catabolic for bone) are well known [Hock & Gera, 1992]. Less clear are the relative contributions of the different bone cell types or their responses to bPTH7-34DD, except for primary osteoblasts, which respond primarily by increased number and not altered expression of biosynthetic genes such as alkaline phosphatase (alk phos) or type 1 collagen [Bohinc & Gesty-Palmer, 2013; Luttrell et al, 2018]. The literature is silent on how βarr2 stimulation might affect non-Obl cells in bone.

Experimental approach: Cell lines and primary cells can be grown in vitro in standard media+the four treatment conditions described in General Methods and analyzed. Osteoblasts: MC3T3-E1 cells and primary mouse calvarial Obls isolated by collagenase digestion can be grown for 1 & 6 days in proliferation medium with the 4 treatments and assayed for growth by MTT and by PCR for marker gene expression (alk phos, col1a1, Cdkn1a, Runx2, osterix, osteocalcin, RANKL, Opg). They can also be grown in mineralizing medium and stained with Alizarin red for mineralized nodule formation at 14 & 21d. Osteoclasts: Mouse RAW 264.7 cells can be differentiated into osteoclast-like multi-nucleated cells with RANKL under standard conditions [Collins-Osdoby et al, 2003] with the four standard treatments, stained for TRAP and scored for osteoclast number and average number of nuclei per Ocl. Parallel cultures can be assayed by PCR for TRAP, CTSK and TRAF6. Osteocytes: MLO-A5 mouse osteocytic cells can be grown as described for Obls for PCR assay, with target genes Sost, DMP-1, RANKL & FGF23.

Adipocytes: 3T3-L1 cells are plated in 48-well plates at $2.5 \times 10^4$/well in aMEM with 10% FBS and 1% antibiotics, indomethacin (50 µM), dexamethasone (0.1 µM) and insulin (5 µg/ml) to induce adipogenic differentiation. Primary bone marrow non-adherent cells can be flushed from long bones of mice used for EVOCAs, pooled, and similarly plated with DMEM and 10% FBS, 1% antibiotics, dexamethasone (1 µM), indomethacin (60 µM), insulin (10 µg/ml), and 3-isobutyl-1-methylxanthine (0.5 mM). Media can be changed every 2 days. Number of adipocytes is determined by fixing and incubation with Oil O Red (3.5 mg/mL) for 30 min. After microscopic scoring for adipocyte number and average adipocyte diameter per standard field, the dye will be quantified by eluting with isopropanol and measuring absorbance at 490 nm. Parallel incubations can be analyzed at 2, 4 and 6d by SSQ-PCR for adipocyte markers (PPARγ & AP2) and markers of browning (UCP1, Dio2, PGCα), and 6d cultures on coverslips can be fixed and stained with H&E and size and number of adipocytes counted.

Expected results & interpretation: Osteoblasts: PTHrP is expected to increase RANKL expression but not mineralized nodule formation, while bPTH7-34DD increases nodule number and Obl expression of Opg and col1a1, while decreasing Cdkn1a, as previously shown [Gesty-Palmer et al, 2013]. Osteoclasts: Direct effects of PTH1R ligands on purified Ocls are uncertain but might be inhibitory, based on observations that Ocls express PTH1R and can be stimulated by PTH [Dempster et al, 2005]—in which case bPTH7-34DD can be inhibitory, with unknown responses via β-arrestin. Osteocytes: Ots are not only the most abundant cell type within bone but major expressors of PTH1R and its target genes RANKL, DMP-1 and Sost [O'Brien et al 2008; Wein, 2018], which can be stimulated by PTHrP and suppressed by bPTH7-34DD. Adipocytes: Blockade of increased cAMP (due to PKA activation by PTHrP) can prevent browning of 3T3-L1 and primary BMAT cell, leading to suppression by bPTH7-34DD of UCP1 & Dio2 compared to treatment with hPTHrP1-34. The effects of β-arrestin-stimulated signaling on this cell type are unknown.

Alternative approaches: Changes seen in Obls, Ocls and Ots can be confirmed in a more physiological setting of bone by analyzing EVOCA experiments ±tumor and ±the 4 treatments. This approach does not distinguish cell of origin of mRNA changes or direct vs indirect effects—such as RANKL from Ots & Obls increasing Ocls. The adipocyte experiments use BMAT cells from bone. Primary WAT and BAT cells can be isolated from inguinal and interscapular fat deposits of the mice calvarial donors for the EVOCA assays, following published procedures [Kir et al, 2014] and studied with the same experimental design as above. Since most effects of secreted PTHrP occur in bone, BMAT cells seem the appropriate choice. A major effect of PTHrP on adipocytic browning is likely to be via increased cAMP, which should be effectively blocked by bPTH7-34DD, while effects of β-arrestin signaling on adipose browning are unexplored, although 3 major adipocyte GPCRs are P-arrestin-coupled: the β-adrenergic & calcium-sensing receptors & PTH1R. A confounder is Sost, secreted from Ots and increased by PTHrP. Sost is a major regulator of adipocyte differentiation, increasing BMAT [Kim, S P, et al, 2017; Fairfield et al, 2018]. Thus PTHrP from tumor in bone should act on adipocytes directly and indirectly via increased Sost, pathways that can be distinguished by the addition of Sost-neutralizing Ab to EVOCA cultures.

iii. Test if Responses to bPTH7-34DD Require β-arrestin

Rationale: The peptide acts in three ways: competitive inhibitor of PTHrP, inverse agonist of G-protein signaling and cAMP and agonist of β-arrestin signaling. If responses seen are due to β-arrestin, they can be lost in bones or cells from βarr2−/− mice. The PTH1R has some basal cAMP-stimulating activity, which is blocked only by bPTH7-34DD and not PTHrP-neutralizing Ab or the pure competitive inhibitor hPT7-34. The effects of sustained βarr2 activation by bPTH7-34DD are largely unknown beyond those described for osteoblasts and several organs by Luttrell et al [2018].

Experimental approach: Calvariae from 14 d βarr2−/− mice and wt littermates can be tested in 7 d EVOCA experiments ±tumor and ±the 3 treatments and markers of Obl, Ocl, Ot and BMAT responses assessed by SSQ-PCR as detailed in Aim 1b, with tumor burden assayed by gluc in CM as well as by PCR for hRPL32. Parallel cultures can be fixed, decalcified & stained with H&E or Oil Red 0 for changes in bone [Mohammad et al, 2008] and fat. βarr2−/− bone cells: Calvarial osteoblasts can be isolated from control & k/o bones by collagenase digestions and cultured as in Aim 1b. Primary BMAT cells can be isolated from wt & k/o long bones and cultured as described in Aim 1b. Cultured Obls and adipocytes can be treated and analyzed as described in the same Aim.

Expected Results and interpretation: Major cellular PTHrP responses mediated by cAMP can persist in wt & k/o mice. Responses to bPTH7-34DD mediated by βarr2 should be lost in k/o cells. These can include bone-anabolic responses such as depressed osteoblastic Cdkn1a, col1a1 & osteocalcin, depressed osteocytic RANKL & Sost (and a 2o decrease in Ocls & markers), and changes in BMAT PPARγ, UCP1 & Dio2.

Alternative approaches: It is clear from the extensive work of Luttrell et al [2018] that positive responses to bPTH7-34DD require βarr2, so exhaustive experiments with βarr2−/− cells and bones are not needed to prove the point. If major Ocl responses to bPTH7-34DD are found, hematopoietic precursors can be isolated from βarr2−/− mice and study the effects of the four treatments in vitro.

iv. Test if bPTH7-34DD is Effective Against Multiple Tumor Types

Rationale: Tumors other than those of the breast also secrete PTHrP and colonize bone: multiple myeloma, prostate cancer, lung adenocarcinoma melanoma, renal carcinoma and squamous cell carcinoma. bPTH7-34DD should be effective against bone involvement due to these tumors.

Experimental approach: Additional human cancer cell lines can be screened for PTHrP and PTH1R mRNAs, as shown above in FIGS. 8 & 9, with the goal of identifying 2-4 lines of each tumor type. These can be grown in culture ±10 ng/ml TGFβ1 and 48hd CM assayed by ELISA for PTHrP. Two lines of each type secreting PTHrP comparably to MDA-MB-231 [Yin et al, 2003, Table 2] can be tested for growth in bone by 7d EVOCA±bPTH7-34DD, as assessed by total human RPL32 content by SSQ-PCR.

Expected Results and interpretation: PTHrP+ osteolytic cell lines can be growth inhibited by bPTH7-34DD in the EVOCA assay. Less certain is what effect the peptide can have on the growth of an osteoblastic cell line that secretes PTHrP, such as prostate LNCaPs.

4. bPTH7-34DD Tests i. bPTH7-34DD in a Model of Bone Metastases

Experiments were designed to test bPTH7-34DD in a model of bone metastases for effects on: i) Tumor burden; ii) Osteolytic lesions; iii) Sensory innervation of tumor in bone; iv) Bone formation/loss: both systemically and adjacent to tumor; v) Skeletal muscle loss.

Rationale: bPTH7-34DD can block breast cancer bone metastases in the standard MDA-MB-231 model at least as well as PTHrP-neutralizing Ab [Guise et al, 1996] with additional effects to decrease skeletal muscle cachexia, bone pain and possibly HEIM. A prevention model (in which treatment begins at the same time as tumor inoculation) can be analyzed in full detail, with the BC cells injected into one tibia, allowing use of the contralateral leg as the tumor-free control and avoiding complications of metastases to other sites via the intracardiac route, which requires higher animal numbers for analysis. The mice from this experiment can receive complete analysis for bone parameters by computerized quantitative histomorphometry of both tibiae, as well as characterization of muscle and fat parameters, detailed necropsy for secondary metastases and immunohistochemistry for a series of markers in bone, as well as calcein double labeling and the determination of bone formation rate. Serum at euthanasia can be assayed for Ca++ and markers of bone formation and bone resorption. This experiment parallels a report where inhibition of sclerostin (with Ab or Ot-targeted k/o) increased BMD and other bone parameters in a model of osteolytic multiple myeloma [Delgado-Calle et al, 2017]. Contrary to expectation, MM tumor burden was unaffected by treatment, a result confirmed by two other laboratories.

Experimental approach: Experiment 1) is a prevention model, using human MDA-MB-231 cells & nude mice, beginning treatment on the day (day +1) of tumor inoculation. Alzet 1004 minipumps are sterilely loaded with bPTH7-34DD according to the manufacturer's instructions) and subcutaneously implanted in the backs of the mice (alzet.com/resources/documents/ALZETIACUCapproval-formguide.doc). The pumps deliver 0.11 µl/hr and with 1 mg/ml peptide in PBS supply 2.5 µg peptide/~25 g mouse/d, 2.5× higher than the dose shown to increase bone formation in mice over 4 weeks [Gesty-Palmer et al, 2013]. Under the same anesthesia used for pump implantation, 104 MDA-MB-231 BC cells (freshly washed and resuspended in 20 µl of sterile PBS) can be intratibially inoculated, as previously described in detail [Wright et al, 2016]. Control animals can receive the same volume of PBS by intratibial inoculation. Mice can be analyzed by weekly weighing and 25 µl blood draws (beginning at d−1) for serum determination of tumor burden by gluc. Mice can be baseline evaluated at d−1 by weighing, Piximus DEXA for whole body composition (body fat, bone mineral and lean mass) followed by Faxitron X-ray (under the same anesthesia as the Piximus analysis) of the limbs. The same analyses can be repeated just prior to euthanasia at 28 d. During the course of the animal experiment the tibias of tumor-bearing mice can be X-rayed at wks 2 & 3 and at euthanasia after 4 weeks (28 d), following injection of all mice with 20 mg/kg calcein in PBS at d21 & d26 to permit double-label assessment of new bone formation.

Analytical procedures: Serum can be collected at euthanasia for assay of ionized calcium and circulating markers, including total tumor burden by G-luc. $Ca^{++}$ is determined from 2.5 µl serum aliquots with QuantiChrom kits. Prior to euthanasia tumor-bearing and uninvolved tibiae of all mice can be X-rayed for osteolytic bone lesions and analyzed for body composition parameters by Piximus DEXA using the same anesthesia for both. Animals can then be euthanized and cachexia can be assessed by weighing dissected gastrocnemius and quadriceps muscles, which can then be fixed for routine histology. At the same time euthanized animals can be subjected to full necropsy to inspect for macroscopic metastases to non-bone sites of $GFP^+$ BC cells. Inguinal WAT and interscapular BAT deposits can also be dissected, weighed and fixed for routine histology of adipocytes. Legs can be dissected, cleaned of surrounding tissue and fixed, followed by microCT analysis of both tibiae from each animal as described [Delgado-Calle, Anderson, et al, 2017]. After the microCT analysis, the tibiae can be prepared by decalcification for histology and histomorphometry (bones from 8 animals) or for nondecalcified sectioning for calcein double-label analysis to calculate BFR. H&E sections can be stained for TRAP to visualize Ocls, and by IHC with antibodies for TRPV1 and CGRP to visualize sensory innervation of tumor in bone and with antibodies against PPARγ & UCP1 to visualize adipocytes and WAT-BAT conversion). Histomorphometry can follow routine procedures [Uy et al, 1997; Delgado-Calle, Anderson, et al, 2017; Delgado-Calle, Tu, et al, 2017] and bone parameters can be evaluated according to published standards [Dempster et al, 2013].

Serum measurements: gluc for tumor burden, P1NP for bone formation, CTX for bone resorption, Ca++ for HEIM vs normocalcemia. Tumor measurements: Osteolytic lesion number from X-ray, Osteolytic lesion area from Bioquant analysis of X-ray image data. Histomorphometry & TRAP staining: OcN/mmTBI; tibial tumor burden. Bone measurements: Histomorphometry: Ob.S/BS; Ob.N/BS; Oc.S/BS; Oc.N/BS; MicroCT: BV/TV; Tb.N, Tb.Th, Tb.Sp; Calcein double-label: BFR/BS; MAR; IHC assessments: SNs: density by CGRP; pain activation by TRPV1, Adipocytes by PPARγ; BAT by UCP1. Whole body measurements: DEXA Piximus results: fat mass; lean mass; BMD; Muscle weights: gastrocnemius; quadriceps; Fat deposit weights: inguinal (WAT), interscapular (BAT).

Expected results & interpretation: Peptide treatment of mice without tumor can increase bone anabolic measures comparable to those seen previously [Gesty-Palmer et al, 2013]. In the +tumor groups, peptide treatment should significantly reduce tumor burden both as serum gluc and by post mortem histomorphometric analysis of tibiae. Bone anabolic parameters can be maintained by bPTH7-34DD or even improved vs untreated control mice. It is uncertain if untreated BC+ animals can develop HEIM or systemic cachexia that is reduced directly by the treatment, or if changes in serum Ca++ and cachectic markers can be due to reduction in total PTHrP+ tumor vs direct actions on calcium handling or adipocyte browning. H&E sections of inguinal and interscapular fat can be stained for PPARγ and UCP1 to test for systemic effects of tumor and peptide treatment on adipocytes. PTHrP antagonists stimulate hair growth and prevent chemotherapy-induced alopecia [Skrok et al, 2015], settings in which bPTH7-34DD can be beneficial, with future patient applicability. The backs of the nude mice can be inspected by photographing prior to euthanasia and counting hair shafts as described [Peters et al, 2001].

Alternative approaches: This experiment replicates the experimental design used to show efficacy of blocking PTHrP (or TGFβ actions) to reduce tumor burden in the MDA-MB-231 mouse model [Guise et al, 1996; Kakonen et al, 2002] with the only change being the use of intratibial rather than intracardiac delivery of BC cells to bone. Animal experiments have been designed to minimize interventions and anesthesia to optimize mouse survival and well-being. Many other models of bone metastases and MM colonization of bone are available [Wright et al, 2016] and can also be tested. A standard animal model, analyzed in depth, can suffice to support clinical development of bPTH7-34DD. Future experiments are needed to test the peptide in established animal models of cachexia, HEIM and cancer bone pain, without the confounding effects of reduced tumor burden. MDA-MB-231s cause cancer bone pain, and a variety of HEM animal models are known. These animal models exceed the scope and budget of the current application.

ii. bPTH7-34DD In Vivo

Experiments were designed to test bPTH7-34DD in vivo to inhibit: 1) Orthotopic tumore growth; ii) Growth of established tumor in bone; iii) Prevention of bone metastases; iv) Tumor growth & metastases in an immuno-competent model. Except as indicated, all animal experiments will use the same design: animal experiment groups: A) No tumor, no treatment; B) No tumor, treated with bPTH7-34DD; C) +Tumor, no treatment; D) +Tumor +treatment. Mouse usage for all experiments will be with n=12/group, which was that used in the original experiments to show significant involvement of PTHrP in the MDA-MB-231 model [Guise et al, 1996; Yin et al, 1999; Kakonen et al, 2002]. Total tumor burden in all groups will be followed by weekly assay of serum gluc.

Rationale: The Aim addresses a series of questions unanswered by Aim 1A: Is orthotopic BC growth blocked by bPTH7-34DD?; Is growth of established bone metastases decreased by bPTH7-34DD?; Does pretreatment with bPTH7-34DD decrease bone metastases?; Does the immune system contribute to effects of bPTH7-34DD?; Is bPTH7-34DD as effective by daily injection as by continuous infusion?; Does bone formation suppress bone metastases or inhibit tumor growth?—as proposed by us [Suvannasankha & Chirgwin, 2014] and confirmed with pulsatile PTH pretreatment of BC bone metastases by Swami et al [2017].

Experimental approaches: An orthotopic growth model can be used in which $10^5$ tumor cells are inoculated into a mammary fat pad and growth followed. Only two groups are needed for this experiment, since only tumor-bearing animals are tested: C) and D): 24 female BALB/c nu/nu. 24 Alzet 1004 minipumps. Tumor growth can be followed by caliper measurement, weekly serum glue assays, and the mice can be analyzed at necropsy for metastases to soft tissue sites and bone. A treatment model, beginning treatment by pump implantation at d10, after confirmation of tumor take by serum G-luc assay at d7 can be studied. Groups C) and D) only: 24 female BALB/c nu/nu mice. 24 Alzet 1004 minipumps. Mice can be analyzed by tibial X-rays at weeks 0, 2, 3 & 4 and muscle and bone assessed at euthanasia including μCT, as well as weekly serum glue for tumor burden. A pretreatment model, in which animals are treated ip with vehicle (PBS) or daily injection of 40 g/kg/d bPTH7-34DD for 4 weeks and 2 days later inoculated +tumor only and followed for 4 weeks with no additional injections or treatments can be studied. Groups A)-D) only: 48 female athymic nudes. Mice can be analyzed with additional partial characterization of bone parameters by tibial X-rays at weeks 0, 2, 3 & 4 and μCT at euthanasia. The dose of peptide is known to cause new bone formation by 4 weeks [Gesty-Palmer et al, 2009].

Other experiments can test contributions of the immune system to the treatment effects of bPTH7-34DD in immunocompetent mice with the syngeneic mouse 4T1 breast cancer line. One experiment can be a prevention model, using mouse 4T1 cells & BALB/c mice, beginning treatment on the day of tumor inoculation (104 cells it) with 2 groups, all +tumor and ±treatment): 24 female BALB/c wt mice. 24 minipumps. Mice can be analyzed as in other experiments to compare responses ±an intact immune system. Another experiment can be an orthotopic growth model, using mouse 4T1 cells & BALB/c mice, beginning treatment on the day of tumor inoculation ($10^5$ cells in the MFP) with 2 groups, all +tumor and ±treatment):24 female BALB/c wt mice. 24 minipumps. Mice can be analyzed as in other experiments to compare responses±an intact immune system. In another experiment, the route of administration can be tested using MDA-MB-231 cells, as in other experiments described herein, in which mice can receive it tumor (groups A & B) or in the mammary fat pad (C & D). The experiment is designed to ask if pulsatile once-daily administration of bPTH7-34DD has the same effect as continuous administration of the same total 24 hr dose. Both treatments are anabolic for bone, but the pulsatile treatment is unlikely to provide 24 hr competitive inhibition of PTHrP locally secreted from tumors. Beginning on the day of tumor inoculation, mice will receive IP injections of vehicle (PBS) or daily injection of 100 µg/kg/d bPTH7-34DD for 4 weeks. The daily dose is equivalent to that delivered over 24 hrs by minipump in Experiment 1). Mice will be analyzed as described above.

Expected results & interpretation: Orthotopic growth model: bPTH7-34DD is not expected to decrease tumor growth in the MFP, unless experiments in Aim 1a) suggest a direct anti-tumor effect of the peptide. Published experiments showing growth effects of PTHrP in BC cell lines have used k/d or overexpression of PTHrP, which is likely to affect the cells by a receptor-independent intracrine route.

Treatment of established metastases: Less effective suppression of tumor burden than in Aim 2A is expected. Treatment of established bone metastases in the MDA-MB-231 model is less effective than the prevention model, in which agent is begun at the same time as tumor inoculation (Aim1a). Many agents work only in prevention not treatment settings, but some do [Juarez et al, 2012; 2017]. Pretreatment to prevent metastases: bPTH7-34DD can very effectively suppress formation of osteolytic lesions and tumor growth in bone. Stimulation of anabolic bone formation by daily injection of PTH has this effect in the 4T1 model [Swami et al, 2017] and bone formation can oppose growth of metastases and MM in bone [Suvannasankha & Chirgwin, 2014]. However, in MM models stimulation of bone formation with Sost-neutralizing Ab or targeted k/o of Sost surprisingly did not decrease tumor burden [Delgado-Calle et al, 2017].

Bone metastases in immune-competent mice: The host immune system is not expected to significantly alter bone metastatic responses between MDA-MB-231/nude and 4T1/BALB/c models. Swami et al [2017] carried out these models in parallel, without reporting significant differences in responses to intermittent PTH treatment. Orthotopic growth in immunocompetent mice: bPTH7-34DD is not expected to decrease tumor growth in the MFP but can alter bone metastases to bone but not liver or lung, although the animal numbers are not large enough to power statistically significant changes to individual sites. Bones with lesions visible by Faxitron X-ray can be examined by histology and histomorphometry for changes in bone and tumor.

Efficacy against bone metastases of intermittent daily vs continuous bPTH7-34DD: Intermittent vs continuous peptide can be less effective at blocking tumor PTHrP binding to PTH1R on target cells in bone. It should be less effective at reducing tumor burden, unless the anabolic effects of bPTH7-34DD on bone formation are the major route of its anti-tumor action. Ligand binding stimulates receptor desensitization by endocytosis, uncoupling of ligand from receptor, followed by recycling of PTH1R to the plasma membrane. Within several hours of bolus injection of peptide, the receptor will be prepared for another round of ligand binding; so that the presence of PTHrP continuously secreted from tumor should reactivate the catabolic responses mediated by receptor activation of PKA. Again, if the persistent bone anabolic responses are the major determinant of tumor suppression, then intermittent bPTH7-34DD dosing can be effective against bone metastases.

Alternative approaches: If major responses appear to be mediated by β-arrestin, the Eo771 mouse BC cell line could be tested in syngeneic BALB/c βarr2−/− mice available from the Luttrell laboratory. Eo771s are much less studied than 4T1s as a model of bone metastases but express PTHrP and cause osteolytic lesions in BALB/c's.

5. Mouse Experiments

EVOCA assays (Aim 1): Bone metastasis models rely on transplanting tumor cells into xenograft hosts, a complex, low throughput and expensive bottleneck step for drug development. An alternative method has been developed in which bones are painlessly harvested from mouse pups and grown ex vivo under conditions that support efficient engraftment of human cancer cells. The procedure, called EVOCA (ex vivo organ culture assay), follows established protocols [Mohammad et al, 2008]. Mouse pups prior to weaning have undeveloped immune systems and thus tolerate the co-culture of human cells without drug treatment or the use of immune-compromised strains. EVOCA eliminates the need for cross breeding gene knockouts, etc, into immunocompromised strains.

Species strain, ages, sex and numbers to be used: Pregnant Swiss Webster mice can be purchased as the source of the neonatal mice. The dams can be euthanized when their pups are collected for tissue harvest rather than establishing a breeding colony, which is more wasteful of experimental animals. Calvariae are isolated for the co-culture assays and long bones and fat deposits for cell preparations.

Xenograft models (Aim 2). Orthotopic model: breast cancer mammary fat pad (MFP) injection allows longitudinal studies of breast cancers from localized disease to metastasis. MFP injection of MDA-231 human breast cancer cells in immunocompromised mice seldom causes distant metastasis. 4T1 is a mouse breast cancer cell line that engrafts in syngeneic immunocompetent BALB/c mice. 4T1 grows rapidly in the MFP and aggressively metastases within 2-4 weeks to visceral and skeletal sites. Both cell lines when injected intratibially induce local osteolytic tumors in bone with minimal impact outside of bone marrow engraftment [Wright et al, 2016].

Mice, 4-6 weeks of age will be purchased from Harlan and housed under standard conditions. Upon receipt, the female mice (necessary as hosts for breast cancer cells) can be allowed to acclimate for at least 3 days. Baseline: all mice can be weighed, ear-marked, and subject to baseline X-rays (of both hind limbs only) and Piximus DEXA scans under a single session of light inhalation anesthesia for total body composition (fat mass, lean mass, bone mineral content). 25 µl of blood can be drawn and serum stored at −70° for reference. The main experiment can begin the next day (designated +1).

In all models, experimental groups can be: A) No tumor, no treatment; B) No tumor, treated with bPTH7-34DD; C) +Tumor, no treatment; D) +Tumor, +treatment. Mouse usage for all experiments will be with n=12/group, which was that used in the original experiments to show significant involvement of PTHrP in the MDA-MB-231 model [Guise et al, 1996; Yin et al, 1999; Kakonen et al, 2002]. Decades of experience with this model have shown that n=12 gives useful statistically significant results. All cell lines secrete Gaussia luciferase (gluc) and GFP, to allow for tumor burden measurement by serum gluc, and whole body fluorescent imaging. Drug delivery can be via intraperitoneal injection or continuous administration using subcutaneous Alzet 1004 minipumps.

i. Procedures

Subcutaneous minipump placement: Azlet 1004 pump filled with bPTH7-34DD or PBS can be placed on the dorsum, slightly caudal to the scapulae (The manufacturer's detailed IACUC-ready protocol is available at alzet.com/products/guide to use/implantation and explantation.html).

Animals can be anesthetized using intraperitoneal ketamine injection at 80-100 mg/kg body weight or isoflurane 1%-3% inhalant. Make an incision 1.5 times the diameter of the pump perpendicular to the pump's long axis. Spread the subcutaneous tissue to create a pocket at the size that allow some free movement of the pump but not so large that it will slip. The pump should not rest immediately beneath the incision. Insert a filled pump into the pocket, delivery portal first. Close the wound with wound clips or suture. Recover the animal following the IUSM Rodent Anesthesia guidelines including postoperative and analgesia using Buprenorphine and/or Carprofen.

Tumor injection: Intratibial tumor injection: Mice can be pretreated with a dose of Buprenorphine prior to injection and Carprofen can be administered for pain after injection. The cells or saline can be injected into the cortex of the anterior tuberosity of the tibia using a 27 gauge ½ inch needle. After penetration of the cortical bone, the needle can be further inserted into the shaft of the tibia. Twenty microliters of cell suspension can be deposited into the cortex. To prevent leakage, a sterile cotton swab can be held against the site for one minute.

Mammary fat pad tumor injection: Animals can be anesthetized using intraperitoneal Ketamine injection at 80-100 mg/kg body weight or isoflurane 1%-3% inhalant. Breast cancer cells ($10^5$ cells; final volume of 20 μL in PBS) (or tumor slurry in Matrigel) can be injected into the 4th left mammary fat pad just inferior to the nipple of a female mouse. Procedure has been well tolerated with no requirement for postoperative analgesia. Tumors can be measured with calipers to determine tumor volume on Mon, Wed and Fri, once tumor becomes palpable.

Follow up: All mice can be closely monitored following pump implantation and tumor inoculation on the same day and the following one, with the mice housed singly until the sites of experimental treatment are fully healed. Topical ointments and analgesias can be administered as needed for up to 1 week. No tumor-injected mouse can be kept longer than 30 d without euthanasia and no mice can be kept longer than 75 d from time of arrival. Most basic experiments can be ~30 d duration, in which mice can be injected with daily with agent or control for 28 d prior to tumor inoculation, after which they can be monitored without additional treatment for another 28 d. No mice can have pumps removed or replaced, so there can be no multiple survival surgeries. Mice with MFP tumors can be measured with calipers to determine tumor volume on Mon, Wed and Fri, once tumor becomes palpable. Mice can be weighed weekly and inspected for any lesions associated with the implanted minipumps and tumor ulceration.

Blood sampling: Mice can be sampled weekly for 25 μl of blood for serum gluc assay and bone markers. Saphenous blood draw can be performed using a 20 g sterile needle under momentary physical restraint after the skin prep with antiseptics. Blood can be collected with microvette tubes as it come out. Once adequate volume is collected, apply cold compress at the site to stop bleeding. Final bleed can be via intra-cardiac draw. Mice can be anesthetized for this procedure with isoflurane and euthanized immediately after the procedure.

Imaging: Some groups, indicated below, will be X-rayed weekly (legs only) under brief inhalation anesthesia for immobilization during the X-ray. For whole body Piximus DEXA scan (baseline and for Exp 4: at 4 weeks) and Faxitron X-ray (weekly after tumor injection in intratibial tumor injection groups only): Mice can be anesthetized with isoflurane inhaled to effect, with waste gas scavenging and allowed to recover after the procedure. 20 Minutes can be required for each scan. Final DEXA scan and Faxitron X-ray can be done just prior euthanasia. Each mouse can have less than 5 imaging sessions.

Calcein doubling injection: Animals can receive two ip injections in 20 μl of PBS of calcein to label forming bone at days 20 & 26 (relative to euthanasia at day 28).

Euthanasia: can be with cardiac exsanguination followed by cervical dislocation.

Alleviation of pain and suffering. The breast cancer cell lines to be studied grow as masses in the MFP and form osteolytic lesions in bone. MFP masses seem to cause little discomfort to mice and can not become large (<1 g) during the 28 d experiments. Osteolytic lesions in the tibiae can cause bone pain, and severe bone destruction can lead to fracture, hypercalcemia or cachexia. If any mice lose more than 15% of body weight compared to previous weekly weighing, they can be euthanized. Mice showing continuing signs of bone pain and discomfort (behavioral changes, piloerection, vocalizations, etc) can also be euthanized. Severe hypercalcemia results in torpor followed painlessly by death, but such mice can be promptly euthanized should hypercalcemia (serum calcium >15 mg/dl) occur.

ii. Experimental Plan

One experiment can be a prevention model, using intratibial injection of human MDA-MB-231 cells and nude mice, beginning treatment on the day of tumor inoculation. Mouse requirements: 4×12–48 female nude. 48 Alzet 1004 minipumps. The mice from this experiment will receive complete analysis for bone parameters by computerized quantitative histomorphometry of both tibiae, as well as characterization of muscle and fat parameters, detailed necropsy for secondary metastases and immunohistochemistry for a series of markers in bone, as well as calcein double labeling and the determination of bone formation rate. Serum at euthanasia will be assayed for Ca++ and markers of bone formation and bone resorption.

A second experiment can be an orthotopic growth model in which $10^5$ tumor cells are inoculated into a mammary fat pad and growth followed by caliper measurement and weekly serum G-luc assays. Only two groups are needed for this experiment, since only tumor-bearing animals will be tested: C) and D): 24 female nude 24 Alzet 1004 minipumps. Tumor growth will be followed by caliper measurement, weekly serum gluc assays, and the mice will be analyzed at necropsy for metastases to soft tissue sites and bone.

A third experiment can be a treatment model, beginning treatment at d10, after intratibial transplant and confirmation of tumor take by serum G-luc assay at d7. Groups C) & D) only: 24 female nude mice. 24 Alzet 1004 minipumps. Mice will be analyzed by tibial X-rays at weeks 0, 2, 3 & 4 and muscle and bone assessed at euthanasia including μCT, as well as weekly serum gluc for tumor burden.

A fourth experiment can be pretreatment model, in which animals are treated intraperitoneally with vehicle (PBS) or daily injection of 40 g/kg/d bPTH7-34DD for 4 weeks and 2 days later inoculated +tumor only and followed for 4 weeks with no additional injections or treatments. Groups A)-D) only: 48 female nude. Mice can be analyzed as in the above experiment but with additional partial characterization of bone parameters by tibial X-rays at weeks 0, 2, 3 & 4 and μCT at euthanasia. The dose of peptide causes new bone formation by 4 weeks [Gesty-Palmer et al, 2009].

Other experiments can test contributions of the immune system to the treatment effects of bPTH7-34DD in immunocompetent mice with the syngeneic mouse 4T1 breast cancer line.

One experiment can be a prevention model, with 4T1 cells & BALB/c mice, beginning treatment on the day of tumor inoculation (104 cells intratibially) with 2 groups, all +tumor and ±treatment): 24 female BALB/c wt mice. 24 Alzet 1004 minipumps. Mice can be analyzed as in above experiments to compare ±intact immune system.

Another experiment can be an orthotopic growth model, using mouse 4T1 cells & BALB/c mice, beginning treatment on the day of tumor inoculation ($10^5$ cells in the MFP) with 2 groups, all +tumor and ±treatment):24 female BALB/c wt mice. 24 Alzet 1004 minipumps. Mice can be analyzed as in above experiments to compare responses±an intact immune system.

A last experiment can test route of administration, using MDA-MB-231 cells, paralleling above experiments, in which mice can receive tumor intratibially (groups A and B) or in the mammary fat pad (C and D). The experiment is designed to ask if pulsatile once-daily administration of bPTH7-34DD has the same effect as continuous administration of the same total 24 hr dose. Both treatments are anabolic for bone, but the pulsatile treatment is unlikely to provide 24 hr competitive inhibition of PTHrP locally secreted from tumors. Beginning on the day of tumor inoculation, mice will receive IP injections of vehicle (PBS) or daily injection of 100 g/kg/d bPTH7-34DD for 4 weeks. The daily dose is equivalent to that delivered over 24 hrs by minipump in the first experiment. Mice can be analyzed as in other experiments.

B. Example 2

1. Introduction

Following the demonstration that bPTH7-34DD dramatically inhibited the growth of human MDA-MB-231 breast cancer cells in ex vivo coculture with mouse bone, the treatment was tested in a mouse xenograft model in which this cell line is inoculated intratibially in female immunocompromised mice [Wright et al, 2016]. MDA-MD-231 is the most widely used model for preclinical testing of agents against bone metastases, which develop within several weeks and cause extensive osteolytic bone destruction.

2. Methods & Materials

Human MDA-MB-231 breast cancer cells were obtained from the American Type Culture Collection and stably transduced to express secreted Gaussia luciferase (and green fluorescent protein, GFP) as previously described [Siclari et al, 2014]. Luciferase was assayed in 10 µL aliquots of mouse serum as a non-invasive indicator of total tumor burden [Bovenberg et al, 2012] using luciferase assay kits from NE Biolabs and ThermoFisher according to the suppliers' instructions. Purified synthetic bPTH7-34DD (referred to in the figures as BDDP for bodidiparatide) was from LifeTein (New Jersey) and delivered via Alzet 1004 minipumps that provide continuous subcutaneous drug delivery over 4 weeks, as described previously [Maudsley et al, 2015]. Anesthetized 4-6 wk old female BALB/C-nu mice were dorsally implanted with a minipump delivering PBS buffer (vehicle) or 40 µg/kg/d peptide and during the same procedure session were inoculated in a tibia with $10^5$ tumor cells resuspended in PBS as described [Wright et al, 2016]. Serum was drawn weekly for luciferase assay and after 4 weeks mice were anesthetized and euthanized by exsanguination. Mice were immediately analyzes by Faxitron digital X-ray and dual energy X-ray (DEXA) scans of whole body and lower limbs (UltraFocusDXA Faxitron). Injected tibia (left) are designated ipsi(lateral) and uninjected tibia (right) are designated contra(lateral). Images and body composition parameters were generated using the software included with the instruments. Mice were dissected and inspected for extra-osseous tumors. After soft tissue removal, tibiae were then fixed in formalin and preserved in ethanol and subjected to high resolution micro-CT (vivaCT 40, Scanco Medical AG, Bruttisellen, Switzerland). The reconstruction and 3D quantitative analyses were performed using Scanco-provided software according to the manufacturer's instructions. Trabecular bone region reference point was at the growth plate joining, offset 2.0 mm, ROI 2.0 mm. The following 3D parameters in the defined ROI were analyzed, including the relative bone volume over total volume (BV/TV, %), trabecular number (Tb.N), trabecular thickness (Tb.Th), trabecular separation (Tb.Sp). Bones were then decalcified in 0.5M neutral EDTA for subsequent histological analysis, which is ongoing (May 2019).

In the experiment shown, n=5 mice/group. Data were analyzed using GraphPad Prism 7 software and pairwise comparisons were analyzed for significance by Student's t-test.

3. Results

Figure 10:
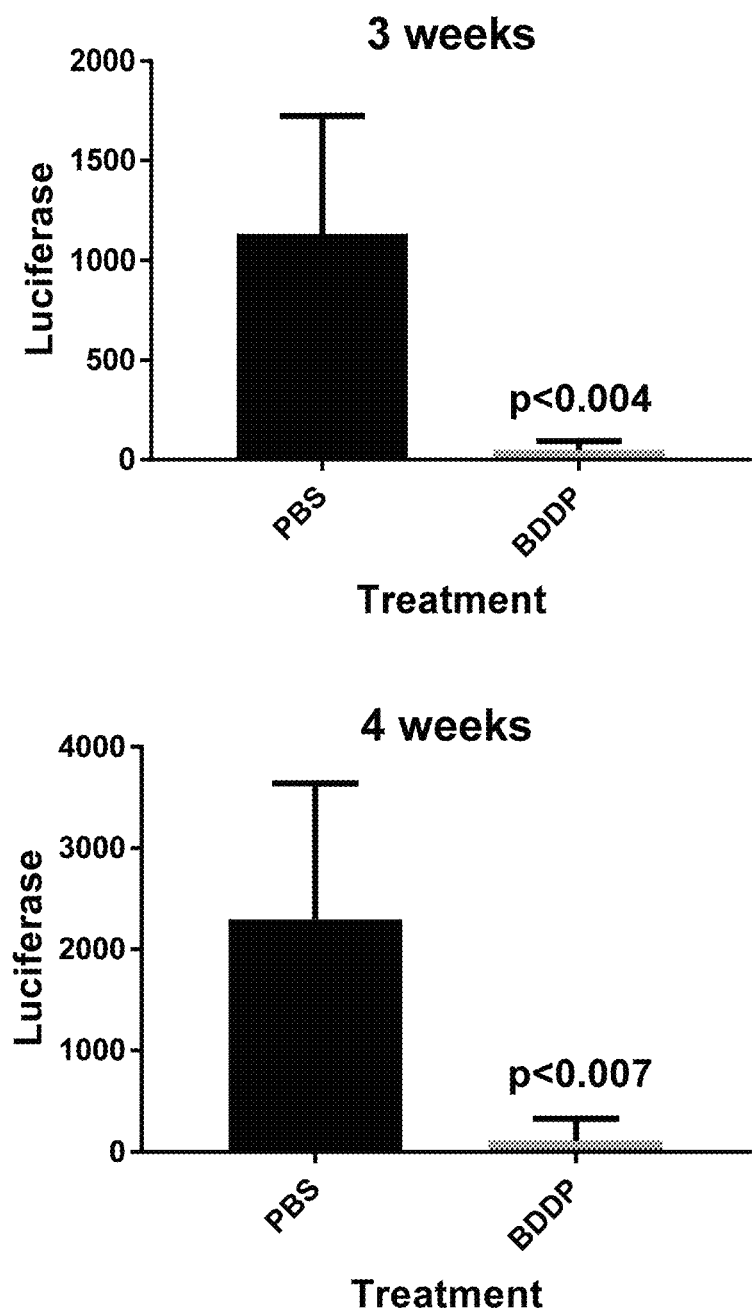
FIG. 10 shows an example of effects of pump infusion of 40 g/kg/d versus PBS vehicle on tumor burden of intratibial MDA-MB-231 via tumor-secreted luciferase in serum of mice. Top: at 3 weeks; bottom: at 4 weeks (end of experiment).
Figure 11:
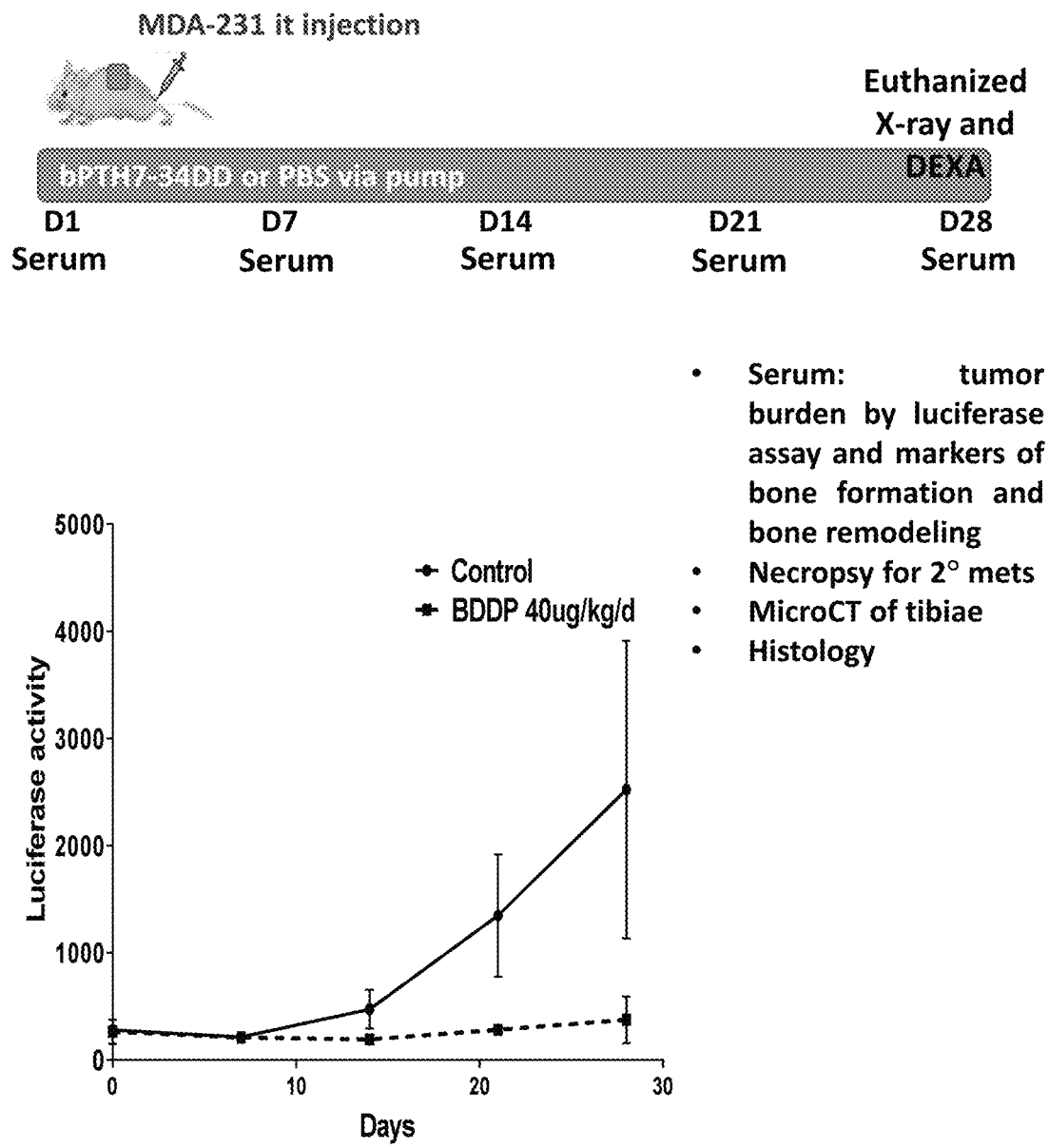
FIG. 11 shows a schematic with alternative representation of tumor burden data from luciferase assays.
Figure 12:
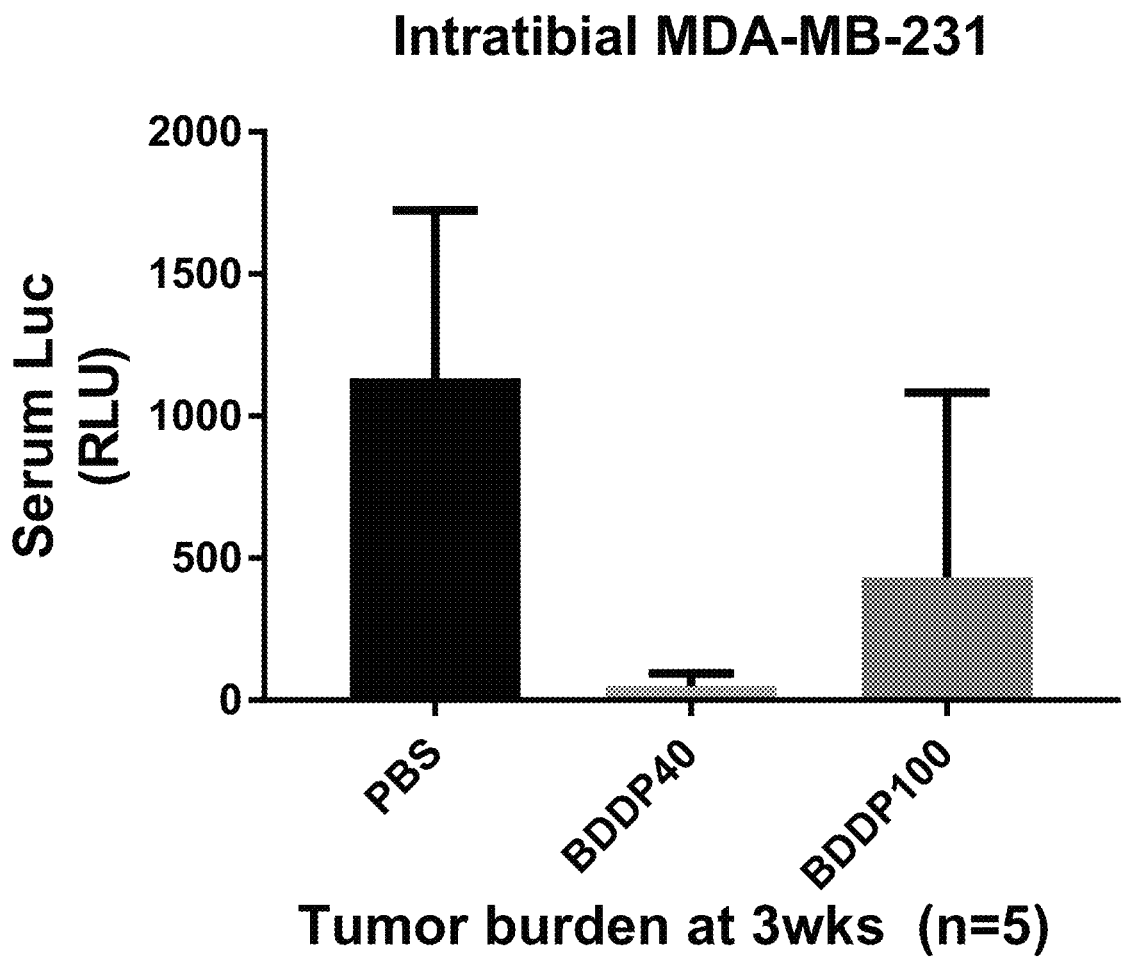
FIG. 12 shows a higher dose of BDDP (100 vs 40) was not more effective to reduce tumor burden due to intratibial MDA-MB-231 cells, measured as serum luciferase at 3 weeks.

Effects of BDDP on tumor burden: The presence of tumor, as Gaussia luciferase activity above baseline, was not detectable in any mice at 1 week post inoculation. Results at 3 and 4 weeks showed that BDDP treatment versus vehicle significantly reduced total tumor burden per mouse by approximately 95% (FIG. 10) at both 3 weeks and at 4 weeks (end of experiment). FIG. 11 shows a schematic of the experimental procedure and that tumor burden was detectable at 2 weeks by luciferase in control but not treated mice. By comparison an addition group that received a higher dose of BDDP (100 versus 40 µg/kg/d) showed a lesser reduction in tumor burden (FIG. 12), indicating that a higher dose of peptide was less effective.

Figure 13:
FIG. 13 shows a representative post mortem microCT scan of tumor-injected bones in vehicle-treated vs peptide-treated groups. Substantial osteolytic destruction of tibia by tumor in vehicle-treated mouse #5 (left) but not in peptide-treated mouse #10 (right).
Figure 14:
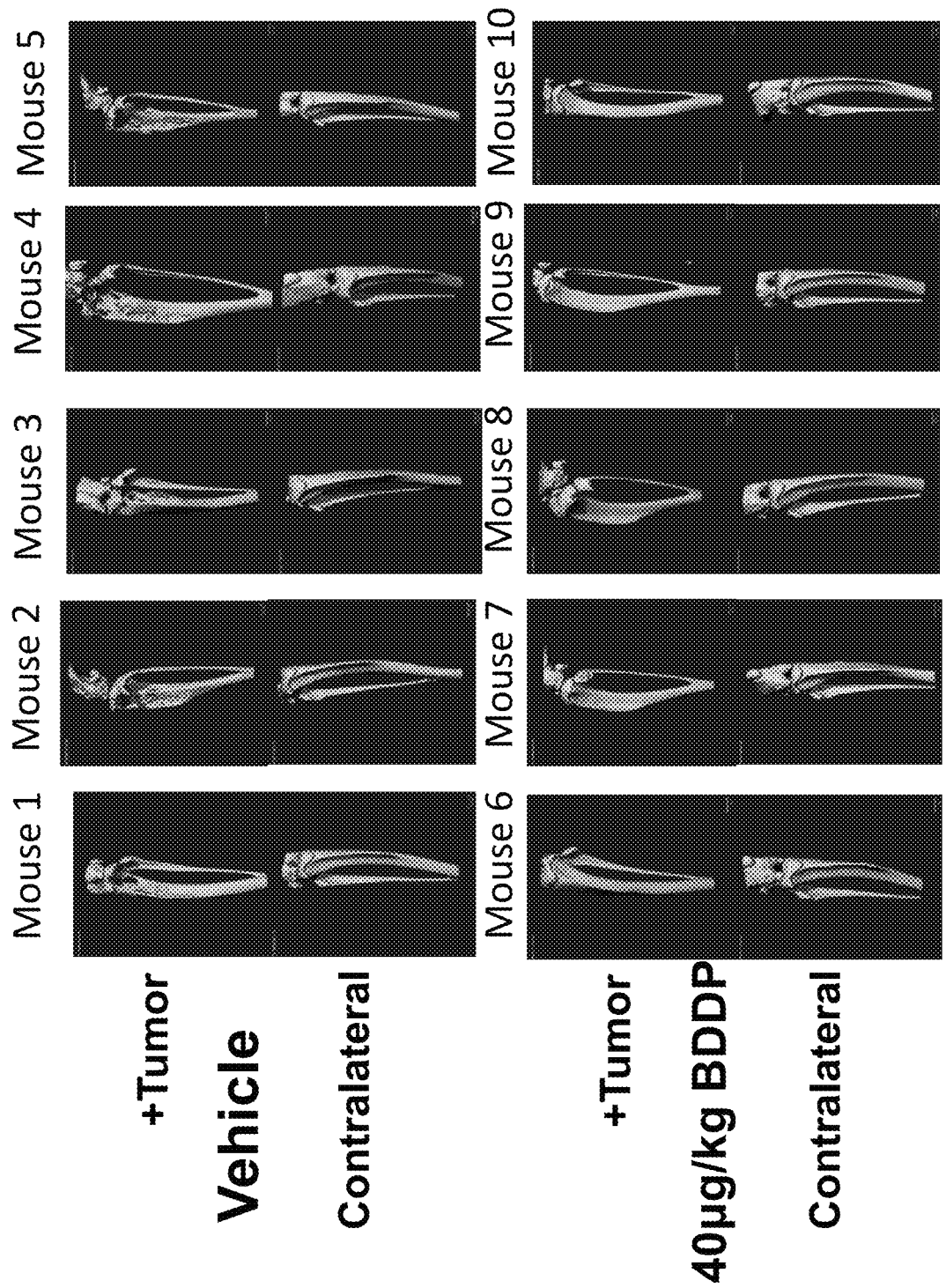
FIG. 14 shows complete microCT images of ipsilateral and contralateral tibiae of mice receiving vehicle vs low-dose BDDP from which representative images were taken for FIG. 13.
Figure 15:
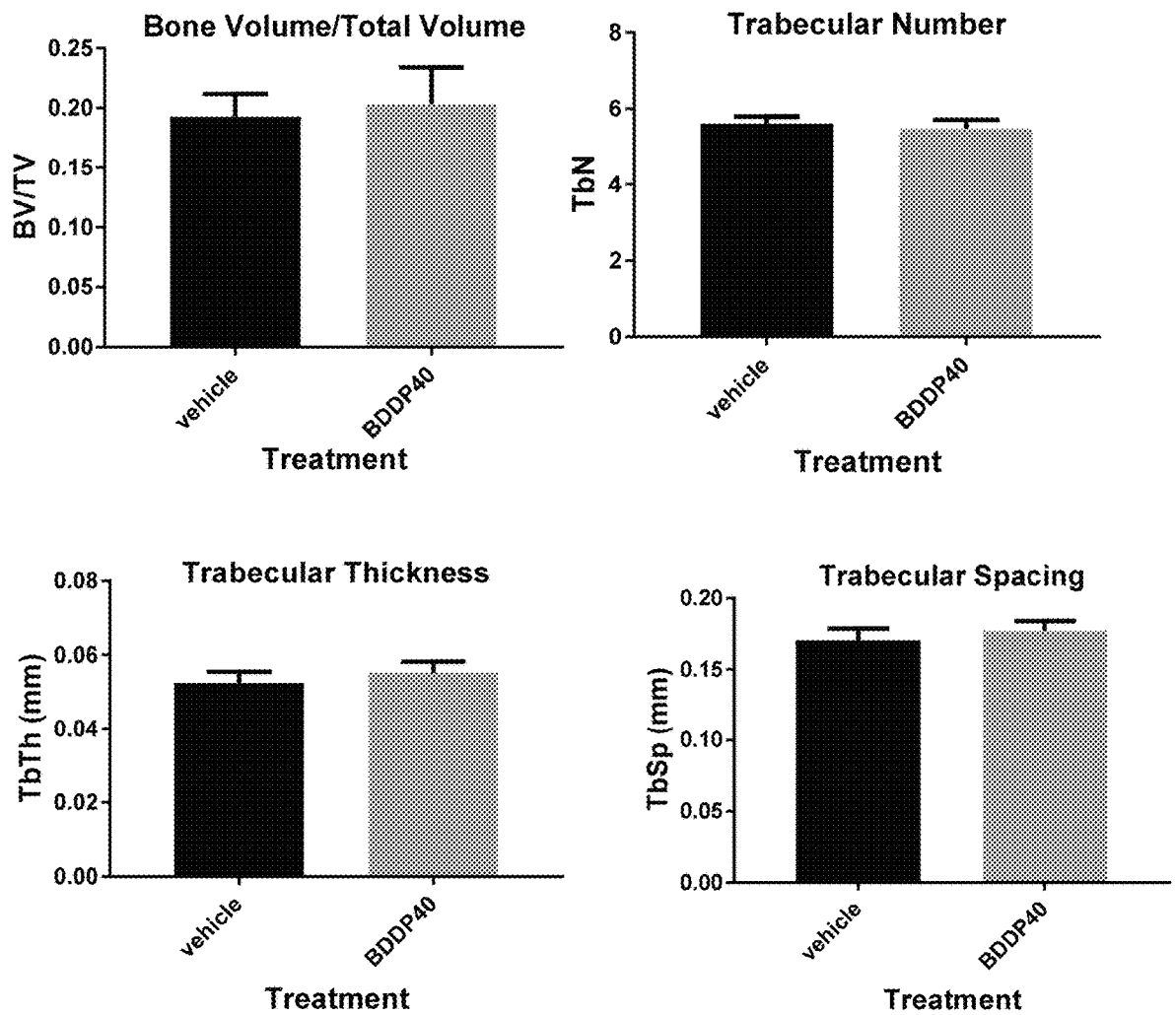
FIG. 15 shows microCT-determined bone parameters of selected regions of interest (ROIs) of proximal tibial trabecular areas of contralateral limbs of mice bearing (ipsilateral) intratibial MDA-MB-231 cells and carrying minipumps to deliver vehicle of 40 ug/kg/d of BDDP. N=5/group. No significant differences between the two groups by Student's t test.
Figure 16:
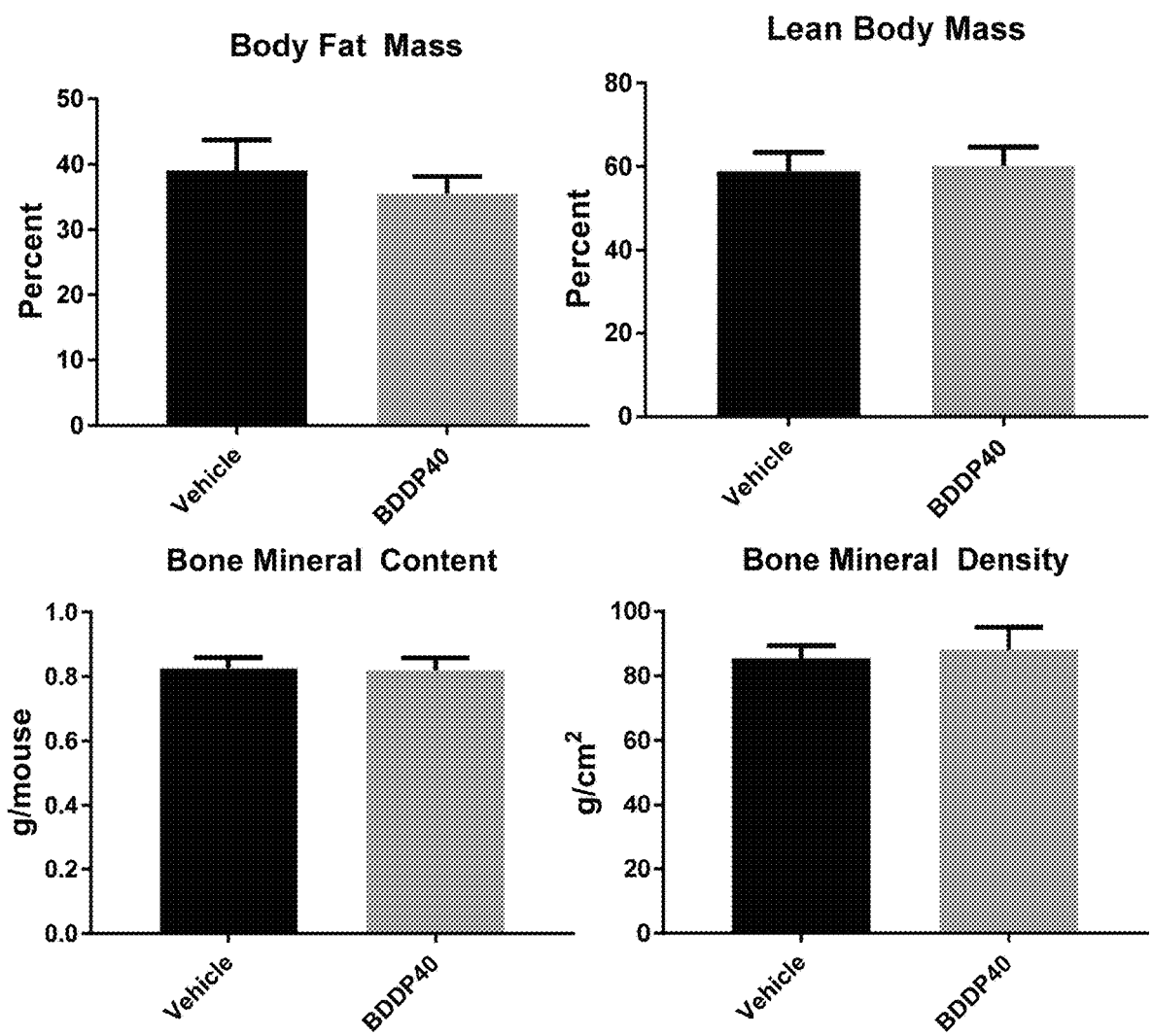
FIG. 16 shows data from female BALB/C$^{nu/nu}$ mice (5/group), all with intratibial MDA-MB-231 inocula, were imaged post-mortem after 4 wks. ROI for data acquisition was entire body exclusive of the head and the tip of the tail. Treated and control groups had indistinguishable body weights at euthanasia.
Figure 17:
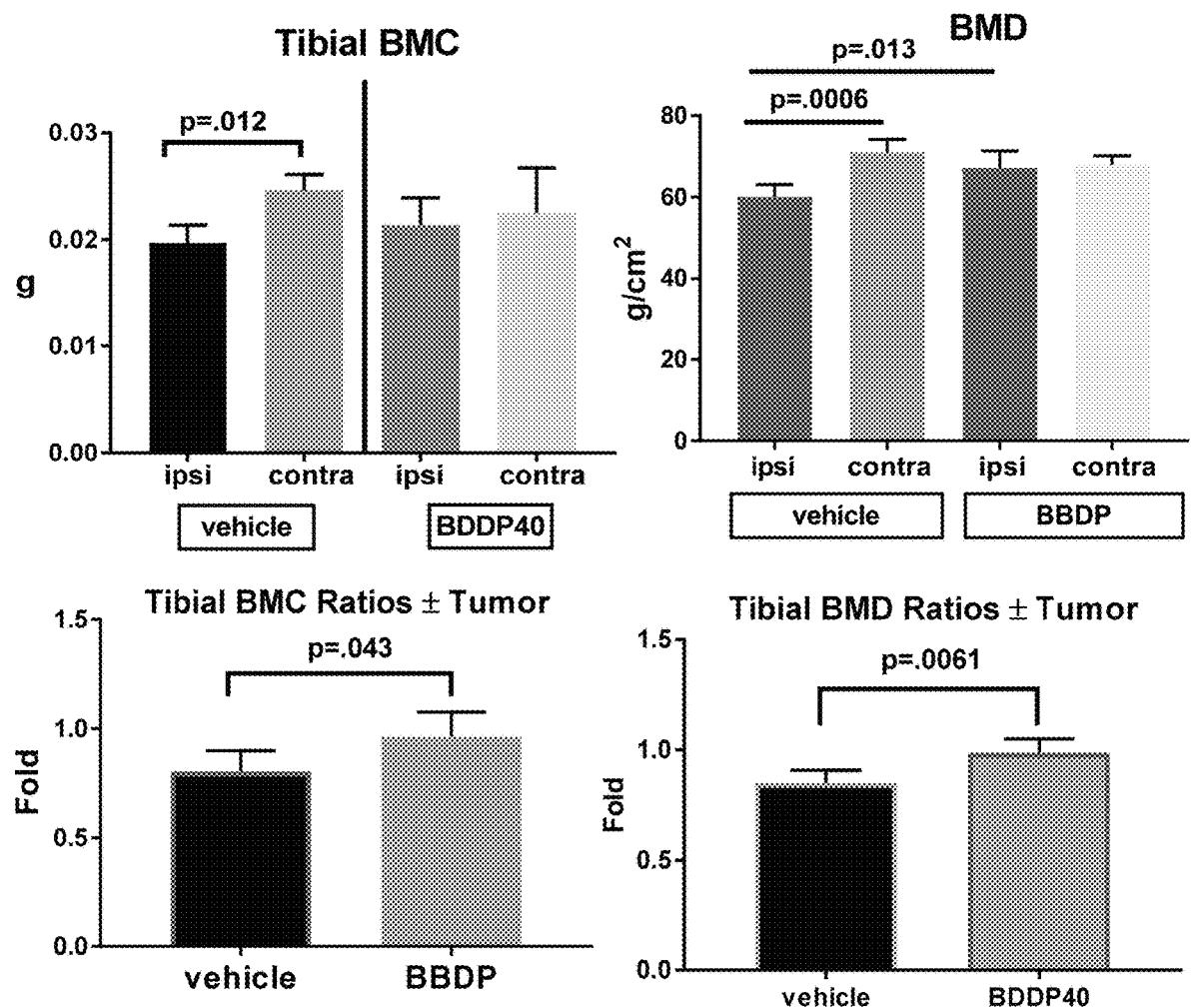
FIG. 17 shows tibial bone parameters of tumor-bearing (ipsi=ipsilateral) and tumor-free (contra=contralateral) mice at 4 weeks, imaged after euthanasia by DEXA with analysis of individual tibiae designated as ROI for BMD & BMC, N=5/group.

Effects of BDDP on bone and whole body parameters: High resolution microCT scans of tibiae showed massive bone destruction in tumor-inoculated (ipsi), vehicle-treated tibiae but not in BDDP-treated ipsilateral tibia (FIG. 13). No contralateral tibia showed osteolysis, and all were indistinguishable from BDDP-treated ipsilateral tibiae (FIG. 14). When the trabecular bone region below the growth plates of the contralateral tibiae were selected as regions of interest (ROIs) and analyzed by µCT, there were no differences in trabecular bone parameters due to 4 weeks of low-dose BDDP (FIG. 15), where BV/TV indicates bone volume over total volume, TbN indicates trabecular number per standard ROI, TbTh indicated trabecular thickness, and TbSp indicates inter-trabecular spacing. DEXA analyses of a series of whole body parameters (FIG. 16) showed no differences in lean mass, fat mass bone mineral density (BMD) or bone mineral content (BMC). When DEXA analyses were restricted to the tibiae alone (FIG. 17), the presence of tumor decreased BMD and BMC in the affected (ipsilateral) versus unaffected (contralateral) bone, and this decrease was prevented by BDDP treatment. These effects were statistically significant.

Figure 18E:
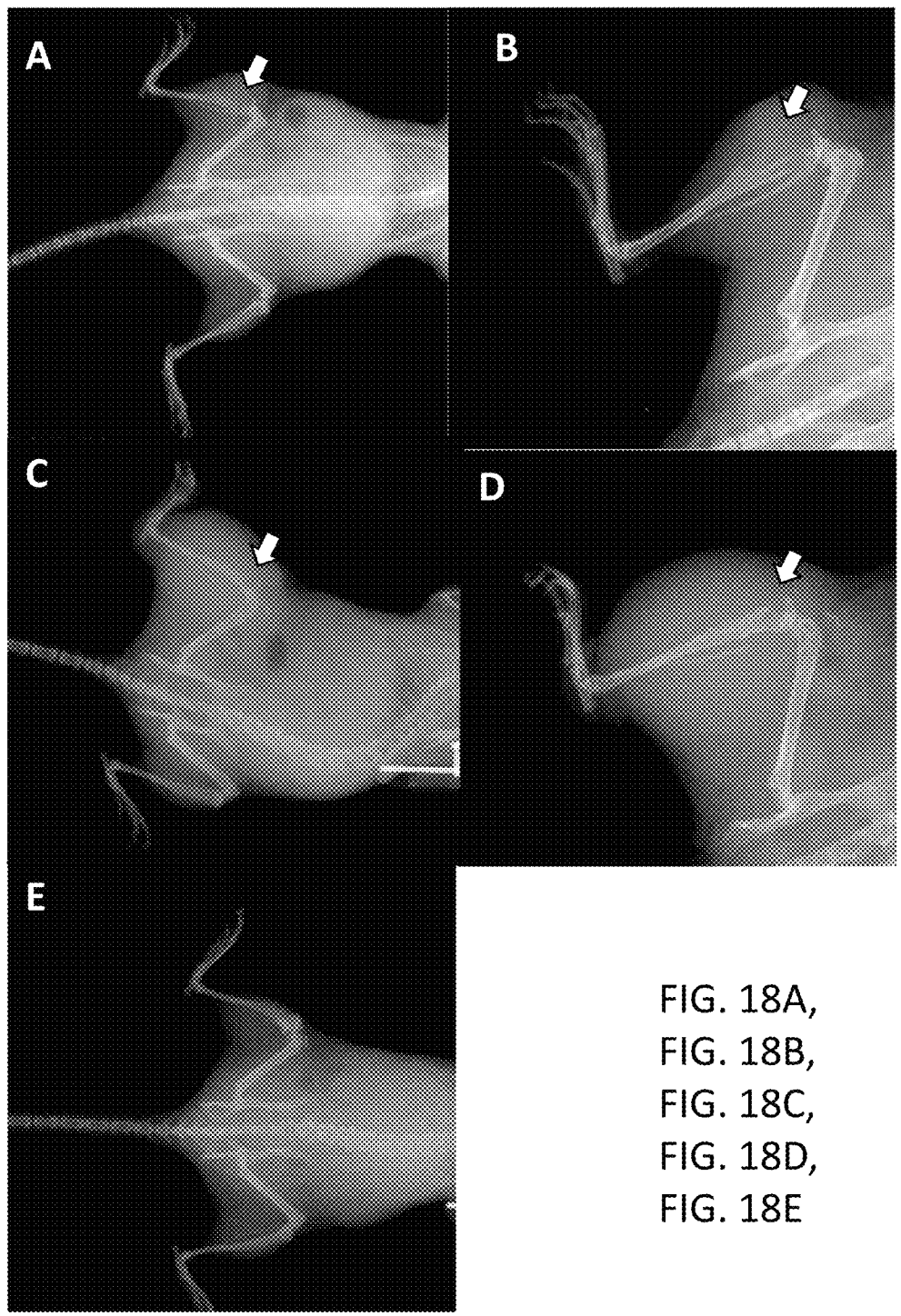
Figure 19:
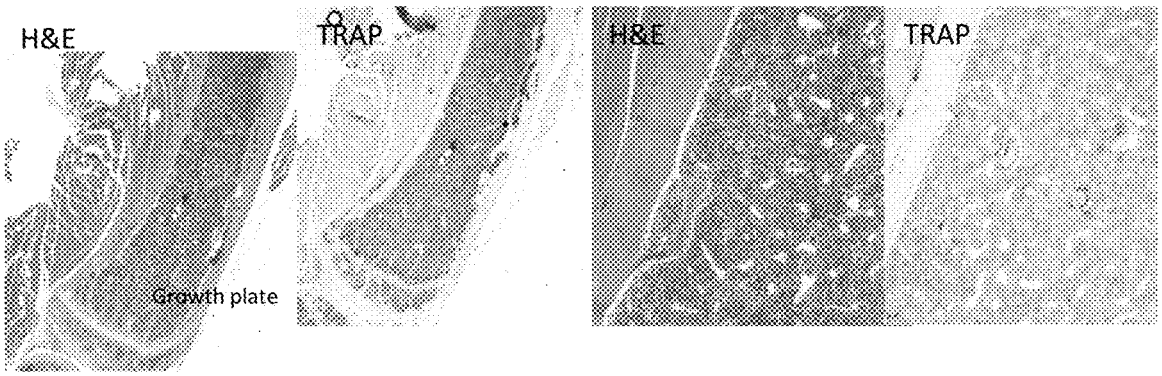
FIG. 19 shows representative histology of tibiae from control mice (no tumor, no treatment), MDA231 implanted tibiae (PBS control) and MDA231 implanted tibiae from mice treated with BDDP 40 ug/kg/day. Panel shows H&E staining and TRAP staining at 2× and 10×, respectively. White arrows point to tumor mass and grey arrow points to osteoclasts at the site of lytic lesion. Untreated mice had a complete effacement of the bone marrow with tumor, and severe bone destruction with tumor extending through bone cortex. Treated mice had much lower tumor load, with some osteoclast activation.
Figure 19:
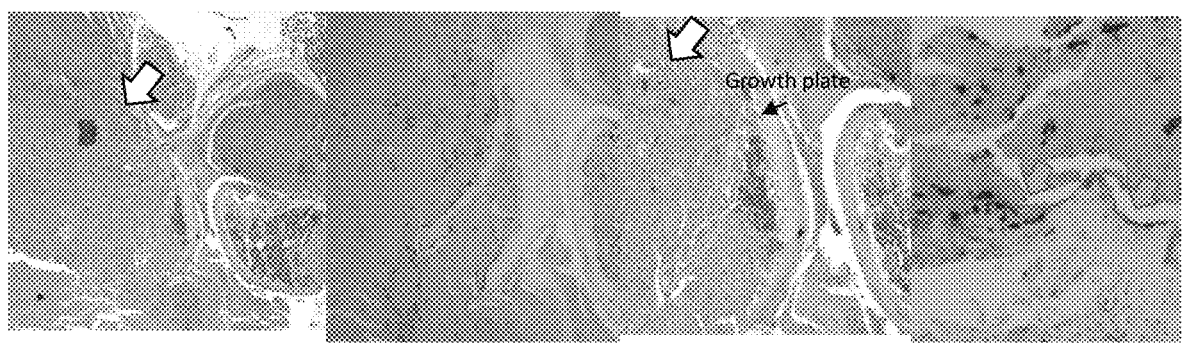
Figure 19:
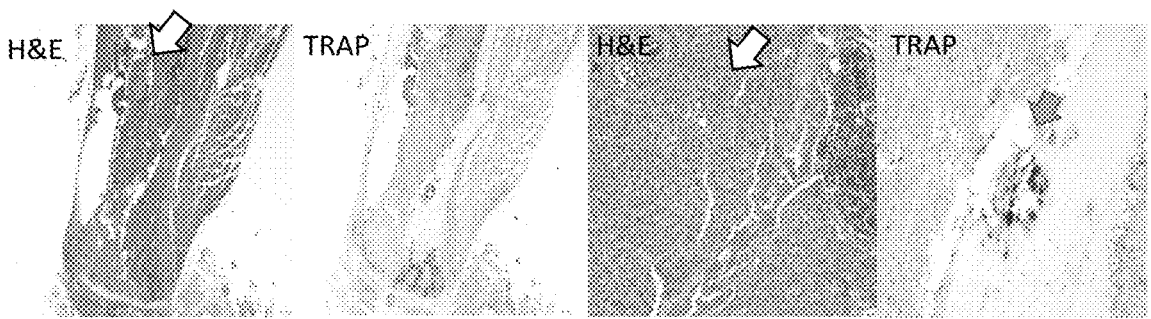
Figure 20:
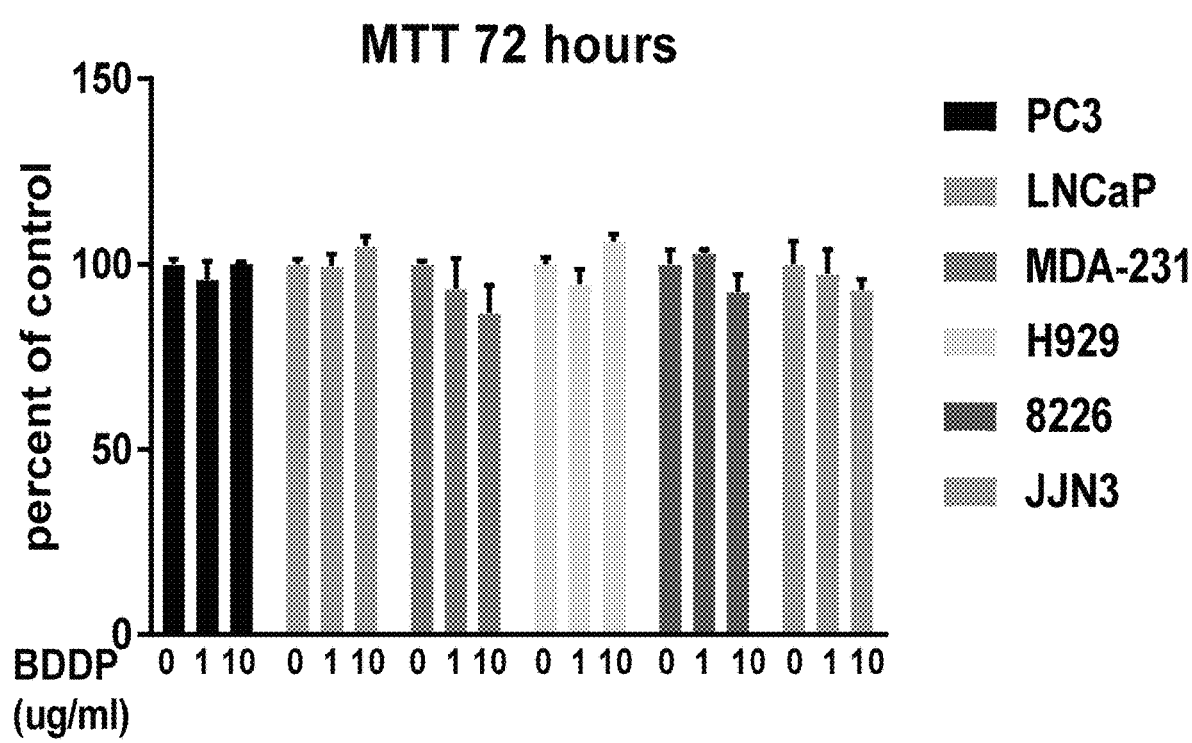
FIG. 20 shows BDDP had no effect on the growth of human cancer cell lines in vitro: prostate (PC3, LNCaP), breast (MDA-MB-231), or multiple myeloma (H929, RPMI-8226, JJN3). Cells grown in standard tissue culture medium +/− BDDP at two concentrations and cell numbers assayed after 72 hrs with a standard commercial MTT assay kit.
Figure 21:
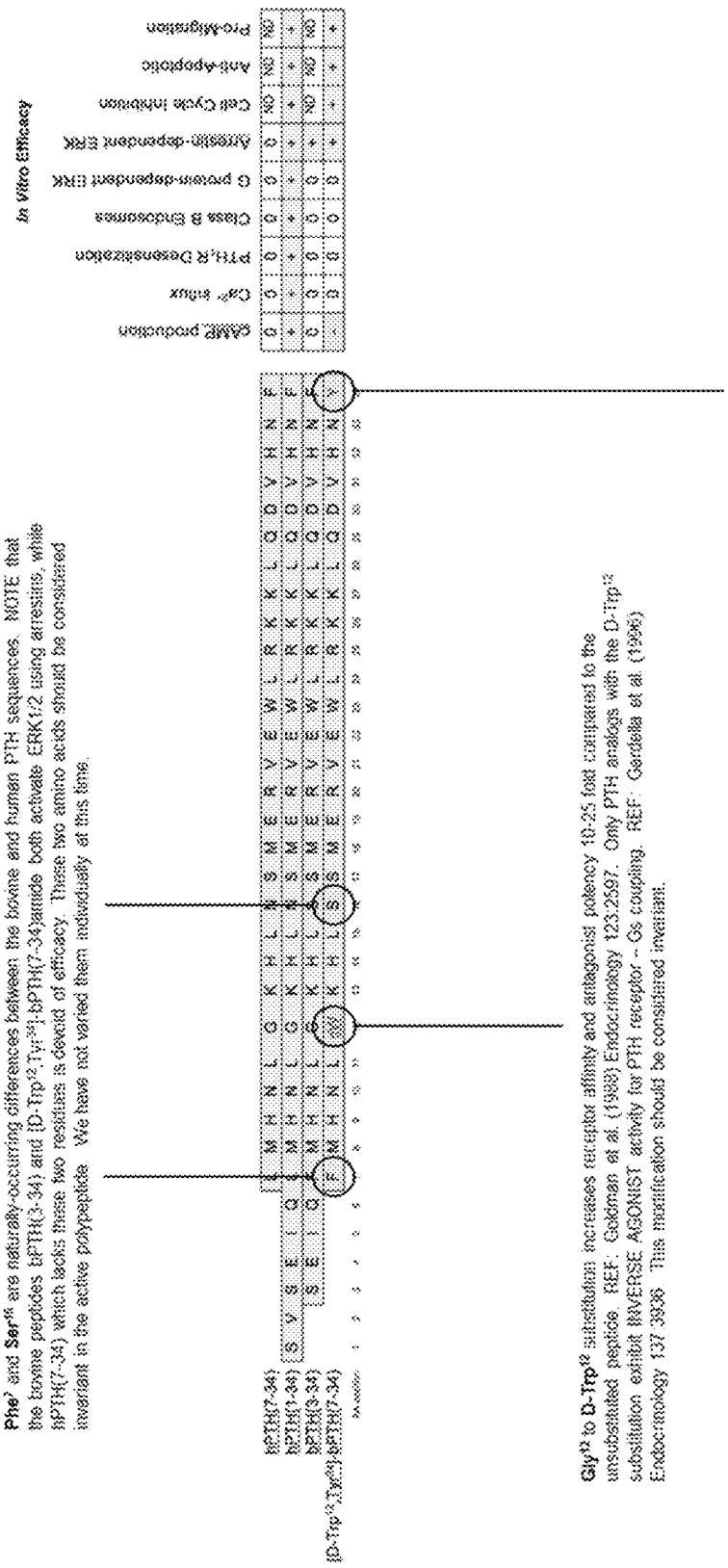
FIG. 21 shows an amino acid sequence alignment with efficacy comparison of human versus bovine PTH.

Effects of BDDP on bone osteolysis: FIG. 18 shows radiolucent regions of bone due to erosion of mineralized matrix by tumor. These have been confirmed by histology (FIG. 19), including immunohistochemical staining for the osteoclast marker, tartrate resistant acid phosphatase, at the tumor:bone interface.

BDDP does not affect tumor growth: PTHrP expression by tumor cells can have growth effects on the cells, but this growth effect does not seem to involve the PTH1R receptor (to which BDDP binds) and instead is the intracellular consequence of overexpressed PTHrP, perhaps on the nucleus [Johnson et al, 2018]. Consistent with this, no effect of BDDP was found on the growth in vitro of a series of human cancer cell lines reported to express PTHrP, including several prostate cancer and myeloma cell lines that grow in the bone of immunocompromised mouse hosts (FIG. 18). The results indicate that BDDP acts indirectly via bone to inhibit tumor growth through presently unknown cellular mechanisms.

Those skilled in the art will recognize, or be able to ascertain using no more than routine experimentation, many equivalents to the specific embodiments of the method and compositions described herein. Such equivalents are intended to be encompassed by the following claims.

REFERENCES

1. Appleton K M, Lee M-H, Alele C, et al. Biasing the Parathyroid Hormone Receptor. Methods in Enzymology: Elsevier; 2013. p. 229-62.
2. Birch M A, Carron J A, Scott M, et al. Parathyroid hormone/PTH-related protein receptor expression and mitogenic responses in human breast cancer cell lines. British Journal of Cancer. 1995; 72(1):90-5.
3. Bohinc B N, Gesty-Palmer D. Arrestins in Bone. Progress in Molecular Biology and Translational Science: Elsevier; 2013. p. 335-58.
4. Boudot C, Henaut L, Thiem U, et al. Overexpression of a functional calcium-sensing receptor dramatically increases osteolytic potential of MDA-MB-231 cells in a mouse model of bone metastasis through epiregulin-mediated osteoprotegerin downregulation. Oncotarget. 2017; 8(34).
5. Bravo-Sagua R, Mattar P, Diaz X, et al. Calcium Sensing Receptor as a Novel Mediator of Adipose Tissue Dysfunction: Mechanisms and Potential Clinical Implications. Frontiers in Physiology. 2016; 7.
6. Brooks S L, Neville A M, Rothwell N J, et al. Sympathetic activation of brown-adipose-tissue thermogenesis in cachexia. Bioscience Reports. 1981; 1(6):509-17.
7. Cafforio P, Savonarola A, Stucci S, et al. PTHrP produced by myeloma plasma cells regulates their survival and pro-osteoclast activity for bone disease progression. JBMR. 2013; 29(1):55-66.
8. Carron J A, Fraser W D, Gallagher J A. PTHrP and the PTH/PTHrP receptor are co-expressed in human breast and colon tumours. British Journal of Cancer. 1997; 76(8):1095-8.
9. Casey A E, Ross G L, Langston R R. Selective XYZ Factor in C57 Black Mammary Carcinoma Eo771. Experimental Biology and Medicine. 1949; 72(1):83-9.
10. Chirgwin J M, Guise T A. Molecular Mechanisms of Tumor-Bone Interactions in Osteolytic Metastases. Critical Reviews in Eukaryotic Gene Expression. 2000; 10(2): 20.
11. Chorev M, Goldman M E, et al. Modifications of position 12 in a parathyroid hormone and parathyroid hormone-related protein: toward the design of highly potent antagonists. Biochemistry. 1990; 29(6): 1580-6.
12. Chung E, Yamashita H, Au P, et al. Secreted Gaussia Luciferase as a Biomarker for Monitoring Tumor Progression and Treatment Response of Systemic Metastases. PLoS ONE. 2009; 4(12):e8316.
13. Clines G A. Mechanisms and treatment of hypercalcemia of malignancy. Current Opinion in Endocrinology & Diabetes and Obesity. 2011; 18(6):339-46.
14. Collin-Osdoby P, Yu X, et al. RANKL-Mediated Osteoclast Formation from Murine RAW 264.7 Cells. Bone Research Protocols: Humana Press. p. 153-66.
15. de la Mata J, Uy H L, Guise T A, et al. Interleukin-6 enhances hypercalcemia and bone resorption mediated by parathyroid hormone-related protein in vivo. Journal of Clinical Investigation. 1995; 95(6):2846-52.
16. de Paula F J A, Rosen C J. Structure and Function of Bone Marrow Adipocytes. Comprehensive Physiology: John Wiley & Sons, Inc.; 2017. p. 315-49.
17. Delgado-Calle J. Osteoclasts Control Lipid Secretion to Regulate Breast Cancer Bone Metastasis. Endocrinology. 2017; 158(3):458-60.
18. Delgado-Calle J, Anderson J, et al. Genetic deletion of Sost or pharmacological inhibition of sclerostin prevent multiple myeloma-induced bone disease without affecting tumor growth. Leukemia. 2017; 31(12):268694.
19. Delgado-Calle J, Tu X, Pacheco-Costa R, et al. Control of Bone Anabolism in Response to Mechanical Loading and PTH by Distinct Mechanisms Downstream of the PTH Receptor. JBMR. 2016; 32(3):522-35.
20. Dempster D W, Compston J E, Drezner M K, et al. Standardized nomenclature, symbols, and units for bone histomorphometry. JBMR. 2012; 28(1):2-17.
21. Dempster D W, Hughes-Begos C E, Plavetic-Chee K, et al. Normal human osteoclasts formed from peripheral blood monocytes express PTH type 1 receptors and are stimulated by PTH in the absence of osteoblasts. Journal of Cellular Biochemistry. 2005; 95(1):139-48.
22. Diel I J, Body J-J, Stopeck A T, et al. The role of denosumab in the prevention of hypercalcaemia of malignancy in cancer patients with metastatic bone disease. European Journal of Cancer. 2015; 51(11):146775.
23. Downey S E, Hoyland J, Freemont A J, et al. Expression of the receptor for parathyroid hormone-related protein in normal and malignant breast tissue. The Journal of pathology. 1997; 183(2):212-7.
24. Drew A F, Blick T J, Lafleur M A, et al. Correlation of tumor- and stromal-derived MT1-MMP expression with progression of human ovarian tumors in SCID mice. Gynecologic Oncology. 2004; 95(3):437-48.
25. Elefteriou F. Role of sympathetic nerves in the establishment of metastatic breast cancer cells in bone. Journal of Bone Oncology. 2016; 5(3):132-4.
26. Fairfield H, Falank C, Harris E, et al. The skeletal cell-derived molecule sclerostin drives bone marrow adipogenesis. Journal of Cellular Physiology. 2017; 233(2): 1156-67.
27. Falank C, Fairfield H, Reagan M R. Reflections on Cancer in the Bone Marrow: Adverse Roles of Adipocytes. Current Molecular Biology Reports. 2017; 3(4): 254-62.
28. Fallah-Rad N, Morton A R. Managing hypercalcaemia and hypocalcaemia in cancer patients. Current Opinion in Supportive and Palliative Care. 2013:1.
29. Falzon M. Enhanced Growth of MCF-7 Breast Cancer Cells Overexpressing Parathyroid Hormone-Related Peptide. Endocrinology. 2000; 141(5):1882-92.
30. Fan Y, Hanai J-i, Le P T, et al. Parathyroid Hormone Directs Bone Marrow Mesenchymal Cell Fate. Cell Metabolism. 2017; 25(3):661-72.
31. Faucheux C, Horton M A, Price J S. Nuclear Localization of Type I PTH/Parathyroid Hormone-Related Protein Receptors in Deer Antler Osteoclasts: Evidence for Parathyroid Hormone-Related Protein and Receptor Activator of NF-κB-Dependent Effects on Osteoclast Formation in Rege. JBMR. 2002; 17(3):455-64.

32. Ferguson J E, Seaner R M, et al. Expression and specific immunolocalization of the human PTH/PTHrP receptor in the uteroplacental unit. American Journal of Obstetrics and Gynecology. 1998; 179(2):321-9.
33. Fountas A, Andrikoula M, Giotaki Z et al. The emerging role of denosumab in the long-term management of parathyroid carcinoma-related refractory hypercalcemia. Endocrine Practice. 2015; 21(5):468-73.
34. Fournier P G J, Chirgwin J M, Guise T A. New insights into the role of T cells in the vicious cycle of bone metastases. Current Opinion in Rheumatology. 2006; 18(4):396-404.
35. Fukayama S, Kong G, Benovic J L, et al. (β-Adrenergic Receptor Kinase-1 Acutely Regulates PTH/PTHrP Receptor Signalling in Human Osteoblastlike Cells. Cellular Signalling. 1997; 9(6):469-74.
36. Gardella T J. Inverse agonism of amino-terminally truncated PTH and PTH-related peptide (PTHrP) analogs revealed with constitutively active mutant PTH/PTHrP receptors. Endocrinology. 1996; 137(9):3936-41.
37. Gesta S, Tseng Y-H, Kahn C R. Developmental Origin of Fat: Tracking Obesity to Its Source. Cell. 2007; 131 (2):242-56.
38. Gesty-Palmer D, Flannery P, Yuan L, et al. Arrestin-Biased Agonist of the Parathyroid Hormone Receptor Promotes Bone Formation Independent of G Protein Activation. Science Translational Medicine. 2009; 1(1)
39. Gesty-Palmer D, Luttrell L M. 'Biasing' the parathyroid hormone receptor: A novel anabolic approach to increasing bone mass? British Journal of Pharmacology. 2011; 164(1):59-67.
40. Gesty-Palmer D, Yuan L, Martin B, et al. P-Arrestin-Selective G Protein-Coupled Receptor Agonists Engender Unique Biological Efficacyin Vivo. Molecular Endocrinology. 2013; 27(2):296-314.
41. Goldman M E, McKee R L, Caulfield M P, et al. a new highly potent parathyroid hormone antagonist: [D-TRP12,TYR34]bPTH-(7-34)NH2. Endocrinology. 1988; 123(5):2597-9.
42. González Á, Garcia de Durango C, Alonso V, et al. Distinct Osteomimetic Response of Androgen-Dependent and Independent Human Prostate Cancer Cells to Mechanical Action of Fluid Flow: Prometastatic Implications. The Prostate. 2016; 77(3):321-33.
43. Grundmann M, Merten N, Malfacini D, et al. Lack of beta-arrestin signaling in the absence of active G proteins. Nature communications. 2018; 9(1).
44. Guise T A, Kozlow W M, Heras-Herzig A, et al. Molecular Mechanisms of Breast Cancer Metastases to Bone. Clinical Breast Cancer. 2005; 5:S46-S53.
45. Guise T A, Yin J J, Taylor S D, Kumagai Y, et al. Evidence for a causal role of PTHrP in the pathogenesis of human breast cancer-mediated osteolysis. Journal of Clinical Investigation. 1996; 98(7): 1544-9.
46. Harms M, Seale P. Brown and beige fat: development, function and therapeutic potential. Nature Medicine. 2013; 19(10): 1252-63.
47. Hattersley G, Dean T, Corbin B A, et al. Binding Selectivity of Abaloparatide for PTH-Type-1-Receptor Conformations and Effects on Downstream Signaling. Endocrinology. 2016; 157(1):141-9.
48. Hock J M, Gera I. Effects of continuous and intermittent administration and inhibition of resorption on the anabolic response of bone to parathyroid hormone. JBMR. 2009; 7(1):65-72.
49. Hu M I, Glezerman I G, Leboulleux S, et al. Denosumab for Treatment of Hypercalcemia of Malignancy. The Journal of Clinical Endocrinology & Metabolism. 2014; 99(9):3144-52.
50. Ikeda K, Mangin M, Dreyer B E, et al. Identification of transcripts encoding a parathyroid hormone-like peptide in messenger RNAs from a variety of human and animal tumors associated with humoral hypercalcemia of malignancy. Journal of Clinical Investigation. 1988; 81(6): 2010-4.
51. Iwamura M, Wu G, Abrahamsson P-A, et al. Parathyroid hormone-related protein: A potential autocrine growth regulator in human prostate cancer cell lines. Urology. 1994; 43(5):675-9.
52. Johnson R W, Suva L J. Hallmarks of Bone Metastasis. Calcified Tissue International. 2017; 102(2):141-51.
53. Juárez P, Fournier P G J, Mohammad K S, et al. Halofuginone inhibits TGF/BMP signaling and in combination with zoledronic acid enhances inhibition of breast cancer bone metastasis. Oncotarget. 2017; 8(49).
54. Juarez P, Mohammad K S, Yin J J, et al. Halofuginone Inhibits the Establishment and Progression of Melanoma Bone Metastases. Cancer Res. 2012; 72(23):6247-56.Kajimura S, Spiegelman B M, Seale P. Brown and Beige Fat: Physiological Roles beyond Heat Generation. Cell Metabolism. 2015; 22(4):546-59.
55. Käkönen S-M, Selander K S, Chirgwin J M, et al. Transforming Growth Factor-β Stimulates Parathyroid Hormone-related Protein and Osteolytic Metastases via Smad and Mitogen-activated Protein Kinase Signaling Pathways. Journal of Biological Chemistry. 2002; 277 (27):24571-8.
56. Kim B H, Pereverzev A, Zhu S, et al. Extracellular nucleotides enhance agonist potency at the parathyroid hormone 1 receptor. Cellular Signalling. 2018.
57. Kim S P, Frey J L, Li Z, et al. Sclerostin influences body composition by regulating catabolic and anabolic metabolism in adipocytes. Proceedings of the National Academy of Sciences. 2017; 114(52):E11238-E47.
58. Kim W, Takyar F M, Swan K, et al. Calcium-Sensing Receptor Promotes Breast Cancer by Stimulating Intracrine Actions of Parathyroid Hormone-Related Protein. Cancer Res. 2016; 76(18):5348-6
59. Kir S, Komaba H, Garcia Ana P, et al. PTH/PTHrP Receptor Mediates Cachexia in Models of Kidney Failure and Cancer. Cell Metabolism. 2016; 23(2):315-23.
60. Kir S, White J P, Kleiner S, Kazak L, et al. Tumour-derived PTH-related protein triggers adipose tissue browning and cancer cachexia. Nature. 2014; 513(7516): 100-4.
61. Kukreja S C, D'Anza J J, Wimbiscus S A, et al. Inactivation by plasma may be responsible for lack of efficacy of parathyroid hormone antagonists in hypercalcemia of malignancy. Endocrinology. 1994; 134(5):2184-8.
62. Langub M C, Malluche H H. Parathyroid Hormone Type 1 Receptor and Human Osteoclasts. JBMR. 2002; 17(10): 1916.
63. Lecka-Czernik B, Stechschulte L A, Czernik P J, et al. Marrow Adipose Tissue: Skeletal Location, Sexual Dimorphism, and Response to Sex Steroid Deficiency. Frontiers in Endocrinology. 2017; 8.
64. Leder B Z, O'Dea L S L, Zanchetta J R, et al. Effects of Abaloparatide, a Human Parathyroid Hormone-Related Peptide Analog, on Bone Mineral Density in Postmenopausal Women with Osteoporosis. The Journal of Clinical Endocrinology & Metabolism. 2015; 100(2):697-706.

65. Li J, Karaplis A C, Huang D C, et al. PTHrP drives breast tumor initiation, progression, and metastasis in mice and is a potential therapy target. Journal of Clinical Investigation. 2011; 121(12):4655-69.
66. Liao J, Li X, Koh A J, Berry J E, et al. Tumor expressed PTHrP facilitates prostate cancer-induced osteoblastic lesions. International Journal of Cancer. 2008; 123(10): 2267-78.
67. Lupp A, Klenk C, Rocken C, et al. Immunohistochemical identification of the PTHR1 parathyroid hormone receptor in normal and neoplastic human tissues. European Journal of Endocrinology. 2010; 162(5): 979-86.
68. Luttrell L M, Maudsley S, Bohn L M. Fulfilling the Promise of "Biased" G Protein-Coupled Receptor Agonism. Molecular Pharmacology. 2015; 88(3):579-88.
69. Luttrell L M, Maudsley S, Gesty-Palmer D. Translating in vitro ligand bias into in vivo efficacy. Cellular Signalling. 2018; 41:46-55.
70. Massfelder T, Parekh N, et al. Effect of intrarenally infused parathyroid hormone-related protein on renal blood flow and glomerular filtration rate in the anaesthetized rat. BJ of Pharmacology. 1996; 118(8): 1995-2000.
71. Maudsley S, Martin B, Janssens J, et al. Informatic deconvolution of biased GPCR signaling mechanisms from in vivo pharmacological experimentation. Methods. 2016; 92:51-63.
72. Mickle A D, Shepherd A J, Loo L, et al. Induction of thermal and mechanical hypersensitivity by parathyroid hormone—related peptide through upregulation of TRPV1 function and trafficking. PAIN. 2015; 156(9): 1620-36.
73. Milgrom D P, Lad N L, Koniaris L G, et al. Bone Pain and Muscle Weakness in Cancer Patients. Current Osteoporosis Reports. 2017; 15(2):76-87.
74. Mohammad K S, Chirgwin J M, Guise T A. Assessing New Bone Formation in Neonatal Calvarial Organ Cultures. Osteoporosis: Humana Press; 2008. p. 37-50.
75. Moseley J M, Kubota M, Diefenbach-Jagger H, et al. Parathyroid hormone-related protein purified from a human lung cancer cell line. Proceedings of the National Academy of Sciences. 1987; 84(14):5048-52.
76. Bohinc B, Gesty-Palmer D. Biased Agonism at the Parathyroid Hormone Receptor: A Demonstration of Functional Selectivity in Bone Metabolism. Mini-Reviews in Medicinal Chemistry. 2012; 12(9): 856-65.
77. Onuma E. Increased Renal Calcium Reabsorption by Parathyroid Hormone-Related Protein Is a Causative Factor in the Development of Humoral Hypercalcemia of Malignancy Refractory to Osteoclastic Bone Resorption Inhibitors. Clinical Cancer Research. 2005; 11(11):4198-203.
78. Parkes A, Clifton K, Al-Awadhi A, et al. Characterization of bone only metastasis patients with respect to tumor subtypes. npj Breast Cancer. 2018; 4(1).
79. Pennisi A, Ling W, Li X, et al. Consequences of Daily Administered Parathyroid Hormone on Myeloma Growth, Bone Disease, and Molecular Profiling of Whole Myelomatous Bone. PLoS ONE. 2010; 5(12):e15233.
80. Peters E M J, Foitzik K, Paus R, et al. A New Strategy for Modulating Chemotherapy-Induced Alopecia, Using PTH/PTHrP Receptor Agonist and Antagonist. Journal of Investigative Dermatology. 2001; 117(2): 173-8.
81. Bovenberg M S, Degeling M R, Tannous B A. Enhanced Gaussia luciferase blood assay for monitoring of in vivo biological processes. Anal Chem. 2012 Jan. 17; 84(2): 1189-92. doi: 10.1021/ac202833r. Epub 2011 Dec. 27. PMID: 22148161
82. Johnson R W, Sun Y, Ho P W M, Chan A S M, Johnson J A, Pavlos N J, Sims N A, Martin T J. Parathyroid Hormone-Related Protein Negatively Regulates Tumor Cell Dormancy Genes in a PTHR1/Cyclic AMP-Independent Manner. Front Endocrinol (Lausanne). 2018 May 16; 9:241. doi: 10.3389/fendo.2018.00241. eCollection 2018. PMID: 29867773
83. Maudsley S, Martin B, Gesty-Palmer D, Cheung H, Johnson C, Patel S, Becker K G, Wood W H 3rd, Zhang Y, Lehrmann E, Luttrell L M. Delineation of a conserved arrestin-biased signaling repertoire in vivo. Mol Pharmacol. 2015 April; 87(4):706-17. doi: 10.1124/mol.114.095224. Epub 2015 Jan. 30. PMID: 25637603
84. Siclari V A, Mohammad K S, Tompkins D R, Davis H, McKenna C R, Peng X, Wessner L L, Niewolna M, Guise T A, Suvannasankha A, Chirgwin J M. Tumor-expressed adrenomedullin accelerates breast cancer bone metastasis. Breast Cancer Res. 2014 Dec. 2; 16(6):458. doi: 10.1186/s13058-014-0458-y. PMID: 25439669
85. Wright L E, Ottewell P D, Rucci N, Peyruchaud O, Pagnotti G M, Chiechi A, Buijs J T, Sterling J A. Murine models of breast cancer bone metastasis. Bonekey Rep. 2016 May 11; 5:804. eCollection 2016. PMID: 27867497
86. Peterson Y K, Luttrell L M. The Diverse Roles of Arrestin Scaffolds in G Protein-Coupled Receptor Signaling. Pharmacological Reviews. 2017; 69(3):256-97.
87. Pierroz D D, Rufo A, Bianchi E N, et al. 13-Arrestin2 Regulates RANKL and Ephrins Gene Expression in Response to Bone Remodeling in Mice. JBMR. 2009; 24(5): 775-84.
88. Pizurki L, Rizzoli R, Bonjour J P. Inhibition by (D-Trp12,Tyr34)bPTH(7-34)amide of PTH and PTHrP effects on Pi transport in renal cells. American Journal of Physiology-Renal Physiology. 1990; 259(2):F389-F92.
89. Qiu T, Wu X, Zhang F, et al. TGF-l3 type II receptor phosphorylates PTH receptor to integrate bone remodelling signalling. Nature Cell Biology. 2010.
90. Rahman S, Lu Y, Czernik P J, et al. Inducible Brown Adipose Tissue, or Beige Fat, Is Anabolic for the Skeleton. Endocrinology. 2013; 154(8):2687-701.
91. Rickard D J, Wang F-L, Rodriguez-Rojas A-M, et al. Intermittent treatment with PTH as well as a non-peptide small molecule agonist of the PTH1 receptor inhibits adipocyte differentiation in human bone marrow stromal cells. Bone. 2006; 39(6):1361-72.
92. Rosen E D, Spiegelman B M. Adipocytes as regulators of energy balance and glucose homeostasis. Nature. 2006; 444(7121):847-53.
93. Rosen E D, Spiegelman B M. What We Talk About When We Talk About Fat. Cell. 2014; 156(1-2):20-44.
94. Santos-Zas I, Lodeiro M, Gurriaran-Rodriguez U, et al. 13-Arrestin signal complex plays a critical role in adipose differentiation. The International Journal of Biochemistry & Cell Biology. 2013; 45(7):1281-92.
95. Sato K. Treatment of malignancy-associated hypercalcemia and cachexia with humanized anti-parathyroid hormone-related protein antibody. Seminars in Oncology. 2003; 30:167-73.
96. Shepherd A J, Mickle A D, Kadunganattil S, et al. Parathyroid Hormone-Related Peptide Elicits Peripheral TRPV1-dependent Mechanical Hypersensitivity. Frontiers in cellular neuroscience. 2018; 12.
97. Siclari V A, Mohammad K S, Tompkins D R, et al. Tumor-expressed adrenomedullin accelerates breast cancer bone metastasis. Breast Cancer Research. 2014; 16(6).
98. Skrok A, Bednarczuk T, Skwarek A, et al. The Effect of PTHs on Hair Follicle Physiology: Implications for Treat- 99. Strewler G J, Stern P H, Jacobs J W, et al. Parathyroid hormonelike protein from human renal carcinoma cells. Structural and functional homology with parathyroid hormone. J Clinical Investigation. 1987; 80(6):1803-7.
100. Suva L, Winslow G, Wettenhall R, et al. A parathyroid hormone-related protein implicated in malignant hypercalcemia: cloning and expression. Science. 1987; 237 (4817): 893-6.
101. Suvannasankha A, Chirgwin J M. Role of bone-anabolic agents in the treatment of breast cancer bone metastases. Breast Cancer Research. 2014; 16(6).
102. Swami S, Johnson J, Bettinson L A, et al. Prevention of breast cancer skeletal metastases with parathyroid hormone. JCI Insight. 2017; 2(17).
103. Tannous B A, Teng J. Secreted blood reporters: Biotechnology Advances. 2011; 29(6): 997-1003.
104. Tsuzuki S, Park S H, Eber M R, et al. Skeletal complications in cancer patients with bone metastases. International Journal of Urology. 2016; 23(10):825-32.
105. Weng T, Mao F, Wang Y, et al. Osteoblastic molecular scaffold Gab1 is required for maintaining bone homeostasis. Journal of Cell Science. 2010; 123(5):682-9.
106. Wright L E, Ottewell P D, et al. Murine models of breast cancer bone metastasis. BoneKEy reports. 2016; 5.
107. Wu G, Iwamura M, Di Sant'agnese P A, et al. Characterization of the cell-specific expression of parathyroid hormone-related protein in normal and neoplastic prostate tissue. Urology. 1998; 51(5):110-20.
108. Wysolmerski J J, Stewart A F. the physiology of parathyroid hormone-related protein: An Emerging Role as a Developmental Factor. Annual Review of Physiology. 1998; 60(1):431-60.
109. Xiao N, Li H, Mei W, et al. SUMOylation Attenuates Human 13-Arrestin 2 Inhibition of IL-1R/TRAF6 Signaling. Journal of Biological Chemistry. 2014; 290(4):1927-35.
110. Yaccoby S. Osteoblastogenesis and tumor growth in myeloma. Leukem & Lymphoma. 2009; 51:213-20.
111. Yin J J, Selander K, Chirgwin J M, et al. TGF-13 signaling blockade inhibits PTHrP secretion by breast cancer cells and bone metastases development. Journal of Clinical Investigation. 1999; 103(2): 197-206.
112. Yoneda T, Hiasa M, Nagata Y, et al. Acidic microenvironment and bone pain in cancer-colonized bone. BoneKEy reports. 2015; 4.
113. Zangari M, Berno T, Yang Y, et al. Parathyroid hormone receptor mediates the anti-myeloma effect of proteasome inhibitors. Bone. 2014; 61:39-43.
114. Zhang X, Cheng Q, Wang Y, et al. Hedgehog signaling in bone regulates whole-body energy metabolism through a bone-adipose endocrine relay mediated by PTHrP and adiponectin. Cell Death & Differentiation. 2016; 24(2): 225-37.
115. Zhou J Z, Riquelme M A, Gao X, et al. Differential impact of adenosine nucleotides released by osteocytes on breast cancer growth and bone metastasis. Oncogene. 2014; 34(14): 1831-42.

We claim:

1. A method of decreasing cancer-related cachexia in a subject with bone cancer comprising administering to the subject a therapeutically effective amount of bPTH7-34DD, wherein the bPTH7-34DD blocks parathyroid hormone-related protein (PTHrP), wherein the therapeutically effective amount of bPTH7-34DD is administered subcutaneously, intramuscularly, or intravenously.

2. The method of claim 1, wherein the therapeutically effective amount of bPTH7-34DD is 40-1000 µg/kg/d.

3. The method of claim 1, wherein the bone cancer metastasized from lung cancer, prostate cancer, kidney cancer, breast cancer, or multiple myeloma.

4. The method of claim 1, further comprising administering a second therapeutic to the subject.

5. The method of claim 4, wherein the second therapeutic is a bone anabolic treatment.

6. The method of claim 1, wherein the bPTH7-34DD is administered in a continuous administration.

7. The method of claim 1, wherein the bPTH7-34DD inhibits white to brown adipocyte conversion.

* * * * *